(12) United States Patent
Zhang et al.

(10) Patent No.: US 11,530,264 B2
(45) Date of Patent: Dec. 20, 2022

(54) MULTIFUNCTIONAL PROTEIN

(71) Applicant: Shenzhen Beike Biotechnology Co., Ltd, Shenzhen (CN)

(72) Inventors: Fengyu Zhang, Tianjin (CN); Bin Gao, Tianjin (CN); Lei Wang, Tianjin (CN); Yasong Wu, Tianjin (CN); Qing Wei, Tianjin (CN)

(73) Assignee: SHENZHEN BEIKE BIOTECHNOLOGY CO., LTD, Shenzhen (CN)

( * ) Notice: Subject to any disclaimer, the term of this patent is extended or adjusted under 35 U.S.C. 154(b) by 438 days.

(21) Appl. No.: 16/475,060

(22) PCT Filed: Dec. 27, 2017

(86) PCT No.: PCT/CN2017/118984
§ 371 (c)(1),
(2) Date: Jun. 28, 2019

(87) PCT Pub. No.: WO2018/121605
PCT Pub. Date: Jul. 5, 2018

(65) Prior Publication Data
US 2022/0064289 A1    Mar. 3, 2022

(30) Foreign Application Priority Data
Dec. 29, 2016 (CN) .......................... 201611246592.0

(51) Int. Cl.
| C07K 16/28 | (2006.01) |
| C07K 14/54 | (2006.01) |
| C07K 14/705 | (2006.01) |
| C07K 14/715 | (2006.01) |
| C07K 16/46 | (2006.01) |

(52) U.S. Cl.
CPC ...... *C07K 16/2803* (2013.01); *C07K 14/5443* (2013.01); *C07K 14/70521* (2013.01); *C07K 14/70532* (2013.01); *C07K 14/7155* (2013.01); *C07K 16/2809* (2013.01); *C07K 16/2833* (2013.01); *C07K 16/468* (2013.01); *C07K 2317/31* (2013.01); *C07K 2317/569* (2013.01); *C07K 2317/622* (2013.01); *C07K 2319/02* (2013.01); *C07K 2319/30* (2013.01)

(58) Field of Classification Search
CPC ............ C07K 16/2803; C07K 14/5443; C07K 14/70521; C07K 14/70532; C07K 14/7155; C07K 16/2809; C07K 16/2833; C07K 16/468; C07K 2317/31; C07K 2317/569; C07K 2317/622; C07K 2319/02; C07K 2319/30; C07K 14/5406; C07K 14/4747; C07K 14/70596; C07K 2317/73; C07K 2319/00; C07K 2319/33; C07K 16/2818; C07K 16/2827; C07K 16/283; C07K 16/2854; C07K 16/30; A61P 35/00; C12N 5/0636; C12N 5/0646; A61K 38/00
See application file for complete search history.

(56) References Cited

U.S. PATENT DOCUMENTS

| 2004/0220388 A1* | 11/2004 | Mertens ................. C07K 16/00 530/388.8 |
| 2014/0099254 A1* | 4/2014 | Chang .................... C07K 16/30 424/1.11 |
| 2014/0242025 A1* | 8/2014 | Wong ..................... A61P 35/00 424/135.1 |

FOREIGN PATENT DOCUMENTS

| CN | 101743249 | 6/2010 | |
| CN | 102573922 | 7/2012 | |
| WO | WO-2006119897 A2 * | 11/2006 | ......... C07K 14/5434 |
| WO | 2008143794 A1 | 11/2008 | |
| WO | 2012040323 A2 | 3/2012 | |
| WO | WO-2014153114 A1 * | 9/2014 | ........... A61K 38/177 |

OTHER PUBLICATIONS

Lloyd et al., Protein Engineering, Design & Selection 22:159-168 (Year: 2009).*
Edwards et al., J Mol Biol 334(1): 103-118 (Year: 2003).*
Piche-Nicholas et al., MABS 10(1): 81-94 (Year: 2018).*
International search report dated Mar. 27, 2018 from corresponding application No. PCT/CN2017/118984.
Second Office Action issued in corresponding Chinese Application No. 201780029217.7; dated Jul. 30, 2021; State Intellectual Property Office of the P.R. China, Beijing, China, 11 pgs.
First Office Action issued in corresponding Chinese Application No. 201780029217.7; dated Feb. 26, 2021; State Intellectual Property Office of the P.R. China, Beijing, China, 25 pgs.
Extended European Search Report issued in corresponding European Application No. 17888600.8; dated Nov. 24, 2020; 8 pgs.
Halin, C. et al.; "Synergistic Therapeutic Effects of a Tumor Targeting Antibody Fragment, Fused to Interleukin 12 and to Tumor Necrosis Factor a1", Cancer Research, Jun. 15, 2003; 10 pgs.

(Continued)

*Primary Examiner* — Phuong Huynh
(74) *Attorney, Agent, or Firm* — Hauptman Ham, LLP

(57) ABSTRACT

A multifunctional polypeptide chain or a protein. A polypeptide chain X, comprising an antigen 1 binding domain R1, an auxiliary peptide chain linking domain R2 and an antigen 2 binding domain R3. The auxiliary peptide chain linking domain R2 is a cytokine or a cytokine binding domain in a cytokine receptor. A protein, which is a heterodimer composed of the polypeptide chain X as a main peptide chain and an auxiliary peptide chain Y. The auxiliary peptide chain Y comprises an antigen 3 binding domain R4 and a main peptide chain X linking domain R5, or the auxiliary peptide chain Y is the main peptide chain linking domain R5. The multifunctional protein mediates specific cell killing by binding to different tumor antigens with the two antigen binding domains of tumor-associated antigens therein. The multifunctional protein can function as a cytokine by introducing a cytokine or a cytokine receptor complex.

Figure 1:
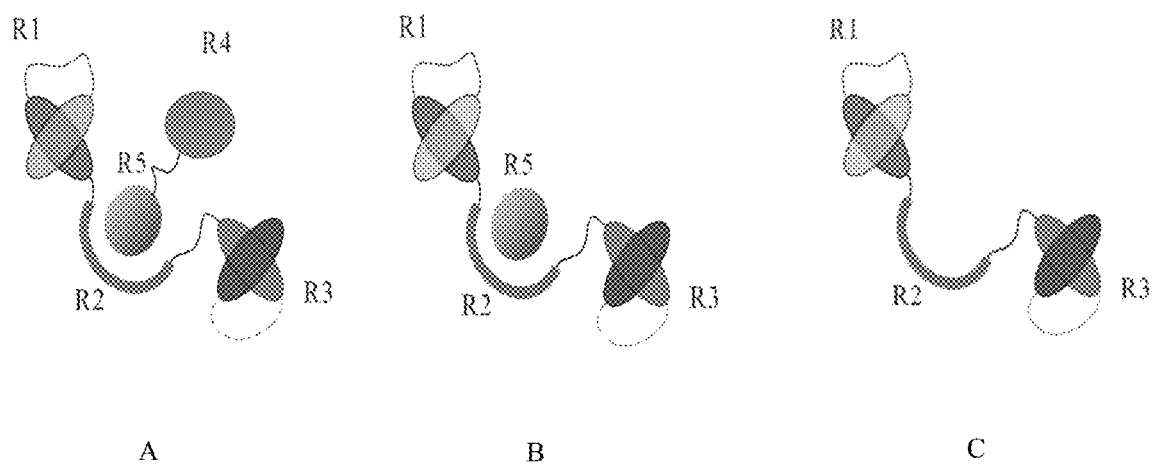

3 Claims, 16 Drawing Sheets
Specification includes a Sequence Listing.

(56) References Cited

OTHER PUBLICATIONS

Kim, P. et al.; "IL-15 superagonist/IL-15RaSushi-Fc fusion complex (IL-15SA/IL-15RaSu-Fc; ALT-803) markedly enhances specific sub-populations of NK and memory CD8+ T cells, and mediates potent anti-tumor activity against murine breast and colon carcinomas", Oncotarget, vol. 7, No. 13, Feb. 18, 2016; 16 pgs.

\* cited by examiner

A			B

C

D

E

F

A    B

A                B

C                D

A　　　　　　B　　　　　　C　　　　　　D

E　　　　　　F　　　　　　G　　　　　　H

A    B    C    D

SEQUENCE LISTING

```
<160> NUMBER OF SEQ ID NOS: 52

<210> SEQ ID NO 1
<211> LENGTH: 245
<212> TYPE: PRT
<213> ORGANISM: Artificial sequence
<220> FEATURE:
<223> OTHER INFORMATION: Synthesized

<400> SEQUENCE: 1

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
                20                  25                  30

Leu Asn Trp Tyr Gln Gln Lys Pro Asp Gly Thr Val Lys Leu Leu Ile
            35                  40                  45

Tyr His Thr Ser Arg Leu His Ser Gly Val Pro Ser Arg Phe Ser Gly
        50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
                100                 105                 110

Ser Gly Lys Pro Gly Ser Gly Glu Gly Ser Thr Lys Gly Glu Val Lys
            115                 120                 125

Leu Gln Glu Ser Gly Pro Gly Leu Val Ala Pro Ser Gln Ser Leu Ser
130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
                180                 185                 190

Thr Ile Ile Lys Asp Asn Ser Lys Ser Gln Val Phe Leu Lys Met Asn
            195                 200                 205

Ser Leu Gln Thr Asp Asp Thr Ala Ile Tyr Tyr Cys Ala Lys His Tyr
        210                 215                 220

Tyr Tyr Gly Gly Ser Tyr Ala Met Asp Tyr Trp Gly Gln Gly Thr Ser
225                 230                 235                 240

Val Thr Val Ser Ser
                245
```

<210> SEQ ID NO 2
<211> LENGTH: 72
<212> TYPE: PRT
<213> ORGANISM: Artificial sequence
<220> FEATURE:
<223> OTHER INFORMATION: Synthesized

<400> SEQUENCE: 2

```
Ile Thr Cys Pro Pro Met Ser Val Glu His Ala Asp Ile Trp Val
1               5                  10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln
65                  70
```

<210> SEQ ID NO 3
<211> LENGTH: 242
<212> TYPE: PRT
<213> ORGANISM: Artificial sequence
<220> FEATURE:
<223> OTHER INFORMATION: Synthesized

<400> SEQUENCE: 3

```
Asp Ile Gln Met Thr Gln Ser Pro Ser Ser Leu Ser Ala Ser Val Gly
1               5                  10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Ser Glu Val Gln Leu Val Glu
        115                 120                 125

Ser Gly Gly Gly Leu Val Gln Pro Gly Gly Ser Leu Arg Leu Ser Cys
    130                 135                 140

Ala Ala Ser Gly Tyr Ser Phe Thr Gly Tyr Thr Met Asn Trp Val Arg
145                 150                 155                 160

Gln Ala Pro Gly Lys Gly Leu Glu Trp Val Ala Leu Ile Asn Pro Tyr
                165                 170                 175

Lys Gly Val Ser Thr Tyr Asn Gln Lys Phe Lys Asp Arg Phe Thr Ile
            180                 185                 190

Ser Val Asp Lys Ser Lys Asn Thr Ala Tyr Leu Gln Met Asn Ser Leu
        195                 200                 205

Arg Ala Glu Asp Thr Ala Val Tyr Tyr Cys Ala Arg Ser Gly Tyr Tyr
    210                 215                 220

Gly Asp Ser Asp Trp Tyr Phe Asp Val Trp Gly Gln Gly Thr Leu Val
```

Thr Val

<210> SEQ ID NO 4
<211> LENGTH: 150
<212> TYPE: PRT
<213> ORGANISM: Artificial sequence
<220> FEATURE:
<223> OTHER INFORMATION: Synthesized

<400> SEQUENCE: 4

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 5
<211> LENGTH: 114
<212> TYPE: PRT
<213> ORGANISM: Artificial sequence
<220> FEATURE:
<223> OTHER INFORMATION: Synthesized

<400> SEQUENCE: 5

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Lys Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 6

<211> LENGTH: 1815
<212> TYPE: DNA
<213> ORGANISM: Artificial sequence
<220> FEATURE:
<223> OTHER INFORMATION: Synthesized

<400> SEQUENCE: 6

| | | | | | |
|---|---|---|---|---|---|
| atggccttac | cagtgaccgc | cttgctcctg | ccgctggcct | tgctgctcca | cgccgccagg | 60 |
| ccggatatcc | agatgacaca | gactacatcc | tccctgtctg | cctctctggg | agacagagtc | 120 |
| accatcagtt | gcagggcaag | tcaggacatt | agtaaatatt | taaattggta | tcagcagaaa | 180 |
| ccagatggaa | ctgttaaact | cctgatctac | catacatcaa | gattacactc | aggagtccca | 240 |
| tcaaggttca | gtggcagtgg | gtctggaaca | gattattctc | tcaccattag | caacctggag | 300 |
| caagaagata | ttgccactta | cttttgccaa | cagggtaata | cgcttccgta | cacgttcgga | 360 |
| ggggggacca | agctggagat | cacaggctcc | acctctggct | ccggcaagcc | cggatctggc | 420 |
| gagggctcca | ccaagggcga | ggtgaaactg | caggagtcag | gacctggcct | ggtggcgccc | 480 |
| tcacagagcc | tgtccgtcac | atgcactgtc | tcagggtct | cattacccga | ctatggtgta | 540 |
| agctggattc | gccagcctcc | acgaaagggt | ctggagtggc | tgggagtaat | atggggtagt | 600 |
| gaaaccacat | actataattc | agctctcaaa | tccagactga | ccatcatcaa | ggacaactcc | 660 |
| aagagccaag | ttttcttaaa | aatgaacagt | ctgcaaactg | atgacacagc | catttactac | 720 |
| tgtgccaaac | attattacta | cggtggtagc | tatgctatgg | actactgggg | ccaaggaacc | 780 |
| tcagtcaccg | tgagctcagg | cggcggcgga | tctatcacgt | gccctccccc | catgtccgtg | 840 |
| gaacacgcag | acatctgggt | caagagctac | agcttgtact | ccaggagcg | gtacatttgt | 900 |
| aactctggtt | tcaagcgtaa | agccggcacg | tccagcctga | cggagtgcgt | gttgaacaag | 960 |
| gccacgaatg | tcgcccactg | gacaaccccc | agtctcaaat | gcattagaga | ccctgccctg | 1020 |
| gttcaccaaa | gcggcggctc | cggggaggt | ggatccggag | gtggctccgg | tggaggcgga | 1080 |
| agcctgcagg | atatccagat | gacccagtcc | ccgagctccc | tgtccgctag | cgtgggcgat | 1140 |
| agggtcacca | tcacctgtcg | tgccagtcag | gacatccgta | attatctcaa | ctggtatcaa | 1200 |
| cagaaaccag | gaaaagctcc | gaaactactg | atttactata | cctcccgcct | ggagtctgga | 1260 |
| gtcccttctc | gcttctctgg | ttctggttct | gggacggatt | acactctgac | catcagcagt | 1320 |
| ctgcaaccgg | aggacttcgc | aacttattac | tgtcagcaag | gtaatactct | gccgtggacg | 1380 |
| ttcggacagg | gcaccaaggt | ggagatcaaa | ggtggaggcg | gttcaggcgg | aggtggctct | 1440 |
| ggcggtggcg | gatcggaggt | tcagctggtg | gagtctggcg | gtggcctggt | gcagccaggg | 1500 |
| ggctcactcc | gtttgtcctg | tgcagcttct | ggctactcct | ttaccggcta | cactatgaac | 1560 |
| tgggtgcgtc | aggccccagg | taagggcctg | gaatggttg | cactgattaa | tccttataaa | 1620 |
| ggtgtttcca | cctataacca | gaaattcaag | gatcgtttca | cgatatccgt | agataaatcc | 1680 |
| aaaaacacag | cctacctgca | aatgaacagc | ctgcgtgctg | aggacactgc | cgtctattat | 1740 |
| tgtgctagaa | gcggatacta | cggcgatagc | gactggtatt | ttgacgtctg | gggtcaagga | 1800 |
| accctggtca | ccgtc | | | | | 1815 |

<210> SEQ ID NO 7
<211> LENGTH: 873
<212> TYPE: DNA
<213> ORGANISM: Artificial sequence
<220> FEATURE:
<223> OTHER INFORMATION: Synthesized

<400> SEQUENCE: 7

```
ggaagcggcg ccaccaactt ctccctgctg aagcaagctg gcgacgtgga agagaacccc    60
ggccccccag gatggttctt agactcccca gacaggccct ggaaccccc  caccttctcc   120 ccagccctgc tcgtggtgac cgaagggac  aacgccacct tcacctgcag cttctccaac   180
acatcggaga gcttcgtgct aaactggtac cgcatgagcc ccagcaacca gacggacaag   240
ctggccgcct tccccgagga ccgcagccag cccggccagg actgccgctt ccgtgtcaca   300
caactgccca cgggcgtgaa cttccacatg agcgtggtca gggcccggcg caatgacagc   360
ggcacctacc tctgtggggc catctccctg ccccccaagg cgcagatcaa agagagcctg   420
cgggcagagc tcagggtgac agagagaagg gcagaagtgc ccacagccca ccccagcccc   480
tcacccaggc cagccggcca gttccaaacc ctggtgggcg aggaggctc  caactgggtg   540 aacgtcatct ccgacctcaa gaagatcgag gacctgatcc agagcatgca catcgacgcc   600
accctgtata ccgagagcga cgtgcacccc tcctgtaaag tgaccgccat gaagtgcttc   660
ctgctggagc tgcaggtgat cagcctggag agcggcgacg ccagcatcca tgacaccgtg   720
gagaacctga tcatcctggc caataacagc ctgagctcca acggcaacgt gaccgagagc   780
ggctgcaagg aatgcgagga gctggagaag aagaacatta aggagttcct gcagagcttc   840
gtccacatcg tgcagatgtt cattaacacc tcc                               873

<210> SEQ ID NO 8
<211> LENGTH: 605
<212> TYPE: PRT
<213> ORGANISM: Artificial sequence
<220> FEATURE:
<223> OTHER INFORMATION: Synthesized

<400> SEQUENCE: 8

Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Ser Thr Ser Gly Ser Gly Lys Pro Gly Ser Gly Glu Gly Ser Thr
    130                 135                 140

Lys Gly Glu Val Lys Leu Gln Glu Ser Gly Pro Gly Leu Val Ala Pro
145                 150                 155                 160

Ser Gln Ser Leu Ser Val Thr Cys Thr Val Ser Gly Val Ser Leu Pro
                165                 170                 175

Asp Tyr Gly Val Ser Trp Ile Arg Gln Pro Pro Arg Lys Gly Leu Glu
            180                 185                 190

Trp Leu Gly Val Ile Trp Gly Ser Glu Thr Thr Tyr Tyr Asn Ser Ala
        195                 200                 205
```

Leu Lys Ser Arg Leu Thr Ile Ile Lys Asp Asn Ser Lys Ser Gln Val
        210                 215                 220

Phe Leu Lys Met Asn Ser Leu Gln Thr Asp Asp Thr Ala Ile Tyr Tyr
225                 230                 235                 240

Cys Ala Lys His Tyr Tyr Tyr Gly Gly Ser Tyr Ala Met Asp Tyr Trp
                245                 250                 255

Gly Gln Gly Thr Ser Val Thr Val Ser Ser Gly Gly Gly Gly Ser Ile
                260                 265                 270

Thr Cys Pro Pro Pro Met Ser Val Glu His Ala Asp Ile Trp Val Lys
        275                 280                 285

Ser Tyr Ser Leu Tyr Ser Arg Glu Arg Tyr Ile Cys Asn Ser Gly Phe
290                 295                 300

Lys Arg Lys Ala Gly Thr Ser Ser Leu Thr Glu Cys Val Leu Asn Lys
305                 310                 315                 320

Ala Thr Asn Val Ala His Trp Thr Thr Pro Ser Leu Lys Cys Ile Arg
                325                 330                 335

Asp Pro Ala Leu Val His Gln Ser Gly Gly Ser Gly Gly Gly Gly Ser
                340                 345                 350

Gly Gly Gly Ser Gly Gly Gly Ser Leu Gln Asp Ile Gln Met Thr
                355                 360                 365

Gln Ser Pro Ser Ser Leu Ser Ala Ser Val Gly Asp Arg Val Thr Ile
370                 375                 380

Thr Cys Arg Ala Ser Gln Asp Ile Arg Asn Tyr Leu Asn Trp Tyr Gln
385                 390                 395                 400

Gln Lys Pro Gly Lys Ala Pro Lys Leu Leu Ile Tyr Tyr Thr Ser Arg
                405                 410                 415

Leu Glu Ser Gly Val Pro Ser Arg Phe Ser Gly Ser Gly Ser Gly Thr
                420                 425                 430

Asp Tyr Thr Leu Thr Ile Ser Ser Leu Gln Pro Glu Asp Phe Ala Thr
                435                 440                 445

Tyr Tyr Cys Gln Gln Gly Asn Thr Leu Pro Trp Thr Phe Gly Gln Gly
        450                 455                 460

Thr Lys Val Glu Ile Lys Gly Gly Gly Gly Ser Gly Gly Gly Gly Ser
465                 470                 475                 480

Gly Gly Gly Gly Ser Glu Val Gln Leu Val Glu Ser Gly Gly Gly Leu
                485                 490                 495

Val Gln Pro Gly Gly Ser Leu Arg Leu Ser Cys Ala Ala Ser Gly Tyr
                500                 505                 510

Ser Phe Thr Gly Tyr Thr Met Asn Trp Val Arg Gln Ala Pro Gly Lys
        515                 520                 525

Gly Leu Glu Trp Val Ala Leu Ile Asn Pro Tyr Lys Gly Val Ser Thr
        530                 535                 540

Tyr Asn Gln Lys Phe Lys Asp Arg Phe Thr Ile Ser Val Asp Lys Ser
545                 550                 555                 560

Lys Asn Thr Ala Tyr Leu Gln Met Asn Ser Leu Arg Ala Glu Asp Thr
                565                 570                 575

Ala Val Tyr Tyr Cys Ala Arg Ser Gly Tyr Tyr Gly Asp Ser Asp Trp
                580                 585                 590

Tyr Phe Asp Val Trp Gly Gln Gly Thr Leu Val Thr Val
                595                 600                 605

<210> SEQ ID NO 9
<211> LENGTH: 269

<212> TYPE: PRT
<213> ORGANISM: Artificial sequence
<220> FEATURE:
<223> OTHER INFORMATION: Synthesized

<400> SEQUENCE: 9

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Gly Gly Gly Ser Asn Trp Val Asn Val
145                 150                 155                 160

Ile Ser Asp Leu Lys Lys Ile Glu Asp Leu Ile Gln Ser Met His Ile
                165                 170                 175

Asp Ala Thr Leu Tyr Thr Glu Ser Asp Val His Pro Ser Cys Lys Val
            180                 185                 190

Thr Ala Met Lys Cys Phe Leu Leu Glu Leu Gln Val Ile Ser Leu Glu
        195                 200                 205

Ser Gly Asp Ala Ser Ile His Asp Thr Val Glu Asn Leu Ile Ile Leu
    210                 215                 220

Ala Asn Asn Ser Leu Ser Ser Asn Gly Asn Val Thr Glu Ser Gly Cys
225                 230                 235                 240

Lys Glu Cys Glu Glu Leu Glu Lys Lys Asn Ile Lys Glu Phe Leu Gln
                245                 250                 255

Ser Phe Val His Ile Val Gln Met Phe Ile Asn Thr Ser
            260                 265

<210> SEQ ID NO 10
<211> LENGTH: 125
<212> TYPE: PRT
<213> ORGANISM: Artificial sequence
<220> FEATURE:
<223> OTHER INFORMATION: Synthesized

<400> SEQUENCE: 10

Asp Val Gln Leu Gln Ala Ser Gly Gly Gly Leu Val Gln Pro Gly Gly
1               5                   10                  15

Ser Leu Arg Leu Ser Cys Ala Ala Ser Gly Arg Thr Phe Asn Val Asp
            20                  25                  30

Ala Met Ala Trp Phe Arg Gln Thr Arg Gly Lys Glu Arg Glu Phe Val
        35                  40                  45

Ala Ala Ile Ser Arg Ser Gly Gly Ser Thr Tyr Tyr Ala Asp Ser Val
    50                  55                  60

```
Lys Gly Arg Phe Ser Ile Ser Lys Asp Asn Ala Lys Asn Thr Met Tyr
 65                  70                  75                  80

Leu Gln Met Asn Ser Leu Lys Pro Glu Asp Thr Ala Ile Tyr Tyr Cys
                 85                  90                  95

Ala Ala Ala Ile Tyr Trp Arg Gly Ser Tyr Tyr Thr Glu Gly Asn Tyr
            100                 105                 110

Asp Tyr Trp Gly Gln Arg Thr Gln Val Thr Val Ser Ser
        115                 120                 125

<210> SEQ ID NO 11
<211> LENGTH: 117
<212> TYPE: PRT
<213> ORGANISM: Artificial sequence
<220> FEATURE:
<223> OTHER INFORMATION: Synthesized

<400> SEQUENCE: 11

Asp Val Gln Leu Gln Ala Ser Gly Gly Gly Leu Val Gln Ala Gly Asp
  1               5                  10                  15

Ser Leu Arg Leu Ser Cys Ala Ala Ser Gly Arg Thr Phe Ser Thr Tyr
                 20                  25                  30

Asn Met Gly Trp Phe Arg Gln Ala Pro Gly Lys Asp Arg Glu Phe Val
            35                  40                  45

Ala Ala Ile Met Trp Ser Gly Gly Ser Thr Tyr Tyr Ala Asp Ser Val
        50                  55                  60

Lys Gly Arg Phe Thr Ile Ser Lys Asp Asn Ala Lys Asn Thr Val Tyr
 65                  70                  75                  80

Leu Gln Met Asn Ser Leu Lys Pro Glu Asp Thr Ala Val Tyr Phe Cys
                 85                  90                  95

Trp Ser Thr Asp Asp Tyr Gly Val Asp Ser Trp Gly Gln Gly Thr Gln
            100                 105                 110

Val Thr Val Ser Ser
        115

<210> SEQ ID NO 12
<211> LENGTH: 118
<212> TYPE: PRT
<213> ORGANISM: Artificial sequence
<220> FEATURE:
<223> OTHER INFORMATION: Synthesized

<400> SEQUENCE: 12

Gln Leu Leu Glu Ser Gly Gly Gly Leu Val Gln Pro Gly Gly Ser Leu
  1               5                  10                  15

Arg Leu Ser Cys Ala Ala Ser Gly Tyr Arg Ile Ser Ser Asp Asp Met
                 20                  25                  30

Ser Trp Val Arg Gln Ala Pro Gly Lys Gly Leu Glu Trp Val Ser Thr
            35                  40                  45

Ile Tyr Glu Thr Asp Gly Ser Tyr Tyr Ala Asp Ser Val Lys Gly
        50                  55                  60

Arg Phe Thr Ile Ser Arg Asp Asn Ser Lys Asn Thr Leu Tyr Leu Gln
 65                  70                  75                  80

Met Asn Ser Leu Arg Ala Glu Asp Thr Ala Val Tyr Tyr Cys Ala Arg
                 85                  90                  95

Ala Asn Phe Tyr Ser Glu Gln Pro Phe Gln Phe Trp Gly Gln Gly Thr
            100                 105                 110

Leu Val Thr Val Ser Ser
```

115

<210> SEQ ID NO 13
<211> LENGTH: 182
<212> TYPE: PRT
<213> ORGANISM: Artificial sequence
<220> FEATURE:
<223> OTHER INFORMATION: Synthesized

<400> SEQUENCE: 13

Met Lys Val Leu Gln Glu Pro Thr Cys Val Ser Asp Tyr Met Ser Ile
1               5                   10                  15

Ser Thr Cys Glu Trp Lys Met Asn Gly Pro Thr Asn Cys Ser Thr Glu
            20                  25                  30

Leu Arg Leu Leu Tyr Gln Leu Val Phe Leu Leu Ser Glu Ala His Thr
        35                  40                  45

Cys Ile Pro Glu Asn Asn Gly Gly Ala Gly Cys Val Cys His Leu Leu
    50                  55                  60

Met Asp Asp Val Val Ser Ala Asp Asn Tyr Thr Leu Asp Leu Trp Ala
65                  70                  75                  80

Gly Gln Gln Leu Leu Trp Lys Gly Ser Phe Lys Pro Ser Glu His Val
                85                  90                  95

Lys Pro Arg Ala Pro Gly Asn Leu Thr Val His Thr Asn Val Ser Asp
            100                 105                 110

Thr Leu Leu Leu Thr Trp Ser Asn Pro Tyr Pro Asp Asn Tyr Leu
        115                 120                 125

Tyr Asn His Leu Thr Tyr Ala Val Asn Ile Trp Ser Glu Asn Asp Pro
130                 135                 140

Ala Asp Phe Arg Ile Tyr Asn Val Thr Tyr Leu Glu Pro Ser Leu Arg
145                 150                 155                 160

Ile Ala Ala Ser Thr Leu Lys Ser Gly Ile Ser Tyr Arg Ala Arg Val
                165                 170                 175

Arg Ala Trp Ala Gln Cys
            180

<210> SEQ ID NO 14
<211> LENGTH: 240
<212> TYPE: PRT
<213> ORGANISM: Artificial sequence
<220> FEATURE:
<223> OTHER INFORMATION: Synthesized

<400> SEQUENCE: 14

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Ser Leu Leu Phe Asp Tyr Trp Gly Gln Gly Thr Leu
            100                 105                 110

```
Val Thr Val Ser Arg Gly Gly Ser Gly Gly Gly Ser Gly Gly
            115                 120                 125

Gly Gly Ser Ser Ser Glu Leu Thr Gln Asp Pro Ala Val Ser Val Ala
130                 135                 140

Leu Gly Gln Thr Val Arg Ile Thr Cys Gln Gly Asp Ser Leu Arg Ser
145                 150                 155                 160

Tyr Tyr Ala Ser Trp Tyr Gln Gln Lys Pro Gly Gln Ala Pro Val Leu
                165                 170                 175

Val Ile Tyr Gly Lys Asn Asn Arg Pro Ser Gly Ile Pro Asp Arg Phe
            180                 185                 190

Ser Gly Ser Ser Ser Gly Asn Thr Ala Ser Leu Thr Ile Thr Gly Ala
        195                 200                 205

Gln Ala Glu Asp Glu Ala Asp Tyr Tyr Cys Asn Ser Arg Asp Ser Ser
    210                 215                 220

Gly Asn His Val Val Phe Gly Gly Gly Thr Lys Leu Thr Val Gly Gly
225                 230                 235                 240
```

<210> SEQ ID NO 15
<211> LENGTH: 249
<212> TYPE: PRT
<213> ORGANISM: Artificial sequence
<220> FEATURE:
<223> OTHER INFORMATION: Synthesized

<400> SEQUENCE: 15

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Thr Ser Arg Gly Leu Glu
        35                  40                  45

Trp Leu Gly Arg Thr Tyr Tyr Arg Ser Lys Trp Tyr Asn Asp Tyr Ala
50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
            85                  90                  95

Tyr Tyr Cys Ala Arg Glu Val Thr Gly Asp Leu Glu Asp Ala Phe Asp
        100                 105                 110

Ile Trp Gly Gln Gly Thr Met Val Thr Val Ser Ser Gly Ser Thr Ser
    115                 120                 125

Gly Ser Gly Lys Pro Gly Ser Gly Glu Gly Ser Thr Lys Gly Asp Ile
130                 135                 140

Gln Met Thr Gln Ser Pro Ser Ser Leu Ser Ala Ser Val Gly Asp Arg
145                 150                 155                 160

Val Thr Ile Thr Cys Arg Ala Ser Gln Thr Ile Trp Ser Tyr Leu Asn
            165                 170                 175

Trp Tyr Gln Gln Arg Pro Gly Lys Ala Pro Asn Leu Leu Ile Tyr Ala
        180                 185                 190

Ala Ser Ser Leu Gln Ser Gly Val Pro Ser Arg Phe Ser Gly Arg Gly
    195                 200                 205

Ser Gly Thr Asp Phe Thr Leu Thr Ile Ser Ser Leu Gln Ala Glu Asp
    210                 215                 220

Phe Ala Thr Tyr Tyr Cys Gln Gln Ser Tyr Ser Ile Pro Gln Thr Phe
225                 230                 235                 240
```

```
Gly Gln Gly Thr Lys Leu Glu Ile Lys
                245
```

<210> SEQ ID NO 16
<211> LENGTH: 129
<212> TYPE: PRT
<213> ORGANISM: Artificial sequence
<220> FEATURE:
<223> OTHER INFORMATION: Synthesized

<400> SEQUENCE: 16

```
His Lys Cys Asp Ile Thr Leu Gln Glu Ile Ile Lys Thr Leu Asn Ser
1               5                   10                  15
Leu Thr Glu Gln Lys Thr Leu Cys Thr Glu Leu Thr Val Thr Asp Ile
            20                  25                  30
Phe Ala Ala Ser Lys Asn Thr Thr Glu Lys Glu Thr Phe Cys Arg Ala
        35                  40                  45
Ala Thr Val Leu Arg Gln Phe Tyr Ser His His Glu Lys Asp Thr Arg
    50                  55                  60
Cys Leu Gly Ala Thr Ala Gln Gln Phe His Arg His Lys Gln Leu Ile
65                  70                  75                  80
Arg Leu Leu Lys Arg Leu Asp Arg Asn Leu Trp Gly Leu Ala Gly Leu
                85                  90                  95
Asn Ser Cys Pro Val Lys Glu Ala Asn Gln Ser Thr Leu Glu Asn Phe
            100                 105                 110
Leu Glu Arg Leu Lys Thr Ile Met Arg Glu Lys Tyr Ser Lys Cys Ser
        115                 120                 125
Ser
```

<210> SEQ ID NO 17
<211> LENGTH: 464
<212> TYPE: PRT
<213> ORGANISM: Artificial sequence
<220> FEATURE:
<223> OTHER INFORMATION: Synthesized

<400> SEQUENCE: 17

```
Asp Val Gln Leu Gln Ala Ser Gly Gly Gly Leu Val Gln Pro Gly Gly
1               5                   10                  15
Ser Leu Arg Leu Ser Cys Ala Ala Ser Gly Arg Thr Phe Asn Val Asp
            20                  25                  30
Ala Met Ala Trp Phe Arg Gln Thr Arg Gly Lys Glu Arg Glu Phe Val
        35                  40                  45
Ala Ala Ile Ser Arg Ser Gly Gly Ser Thr Tyr Tyr Ala Asp Ser Val
    50                  55                  60
Lys Gly Arg Phe Ser Ile Ser Lys Asp Asn Ala Lys Asn Thr Met Tyr
65                  70                  75                  80
Leu Gln Met Asn Ser Leu Lys Pro Glu Asp Thr Ala Ile Tyr Tyr Cys
                85                  90                  95
Ala Ala Ala Ile Tyr Trp Arg Gly Ser Tyr Tyr Thr Glu Gly Asn Tyr
            100                 105                 110
Asp Tyr Trp Gly Gln Arg Thr Gln Val Thr Val Ser Ser Gly Gly Gly
        115                 120                 125
Gly Ser Ile Thr Cys Pro Pro Met Ser Val Glu His Ala Asp Ile
    130                 135                 140
Trp Val Lys Ser Tyr Ser Leu Tyr Ser Arg Glu Arg Tyr Ile Cys Asn
145                 150                 155                 160
```

-continued

```
Ser Gly Phe Lys Arg Lys Ala Gly Thr Ser Leu Thr Glu Cys Val
            165                 170                 175

Leu Asn Lys Ala Thr Asn Val Ala His Trp Thr Thr Pro Ser Leu Lys
        180                 185                 190

Cys Ile Arg Asp Pro Ala Leu Val His Gln Ser Gly Ser Gly Gly
        195                 200                 205

Gly Gly Ser Gly Gly Gly Ser Gly Gly Gly Ser Leu Gln Asp Ile
        210                 215                 220

Gln Met Thr Gln Ser Pro Ser Ser Leu Ser Ala Ser Val Gly Asp Arg
225                 230                 235                 240

Val Thr Ile Thr Cys Arg Ala Ser Gln Asp Ile Arg Asn Tyr Leu Asn
                245                 250                 255

Trp Tyr Gln Gln Lys Pro Gly Lys Ala Pro Lys Leu Leu Ile Tyr Tyr
            260                 265                 270

Thr Ser Arg Leu Glu Ser Gly Val Pro Ser Arg Phe Ser Gly Ser Gly
        275                 280                 285

Ser Gly Thr Asp Tyr Thr Leu Thr Ile Ser Ser Leu Gln Pro Glu Asp
        290                 295                 300

Phe Ala Thr Tyr Tyr Cys Gln Gln Gly Asn Thr Leu Pro Trp Thr Phe
305                 310                 315                 320

Gly Gln Gly Thr Lys Val Glu Ile Lys Gly Gly Gly Ser Gly Gly
                325                 330                 335

Gly Gly Ser Gly Gly Gly Ser Glu Val Gln Leu Val Glu Ser Gly
        340                 345                 350

Gly Gly Leu Val Gln Pro Gly Gly Ser Leu Arg Leu Ser Cys Ala Ala
        355                 360                 365

Ser Gly Tyr Ser Phe Thr Gly Tyr Thr Met Asn Trp Val Arg Gln Ala
        370                 375                 380

Pro Gly Lys Gly Leu Glu Trp Val Ala Leu Ile Asn Pro Tyr Lys Gly
385                 390                 395                 400

Val Ser Thr Tyr Asn Gln Lys Phe Lys Asp Arg Phe Thr Ile Ser Val
                405                 410                 415

Asp Lys Ser Lys Asn Thr Ala Tyr Leu Gln Met Asn Ser Leu Arg Ala
            420                 425                 430

Glu Asp Thr Ala Val Tyr Tyr Cys Ala Arg Ser Gly Tyr Tyr Gly Asp
        435                 440                 445

Ser Asp Trp Tyr Phe Asp Val Trp Gly Gln Gly Thr Leu Val Thr Val
        450                 455                 460
```

<210> SEQ ID NO 18
<211> LENGTH: 244
<212> TYPE: PRT
<213> ORGANISM: Artificial sequence
<220> FEATURE:
<223> OTHER INFORMATION: Synthesized

<400> SEQUENCE: 18

```
Asp Val Gln Leu Gln Ala Ser Gly Gly Gly Leu Val Gln Pro Gly Gly
1               5                   10                  15

Ser Leu Arg Leu Ser Cys Ala Ala Ser Gly Arg Thr Phe Asn Val Asp
            20                  25                  30

Ala Met Ala Trp Phe Arg Gln Thr Arg Gly Lys Glu Arg Glu Phe Val
        35                  40                  45

Ala Ala Ile Ser Arg Ser Gly Gly Ser Thr Tyr Tyr Ala Asp Ser Val
    50                  55                  60
```

Lys Gly Arg Phe Ser Ile Ser Lys Asp Asn Ala Lys Asn Thr Met Tyr
65                  70                  75                  80

Leu Gln Met Asn Ser Leu Lys Pro Glu Asp Thr Ala Ile Tyr Tyr Cys
            85                  90                  95

Ala Ala Ala Ile Tyr Trp Arg Gly Ser Tyr Tyr Thr Glu Gly Asn Tyr
        100                 105                 110

Asp Tyr Trp Gly Gln Arg Thr Gln Val Thr Val Ser Ser Gly Gly Gly
        115                 120                 125

Gly Ser Asn Trp Val Asn Val Ile Ser Asp Leu Lys Lys Ile Glu Asp
    130                 135                 140

Leu Ile Gln Ser Met His Ile Asp Ala Thr Leu Tyr Thr Glu Ser Asp
145                 150                 155                 160

Val His Pro Ser Cys Lys Val Thr Ala Met Lys Cys Phe Leu Leu Glu
                165                 170                 175

Leu Gln Val Ile Ser Leu Glu Ser Gly Asp Ala Ser Ile His Asp Thr
            180                 185                 190

Val Glu Asn Leu Ile Ile Leu Ala Asn Asn Ser Leu Ser Ser Asn Gly
        195                 200                 205

Asn Val Thr Glu Ser Gly Cys Lys Glu Cys Glu Glu Leu Glu Lys Lys
    210                 215                 220

Asn Ile Lys Glu Phe Leu Gln Ser Phe Val His Ile Val Gln Met Phe
225                 230                 235                 240

Ile Asn Thr Ser

<210> SEQ ID NO 19
<211> LENGTH: 456
<212> TYPE: PRT
<213> ORGANISM: Artificial sequence
<220> FEATURE:
<223> OTHER INFORMATION: Synthesized

<400> SEQUENCE: 19

Asp Val Gln Leu Gln Ala Ser Gly Gly Gly Leu Val Gln Ala Gly Asp
1               5                   10                  15

Ser Leu Arg Leu Ser Cys Ala Ala Ser Gly Arg Thr Phe Ser Thr Tyr
            20                  25                  30

Asn Met Gly Trp Phe Arg Gln Ala Pro Gly Lys Asp Arg Glu Phe Val
        35                  40                  45

Ala Ala Ile Met Trp Ser Gly Gly Ser Thr Tyr Tyr Ala Asp Ser Val
    50                  55                  60

Lys Gly Arg Phe Thr Ile Ser Lys Asp Asn Ala Lys Asn Thr Val Tyr
65                  70                  75                  80

Leu Gln Met Asn Ser Leu Lys Pro Glu Asp Thr Ala Val Tyr Phe Cys
            85                  90                  95

Trp Ser Thr Asp Asp Tyr Gly Val Asp Ser Trp Gly Gln Gly Thr Gln
        100                 105                 110

Val Thr Val Ser Ser Gly Gly Gly Gly Ser Ile Thr Cys Pro Pro Pro
    115                 120                 125

Met Ser Val Glu His Ala Asp Ile Trp Val Lys Ser Tyr Ser Leu Tyr
130                 135                 140

Ser Arg Glu Arg Tyr Ile Cys Asn Ser Gly Phe Lys Arg Lys Ala Gly
145                 150                 155                 160

Thr Ser Ser Leu Thr Glu Cys Val Leu Asn Lys Ala Thr Asn Val Ala
                165                 170                 175

His Trp Thr Thr Pro Ser Leu Lys Cys Ile Arg Asp Pro Ala Leu Val

His Gln Ser Gly Gly Ser Gly Gly Gly Ser Gly Gly Gly Ser Gly
               180                 185                 190

Gly Gly Gly Ser Leu Gln Asp Ile Gln Met Thr Gln Ser Pro Ser Ser
        195                 200                 205

Leu Ser Ala Ser Val Gly Asp Arg Val Thr Ile Thr Cys Arg Ala Ser
225                 230                 235                 240

Gln Asp Ile Arg Asn Tyr Leu Asn Trp Tyr Gln Gln Lys Pro Gly Lys
                245                 250                 255

Ala Pro Lys Leu Leu Ile Tyr Tyr Thr Ser Arg Leu Glu Ser Gly Val
            260                 265                 270

Pro Ser Arg Phe Ser Gly Ser Gly Ser Gly Thr Asp Tyr Thr Leu Thr
        275                 280                 285

Ile Ser Ser Leu Gln Pro Glu Asp Phe Ala Thr Tyr Tyr Cys Gln Gln
    290                 295                 300

Gly Asn Thr Leu Pro Trp Thr Phe Gly Gln Gly Thr Lys Val Glu Ile
305                 310                 315                 320

Lys Gly Gly Gly Gly Ser Gly Gly Gly Ser Gly Gly Gly Ser
                325                 330                 335

Glu Val Gln Leu Val Glu Ser Gly Gly Leu Val Gln Pro Gly Gly
            340                 345                 350

Ser Leu Arg Leu Ser Cys Ala Ala Ser Gly Tyr Ser Phe Thr Gly Tyr
        355                 360                 365

Thr Met Asn Trp Val Arg Gln Ala Pro Gly Lys Gly Leu Glu Trp Val
    370                 375                 380

Ala Leu Ile Asn Pro Tyr Lys Gly Val Ser Thr Tyr Asn Gln Lys Phe
385                 390                 395                 400

Lys Asp Arg Phe Thr Ile Ser Val Asp Lys Ser Lys Asn Thr Ala Tyr
                405                 410                 415

Leu Gln Met Asn Ser Leu Arg Ala Glu Asp Thr Ala Val Tyr Tyr Cys
            420                 425                 430

Ala Arg Ser Gly Tyr Tyr Gly Asp Ser Asp Trp Tyr Phe Asp Val Trp
        435                 440                 445

Gly Gln Gly Thr Leu Val Thr Val
    450                 455

<210> SEQ ID NO 20
<211> LENGTH: 368
<212> TYPE: PRT
<213> ORGANISM: Artificial sequence
<220> FEATURE:
<223> OTHER INFORMATION: Synthesized

<400> SEQUENCE: 20

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Thr Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val 85                  90                  95
Tyr Tyr Cys Ala Arg Glu Val Thr Gly Asp Leu Glu Asp Ala Phe Asp
                100                 105                 110

Ile Trp Gly Gln Gly Thr Met Val Thr Val Ser Ser Gly Ser Thr Ser
            115                 120                 125

Gly Ser Gly Lys Pro Gly Ser Gly Glu Gly Ser Thr Lys Gly Asp Ile
        130                 135                 140

Gln Met Thr Gln Ser Pro Ser Ser Leu Ser Ala Ser Val Gly Asp Arg
145                 150                 155                 160

Val Thr Ile Thr Cys Arg Ala Ser Gln Thr Ile Trp Ser Tyr Leu Asn
                165                 170                 175

Trp Tyr Gln Gln Arg Pro Gly Lys Ala Pro Asn Leu Leu Ile Tyr Ala
                180                 185                 190

Ala Ser Ser Leu Gln Ser Gly Val Pro Ser Arg Phe Ser Gly Arg Gly
                195                 200                 205

Ser Gly Thr Asp Phe Thr Leu Thr Ile Ser Ser Leu Gln Ala Glu Asp
        210                 215                 220

Phe Ala Thr Tyr Tyr Cys Gln Gln Ser Tyr Ser Ile Pro Gln Thr Phe
225                 230                 235                 240

Gly Gln Gly Thr Lys Leu Glu Ile Lys Gly Gly Gly Ser Asn Trp
                245                 250                 255

Val Asn Val Ile Ser Asp Leu Lys Lys Ile Glu Asp Leu Ile Gln Ser
                260                 265                 270

Met His Ile Asp Ala Thr Leu Tyr Thr Glu Ser Asp Val His Pro Ser
                275                 280                 285

Cys Lys Val Thr Ala Met Lys Cys Phe Leu Leu Glu Leu Gln Val Ile
                290                 295                 300

Ser Leu Glu Ser Gly Asp Ala Ser Ile His Asp Thr Val Glu Asn Leu
305                 310                 315                 320

Ile Ile Leu Ala Asn Asn Ser Leu Ser Ser Asn Gly Asn Val Thr Glu
                325                 330                 335

Ser Gly Cys Lys Glu Cys Glu Glu Leu Glu Lys Lys Asn Ile Lys Glu
                340                 345                 350

Phe Leu Gln Ser Phe Val His Ile Val Gln Met Phe Ile Asn Thr Ser
                355                 360                 365

<210> SEQ ID NO 21
<211> LENGTH: 457
<212> TYPE: PRT
<213> ORGANISM: Artificial sequence
<220> FEATURE:
<223> OTHER INFORMATION: Synthesized

<400> SEQUENCE: 21

Gln Leu Leu Glu Ser Gly Gly Gly Leu Val Gln Pro Gly Gly Ser Leu
1               5                   10                  15

Arg Leu Ser Cys Ala Ala Ser Gly Tyr Arg Ile Ser Ser Asp Asp Met
                20                  25                  30

Ser Trp Val Arg Gln Ala Pro Gly Lys Gly Leu Glu Trp Val Ser Thr
            35                  40                  45

Ile Tyr Glu Thr Asp Gly Ser Thr Tyr Tyr Ala Asp Ser Val Lys Gly
        50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg

Ala Asn Phe Tyr Ser Glu Gln Pro Phe Gln Phe Trp Gly Gln Gly Thr
                85                  90                  95                 100

Leu Val Thr Val Ser Ser Gly Gly Gly Ser Ile Thr Cys Pro Pro
        115                 120                 125

Pro Met Ser Val Glu His Ala Asp Ile Trp Val Lys Ser Tyr Ser Leu
    130                 135                 140

Tyr Ser Arg Glu Arg Tyr Ile Cys Asn Ser Gly Phe Lys Arg Lys Ala
145                 150                 155                 160

Gly Thr Ser Ser Leu Thr Glu Cys Val Leu Asn Lys Ala Thr Asn Val
            165                 170                 175

Ala His Trp Thr Thr Pro Ser Leu Lys Cys Ile Arg Asp Pro Ala Leu
        180                 185                 190

Val His Gln Ser Gly Gly Ser Gly Gly Gly Ser Gly Gly Gly Ser
    195                 200                 205

Gly Gly Gly Gly Ser Leu Gln Asp Ile Gln Met Thr Gln Ser Pro Ser
210                 215                 220

Ser Leu Ser Ala Ser Val Gly Asp Arg Val Thr Ile Thr Cys Arg Ala
225                 230                 235                 240

Ser Gln Asp Ile Arg Asn Tyr Leu Asn Trp Tyr Gln Gln Lys Pro Gly
                245                 250                 255

Lys Ala Pro Lys Leu Leu Ile Tyr Tyr Thr Ser Arg Leu Glu Ser Gly
            260                 265                 270

Val Pro Ser Arg Phe Ser Gly Ser Gly Ser Gly Thr Asp Tyr Thr Leu
        275                 280                 285

Thr Ile Ser Ser Leu Gln Pro Glu Asp Phe Ala Thr Tyr Tyr Cys Gln
    290                 295                 300

Gln Gly Asn Thr Leu Pro Trp Thr Phe Gly Gln Gly Thr Lys Val Glu
305                 310                 315                 320

Ile Lys Gly Gly Gly Gly Ser Gly Gly Gly Gly Ser Gly Gly Gly Gly
                325                 330                 335

Ser Glu Val Gln Leu Val Glu Ser Gly Gly Gly Leu Val Gln Pro Gly
            340                 345                 350

Gly Ser Leu Arg Leu Ser Cys Ala Ala Ser Gly Tyr Ser Phe Thr Gly
        355                 360                 365

Tyr Thr Met Asn Trp Val Arg Gln Ala Pro Gly Lys Gly Leu Glu Trp
    370                 375                 380

Val Ala Leu Ile Asn Pro Tyr Lys Gly Val Ser Thr Tyr Asn Gln Lys
385                 390                 395                 400

Phe Lys Asp Arg Phe Thr Ile Ser Val Asp Lys Ser Lys Asn Thr Ala
                405                 410                 415

Tyr Leu Gln Met Asn Ser Leu Arg Ala Glu Asp Thr Ala Val Tyr Tyr
            420                 425                 430

Cys Ala Arg Ser Gly Tyr Tyr Gly Asp Ser Asp Trp Tyr Phe Asp Val
        435                 440                 445

Trp Gly Gln Gly Thr Leu Val Thr Val
    450                 455

<210> SEQ ID NO 22
<211> LENGTH: 455
<212> TYPE: PRT
<213> ORGANISM: Artificial sequence
<220> FEATURE:
<223> OTHER INFORMATION: Synthesized

<400> SEQUENCE: 22

```
Gln Leu Leu Glu Ser Gly Gly Leu Val Gln Pro Gly Gly Ser Leu
1               5                  10                  15

Arg Leu Ser Cys Ala Ala Ser Gly Tyr Arg Ile Ser Ser Asp Asp Met
            20                  25                  30

Ser Trp Val Arg Gln Ala Pro Gly Lys Gly Leu Glu Trp Val Ser Thr
        35                  40                  45

Ile Tyr Glu Thr Asp Gly Ser Thr Tyr Ala Asp Ser Val Lys Gly
50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Ala Asn Phe Tyr Ser Glu Gln Pro Phe Gln Trp Gly Gln Gly Thr
            100                 105                 110

Leu Val Thr Val Ser Ser Gly Gly Gly Ser Ile Thr Cys Pro Pro
        115                 120                 125

Pro Met Ser Val Glu His Ala Asp Ile Trp Val Lys Ser Tyr Ser Leu
130                 135                 140

Tyr Ser Arg Glu Arg Tyr Ile Cys Asn Ser Gly Phe Lys Arg Lys Ala
145                 150                 155                 160

Gly Thr Ser Ser Leu Thr Glu Cys Val Leu Asn Lys Ala Thr Asn Val
                165                 170                 175

Ala His Trp Thr Thr Pro Ser Leu Lys Cys Ile Arg Asp Pro Ala Leu
            180                 185                 190

Val His Gln Ser Gly Ser Gly Gly Gly Ser Gly Gly Gly Ser
        195                 200                 205

Gly Gly Gly Gly Ser Leu Gln Glu Val Gln Leu Val Glu Ser Gly Gly
210                 215                 220

Gly Val Val Arg Pro Gly Gly Ser Leu Arg Leu Ser Cys Ala Ala Ser
225                 230                 235                 240

Gly Phe Thr Phe Asp Asp Tyr Gly Met Ser Trp Val Arg Gln Ala Pro
                245                 250                 255

Gly Lys Gly Leu Glu Trp Val Ser Gly Ile Asn Trp Asn Gly Gly Ser
            260                 265                 270

Thr Gly Tyr Ala Asp Ser Val Lys Gly Arg Phe Thr Ile Ser Arg Asp
        275                 280                 285

Asn Ala Lys Asn Ser Leu Tyr Leu Gln Met Asn Ser Leu Arg Ala Glu
290                 295                 300

Asp Thr Ala Val Tyr Tyr Cys Ala Arg Gly Arg Ser Leu Leu Phe Asp
305                 310                 315                 320

Tyr Trp Gly Gln Gly Thr Leu Val Thr Val Ser Arg Gly Gly Gly Ser
                325                 330                 335

Gly Gly Gly Gly Ser Gly Gly Gly Ser Ser Glu Leu Thr Gln
            340                 345                 350

Asp Pro Ala Val Ser Val Ala Leu Gly Gln Thr Val Arg Ile Thr Cys
        355                 360                 365

Gln Gly Asp Ser Leu Arg Ser Tyr Tyr Ala Ser Trp Tyr Gln Gln Lys
370                 375                 380

Pro Gly Gln Ala Pro Val Leu Val Ile Tyr Gly Lys Asn Asn Arg Pro
385                 390                 395                 400

Ser Gly Ile Pro Asp Arg Phe Ser Gly Ser Ser Gly Asn Thr Ala
                405                 410                 415
```

```
Ser Leu Thr Ile Thr Gly Ala Gln Ala Glu Asp Glu Ala Asp Tyr Tyr
            420                 425                 430

Cys Asn Ser Arg Asp Ser Ser Gly Asn His Val Val Phe Gly Gly Gly
            435                 440                 445

Thr Lys Leu Thr Val Gly Gly
            450             455

<210> SEQ ID NO 23
<211> LENGTH: 567
<212> TYPE: PRT
<213> ORGANISM: Artificial sequence
<220> FEATURE:
<223> OTHER INFORMATION: Synthesized

<400> SEQUENCE: 23

Gln Leu Leu Glu Ser Gly Gly Gly Leu Val Gln Pro Gly Gly Ser Leu
1               5                   10                  15

Arg Leu Ser Cys Ala Ala Ser Gly Tyr Arg Ile Ser Ser Asp Asp Met
            20                  25                  30

Ser Trp Val Arg Gln Ala Pro Gly Lys Gly Leu Glu Trp Val Ser Thr
            35                  40                  45

Ile Tyr Glu Thr Asp Gly Ser Thr Tyr Tyr Ala Asp Ser Val Lys Gly
            50                  55                  60

Arg Phe Thr Ile Ser Arg Asp Asn Ser Lys Asn Thr Leu Tyr Leu Gln
65              70                  75                  80

Met Asn Ser Leu Arg Ala Glu Asp Thr Ala Val Tyr Tyr Cys Ala Arg
            85                  90                  95

Ala Asn Phe Tyr Ser Glu Gln Pro Phe Gln Phe Trp Gly Gln Gly Thr
            100                 105                 110

Leu Val Thr Val Ser Ser Gly Gly Gly Ser Met Lys Val Leu Gln
            115                 120                 125

Glu Pro Thr Cys Val Ser Asp Tyr Met Ser Ile Ser Thr Cys Glu Trp
            130                 135                 140

Lys Met Asn Gly Pro Thr Asn Cys Ser Thr Glu Leu Arg Leu Leu Tyr
145             150                 155                 160

Gln Leu Val Phe Leu Leu Ser Glu Ala His Thr Cys Ile Pro Glu Asn
            165                 170                 175

Asn Gly Gly Ala Gly Cys Val Cys His Leu Leu Met Asp Asp Val Val
            180                 185                 190

Ser Ala Asp Asn Tyr Thr Leu Asp Leu Trp Ala Gly Gln Gln Leu Leu
            195                 200                 205

Trp Lys Gly Ser Phe Lys Pro Ser Glu His Val Lys Pro Arg Ala Pro
            210                 215                 220

Gly Asn Leu Thr Val His Thr Asn Val Ser Asp Thr Leu Leu Leu Thr
225             230                 235                 240

Trp Ser Asn Pro Tyr Pro Pro Asp Asn Tyr Leu Tyr Asn His Leu Thr
            245                 250                 255

Tyr Ala Val Asn Ile Trp Ser Glu Asn Asp Pro Ala Asp Phe Arg Ile
            260                 265                 270

Tyr Asn Val Thr Tyr Leu Glu Pro Ser Leu Arg Ile Ala Ala Ser Thr
            275                 280                 285

Leu Lys Ser Gly Ile Ser Tyr Arg Ala Arg Val Arg Ala Trp Ala Gln
            290                 295                 300

Cys Ser Gly Gly Ser Gly Gly Gly Ser Gly Gly Gly Ser Gly Gly
305             310                 315                 320
```

Gly Gly Ser Leu Gln Asp Ile Gln Met Thr Gln Ser Pro Ser Ser Leu
              325                 330                 335

Ser Ala Ser Val Gly Asp Arg Val Thr Ile Thr Cys Arg Ala Ser Gln
              340                 345                 350

Asp Ile Arg Asn Tyr Leu Asn Trp Tyr Gln Gln Lys Pro Gly Lys Ala
              355                 360                 365

Pro Lys Leu Leu Ile Tyr Tyr Thr Ser Arg Leu Glu Ser Gly Val Pro
        370                 375                 380

Ser Arg Phe Ser Gly Ser Gly Ser Gly Thr Asp Tyr Thr Leu Thr Ile
385                 390                 395                 400

Ser Ser Leu Gln Pro Glu Asp Phe Ala Thr Tyr Tyr Cys Gln Gln Gly
              405                 410                 415

Asn Thr Leu Pro Trp Thr Phe Gly Gln Gly Thr Lys Val Glu Ile Lys
              420                 425                 430

Gly Gly Gly Gly Ser Gly Gly Gly Ser Gly Gly Gly Gly Ser Glu
              435                 440                 445

Val Gln Leu Val Glu Ser Gly Gly Leu Val Gln Pro Gly Gly Ser
        450                 455                 460

Leu Arg Leu Ser Cys Ala Ala Ser Gly Tyr Ser Phe Thr Gly Tyr Thr
465                 470                 475                 480

Met Asn Trp Val Arg Gln Ala Pro Gly Lys Gly Leu Glu Trp Val Ala
              485                 490                 495

Leu Ile Asn Pro Tyr Lys Gly Val Ser Thr Tyr Asn Gln Lys Phe Lys
              500                 505                 510

Asp Arg Phe Thr Ile Ser Val Asp Lys Ser Lys Asn Thr Ala Tyr Leu
              515                 520                 525

Gln Met Asn Ser Leu Arg Ala Glu Asp Thr Ala Val Tyr Tyr Cys Ala
        530                 535                 540

Arg Ser Gly Tyr Tyr Gly Asp Ser Asp Trp Tyr Phe Asp Val Trp Gly
545                 550                 555                 560

Gln Gly Thr Leu Val Thr Val
              565

```
<210> SEQ ID NO 24
<211> LENGTH: 284
<212> TYPE: PRT
<213> ORGANISM: Artificial sequence
<220> FEATURE:
<223> OTHER INFORMATION: Synthesized

<400> SEQUENCE: 24
```

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
              20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
              85                  90                  95

Asp Ser Gly Thr Tyr Leu Cys Gly Ala Ile Ser Leu Ala Pro Lys Ala
              100                 105                 110

```
Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
130                 135                 140

Gln Phe Gln Thr Leu Val Gly Gly Gly Ser His Lys Cys Asp Ile
145                 150                 155                 160

Thr Leu Gln Glu Ile Ile Lys Thr Leu Asn Ser Leu Thr Glu Gln Lys
                165                 170                 175

Thr Leu Cys Thr Glu Leu Thr Val Thr Asp Ile Phe Ala Ala Ser Lys
            180                 185                 190

Asn Thr Thr Glu Lys Glu Thr Phe Cys Arg Ala Ala Thr Val Leu Arg
            195                 200                 205

Gln Phe Tyr Ser His His Glu Lys Asp Thr Arg Cys Leu Gly Ala Thr
            210                 215                 220

Ala Gln Gln Phe His Arg His Lys Gln Leu Ile Arg Leu Leu Lys Arg
225                 230                 235                 240

Leu Asp Arg Asn Leu Trp Gly Leu Ala Gly Leu Asn Ser Cys Pro Val
                245                 250                 255

Lys Glu Ala Asn Gln Ser Thr Leu Glu Asn Phe Leu Glu Arg Leu Lys
            260                 265                 270

Thr Ile Met Arg Glu Lys Tyr Ser Lys Cys Ser Ser
            275                 280

<210> SEQ ID NO 25
<211> LENGTH: 365
<212> TYPE: PRT
<213> ORGANISM: Artificial sequence
<220> FEATURE:
<223> OTHER INFORMATION: Synthesized

<400> SEQUENCE: 25

Gln Leu Leu Glu Ser Gly Gly Gly Leu Val Gln Pro Gly Gly Ser Leu
1               5                   10                  15

Arg Leu Ser Cys Ala Ala Ser Gly Tyr Arg Ile Ser Ser Asp Asp Met
            20                  25                  30

Ser Trp Val Arg Gln Ala Pro Gly Lys Gly Leu Glu Trp Val Ser Thr
        35                  40                  45

Ile Tyr Glu Thr Asp Gly Ser Thr Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Ala Asn Phe Tyr Ser Glu Gln Pro Phe Gln Phe Trp Gly Gln Gly Thr
            100                 105                 110

Leu Val Thr Val Ser Ser Gly Gly Gly Gly Ser Ile Thr Cys Pro Pro
            115                 120                 125

Pro Met Ser Val Glu His Ala Asp Ile Trp Val Lys Ser Tyr Ser Leu
        130                 135                 140

Tyr Ser Arg Glu Arg Tyr Ile Cys Asn Ser Gly Phe Lys Arg Lys Ala
145                 150                 155                 160

Gly Thr Ser Ser Leu Thr Glu Cys Val Leu Asn Lys Ala Thr Asn Val
                165                 170                 175

Ala His Trp Thr Thr Pro Ser Leu Lys Cys Ile Arg Asp Pro Ala Leu
            180                 185                 190
```

```
Val His Gln Ser Gly Gly Ser Gly Gly Gly Ser Gly Gly Gly Ser
        195                 200                 205

Gly Gly Gly Ser Leu Gln Pro Gly Trp Phe Leu Asp Ser Pro Asp
210                 215                 220

Arg Pro Trp Asn Pro Pro Thr Phe Ser Pro Ala Leu Leu Val Thr
225                 230                 235                 240

Glu Gly Asp Asn Ala Thr Phe Thr Cys Ser Phe Ser Asn Thr Ser Glu
                245                 250                 255

Ser Phe Val Leu Asn Trp Tyr Arg Met Ser Pro Ser Asn Gln Thr Asp
                260                 265                 270

Lys Leu Ala Ala Phe Pro Glu Asp Arg Ser Gln Pro Gly Gln Asp Cys
                275                 280                 285

Arg Phe Arg Val Thr Gln Leu Pro Asn Gly Arg Asp Phe His Met Ser
290                 295                 300

Val Val Arg Ala Arg Arg Asn Asp Ser Gly Thr Tyr Leu Cys Gly Ala
305                 310                 315                 320

Ile Ser Leu Ala Pro Lys Ala Gln Ile Lys Glu Ser Leu Arg Ala Glu
                325                 330                 335

Leu Arg Val Thr Glu Arg Arg Ala Glu Val Pro Thr Ala His Pro Ser
                340                 345                 350

Pro Ser Pro Arg Pro Ala Gly Gln Phe Gln Thr Leu Val
                355                 360                 365

<210> SEQ ID NO 26
<211> LENGTH: 361
<212> TYPE: PRT
<213> ORGANISM: Artificial sequence
<220> FEATURE:
<223> OTHER INFORMATION: Synthesized

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys Gly Gly Gly Gly Ser
                100                 105                 110

Gly Gly Gly Gly Ser Gly Gly Gly Ser Glu Val Gln Leu Val Glu
            115                 120                 125

Ser Gly Gly Gly Leu Val Gln Pro Gly Gly Ser Leu Arg Leu Ser Cys
130                 135                 140

Ala Ala Ser Gly Tyr Ser Phe Thr Gly Tyr Thr Met Asn Trp Val Arg
145                 150                 155                 160

Gln Ala Pro Gly Lys Gly Leu Glu Trp Val Ala Leu Ile Asn Pro Tyr
                165                 170                 175

Lys Gly Val Ser Thr Tyr Asn Gln Lys Phe Lys Asp Arg Phe Thr Ile
                180                 185                 190
```

```
Ser Val Asp Lys Ser Lys Asn Thr Ala Tyr Leu Gln Met Asn Ser Leu
            195                 200                 205

Arg Ala Glu Asp Thr Ala Val Tyr Tyr Cys Ala Arg Ser Gly Tyr Tyr
    210                 215                 220

Gly Asp Ser Asp Trp Tyr Phe Asp Val Trp Gly Gln Gly Thr Leu Val
225                 230                 235                 240

Thr Val Gly Gly Gly Ser Asn Trp Val Asn Val Ile Ser Asp Leu
                245                 250                 255

Lys Lys Ile Glu Asp Leu Ile Gln Ser Met His Ile Asp Ala Thr Leu
            260                 265                 270

Tyr Thr Glu Ser Asp Val His Pro Ser Cys Lys Val Thr Ala Met Lys
            275                 280                 285

Cys Phe Leu Leu Glu Leu Gln Val Ile Ser Leu Glu Ser Gly Asp Ala
    290                 295                 300

Ser Ile His Asp Thr Val Glu Asn Leu Ile Ile Leu Ala Asn Asn Ser
305                 310                 315                 320

Leu Ser Ser Asn Gly Asn Val Thr Glu Ser Gly Cys Lys Glu Cys Glu
                325                 330                 335

Glu Leu Glu Lys Lys Asn Ile Lys Glu Phe Leu Gln Ser Phe Val His
            340                 345                 350

Ile Val Gln Met Phe Ile Asn Thr Ser
            355                 360

<210> SEQ ID NO 27
<211> LENGTH: 489
<212> TYPE: PRT
<213> ORGANISM: Artificial sequence
<220> FEATURE:
<223> OTHER INFORMATION: Synthesized

<400> SEQUENCE: 27

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Gly Gly Gly Ser Ile Thr Cys Pro Pro
145                 150                 155                 160

Pro Met Ser Val Glu His Ala Asp Ile Trp Val Lys Ser Tyr Ser Leu
                165                 170                 175

Tyr Ser Arg Glu Arg Tyr Ile Cys Asn Ser Gly Phe Lys Arg Lys Ala
            180                 185                 190
```

Gly Thr Ser Ser Leu Thr Glu Cys Val Leu Asn Lys Ala Thr Asn Val
                195                 200                 205

Ala His Trp Thr Thr Pro Ser Leu Lys Cys Ile Arg Asp Pro Ala Leu
210                 215                 220

Val His Gln Ser Gly Ser Gly Gly Gly Ser Gly Gly Gly Ser
225                 230                 235                 240

Gly Gly Gly Gly Ser Leu Gln Asp Ile Gln Met Thr Gln Ser Pro Ser
                245                 250                 255

Ser Leu Ser Ala Ser Val Gly Asp Arg Val Thr Ile Thr Cys Arg Ala
                260                 265                 270

Ser Gln Asp Ile Arg Asn Tyr Leu Asn Trp Tyr Gln Gln Lys Pro Gly
                275                 280                 285

Lys Ala Pro Lys Leu Leu Ile Tyr Tyr Thr Ser Arg Leu Glu Ser Gly
                290                 295                 300

Val Pro Ser Arg Phe Ser Gly Ser Gly Ser Gly Thr Asp Tyr Thr Leu
305                 310                 315                 320

Thr Ile Ser Ser Leu Gln Pro Glu Asp Phe Ala Thr Tyr Tyr Cys Gln
                325                 330                 335

Gln Gly Asn Thr Leu Pro Trp Thr Phe Gly Gln Gly Thr Lys Val Glu
                340                 345                 350

Ile Lys Gly Gly Gly Gly Ser Gly Gly Gly Gly Ser Gly Gly Gly Gly
                355                 360                 365

Ser Glu Val Gln Leu Val Glu Ser Gly Gly Gly Leu Val Gln Pro Gly
                370                 375                 380

Gly Ser Leu Arg Leu Ser Cys Ala Ala Ser Gly Tyr Ser Phe Thr Gly
385                 390                 395                 400

Tyr Thr Met Asn Trp Val Arg Gln Ala Pro Gly Lys Gly Leu Glu Trp
                405                 410                 415

Val Ala Leu Ile Asn Pro Tyr Lys Gly Val Ser Thr Tyr Asn Gln Lys
                420                 425                 430

Phe Lys Asp Arg Phe Thr Ile Ser Val Asp Lys Ser Lys Asn Thr Ala
                435                 440                 445

Tyr Leu Gln Met Asn Ser Leu Arg Ala Glu Asp Thr Ala Val Tyr Tyr
                450                 455                 460

Cys Ala Arg Ser Gly Tyr Tyr Gly Asp Ser Asp Trp Tyr Phe Asp Val
465                 470                 475                 480

Trp Gly Gln Gly Thr Leu Val Thr Val
                485

<210> SEQ ID NO 28
<211> LENGTH: 237
<212> TYPE: PRT
<213> ORGANISM: Artificial sequence
<220> FEATURE:
<223> OTHER INFORMATION: Synthesized

<400> SEQUENCE: 28

Gln Leu Leu Glu Ser Gly Gly Gly Leu Val Gln Pro Gly Gly Ser Leu
1               5                   10                  15

Arg Leu Ser Cys Ala Ala Ser Gly Tyr Arg Ile Ser Ser Asp Asp Met
                20                  25                  30

Ser Trp Val Arg Gln Ala Pro Gly Lys Gly Leu Glu Trp Val Ser Thr
            35                  40                  45

Ile Tyr Glu Thr Asp Gly Ser Thr Tyr Tyr Ala Asp Ser Val Lys Gly
        50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Ala Asn Phe Tyr Ser Glu Gln Pro Phe Gln Phe Trp Gly Gln Gly Thr
            100                 105                 110

Leu Val Thr Val Ser Ser Gly Gly Gly Ser Asn Trp Val Asn Val
        115                 120                 125

Ile Ser Asp Leu Lys Lys Ile Glu Asp Leu Ile Gln Ser Met His Ile
130                 135                 140

Asp Ala Thr Leu Tyr Thr Glu Ser Asp Val His Pro Ser Cys Lys Val
145                 150                 155                 160

Thr Ala Met Lys Cys Phe Leu Leu Glu Leu Gln Val Ile Ser Leu Glu
                165                 170                 175

Ser Gly Asp Ala Ser Ile His Asp Thr Val Glu Asn Leu Ile Ile Leu
            180                 185                 190

Ala Asn Asn Ser Leu Ser Ser Asn Gly Asn Val Thr Glu Ser Gly Cys
        195                 200                 205

Lys Glu Cys Glu Glu Leu Glu Lys Lys Asn Ile Lys Glu Phe Leu Gln
210                 215                 220

Ser Phe Val His Ile Val Gln Met Phe Ile Asn Thr Ser
225                 230                 235

<210> SEQ ID NO 29
<211> LENGTH: 457
<212> TYPE: PRT
<213> ORGANISM: Artificial sequence
<220> FEATURE:
<223> OTHER INFORMATION: Synthesized

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Ser Glu Val Gln Leu Val Glu
        115                 120                 125

Ser Gly Gly Gly Leu Val Gln Pro Gly Gly Ser Leu Arg Leu Ser Cys
130                 135                 140

Ala Ala Ser Gly Tyr Ser Phe Thr Gly Tyr Thr Met Asn Trp Val Arg
145                 150                 155                 160

Gln Ala Pro Gly Lys Gly Leu Glu Trp Val Ala Leu Ile Asn Pro Tyr
                165                 170                 175

Lys Gly Val Ser Thr Tyr Asn Gln Lys Phe Lys Asp Arg Phe Thr Ile
            180                 185                 190

```
Ser Val Asp Lys Ser Lys Asn Thr Ala Tyr Leu Gln Met Asn Ser Leu
        195                 200                 205

Arg Ala Glu Asp Thr Ala Val Tyr Tyr Cys Ala Arg Ser Gly Tyr Tyr
    210                 215                 220

Gly Asp Ser Asp Trp Tyr Phe Asp Val Trp Gly Gln Gly Thr Leu Val
225                 230                 235                 240

Thr Val Gly Gly Gly Gly Ser Ile Thr Cys Pro Pro Met Ser Val
                245                 250                 255

Glu His Ala Asp Ile Trp Val Lys Ser Tyr Ser Leu Tyr Ser Arg Glu
                260                 265                 270

Arg Tyr Ile Cys Asn Ser Gly Phe Lys Arg Lys Ala Gly Thr Ser Ser
            275                 280                 285

Leu Thr Glu Cys Val Leu Asn Lys Ala Thr Asn Val Ala His Trp Thr
        290                 295                 300

Thr Pro Ser Leu Lys Cys Ile Arg Asp Pro Ala Leu Val His Gln Ser
305                 310                 315                 320

Gly Gly Ser Gly Gly Gly Ser Gly Gly Ser Gly Gly Gly Gly
                325                 330                 335

Ser Leu Gln Gln Leu Leu Glu Ser Gly Gly Leu Val Gln Pro Gly
                340                 345                 350

Gly Ser Leu Arg Leu Ser Cys Ala Ala Ser Gly Tyr Arg Ile Ser Ser
        355                 360                 365

Asp Asp Met Ser Trp Val Arg Gln Ala Pro Gly Lys Gly Leu Glu Trp
    370                 375                 380

Val Ser Thr Ile Tyr Glu Thr Asp Gly Ser Thr Tyr Tyr Ala Asp Ser
385                 390                 395                 400

Val Lys Gly Arg Phe Thr Ile Ser Arg Asp Asn Ser Lys Asn Thr Leu
                405                 410                 415

Tyr Leu Gln Met Asn Ser Leu Arg Ala Glu Asp Thr Ala Val Tyr Tyr
            420                 425                 430

Cys Ala Arg Ala Asn Phe Tyr Ser Glu Gln Pro Phe Gln Phe Trp Gly
        435                 440                 445

Gln Gly Thr Leu Val Thr Val Ser Ser
    450                 455

<210> SEQ ID NO 30
<211> LENGTH: 499
<212> TYPE: PRT
<213> ORGANISM: Artificial sequence
<220> FEATURE:
<223> OTHER INFORMATION: Synthesized

<400> SEQUENCE: 30

Gln Leu Leu Glu Ser Gly Gly Gly Leu Val Gln Pro Gly Gly Ser Leu
1               5                   10                  15

Arg Leu Ser Cys Ala Ala Ser Gly Tyr Arg Ile Ser Ser Asp Asp Met
            20                  25                  30

Ser Trp Val Arg Gln Ala Pro Gly Lys Gly Leu Glu Trp Val Ser Thr
        35                  40                  45

Ile Tyr Glu Thr Asp Gly Ser Thr Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95
```

```
Ala Asn Phe Tyr Ser Glu Gln Pro Phe Gln Phe Trp Gly Gln Gly Thr
            100                 105                 110

Leu Val Thr Val Ser Ser Gly Gly Gly Gly Ser Asn Trp Val Asn Val
            115                 120                 125

Ile Ser Asp Leu Lys Lys Ile Glu Asp Leu Ile Gln Ser Met His Ile
            130                 135                 140

Asp Ala Thr Leu Tyr Thr Glu Ser Asp Val His Pro Ser Cys Lys Val
145                 150                 155                 160

Thr Ala Met Lys Cys Phe Leu Leu Glu Leu Gln Val Ile Ser Leu Glu
                165                 170                 175

Ser Gly Asp Ala Ser Ile His Asp Thr Val Glu Asn Leu Ile Ile Leu
            180                 185                 190

Ala Asn Asn Ser Leu Ser Ser Asn Gly Asn Val Thr Glu Ser Gly Cys
            195                 200                 205

Lys Glu Cys Glu Glu Leu Glu Lys Lys Asn Ile Lys Glu Phe Leu Gln
            210                 215                 220

Ser Phe Val His Ile Val Gln Met Phe Ile Asn Thr Ser Ser Gly Gly
225                 230                 235                 240

Ser Gly Gly Gly Ser Gly Gly Gly Ser Gly Gly Gly Gly Ser Leu
                245                 250                 255

Gln Asp Ile Gln Met Thr Gln Ser Pro Ser Ser Leu Ser Ala Ser Val
            260                 265                 270

Gly Asp Arg Val Thr Ile Thr Cys Arg Ala Ser Gln Asp Ile Arg Asn
            275                 280                 285

Tyr Leu Asn Trp Tyr Gln Gln Lys Pro Gly Lys Ala Pro Lys Leu Leu
            290                 295                 300

Ile Tyr Tyr Thr Ser Arg Leu Glu Ser Gly Val Pro Ser Arg Phe Ser
305                 310                 315                 320

Gly Ser Gly Ser Gly Thr Asp Tyr Thr Leu Thr Ile Ser Ser Leu Gln
                325                 330                 335

Pro Glu Asp Phe Ala Thr Tyr Tyr Cys Gln Gln Gly Asn Thr Leu Pro
            340                 345                 350

Trp Thr Phe Gly Gln Gly Thr Lys Val Glu Ile Lys Gly Gly Gly Gly
            355                 360                 365

Ser Gly Gly Gly Gly Ser Gly Gly Gly Gly Ser Glu Val Gln Leu Val
            370                 375                 380

Glu Ser Gly Gly Gly Leu Val Gln Pro Gly Gly Ser Leu Arg Leu Ser
385                 390                 395                 400

Cys Ala Ala Ser Gly Tyr Ser Phe Thr Gly Tyr Thr Met Asn Trp Val
                405                 410                 415

Arg Gln Ala Pro Gly Lys Gly Leu Glu Trp Val Ala Leu Ile Asn Pro
            420                 425                 430

Tyr Lys Gly Val Ser Thr Tyr Asn Gln Lys Phe Lys Asp Arg Phe Thr
            435                 440                 445

Ile Ser Val Asp Lys Ser Lys Asn Thr Ala Tyr Leu Gln Met Asn Ser
            450                 455                 460

Leu Arg Ala Glu Asp Thr Ala Val Tyr Tyr Cys Ala Arg Ser Gly Tyr
465                 470                 475                 480

Tyr Gly Asp Ser Asp Trp Tyr Phe Asp Val Trp Gly Gln Gly Thr Leu
                485                 490                 495

Val Thr Val
```

<210> SEQ ID NO 31
<211> LENGTH: 158
<212> TYPE: PRT
<213> ORGANISM: Artificial sequence
<220> FEATURE:
<223> OTHER INFORMATION: Synthesized

<400> SEQUENCE: 31

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Gly Gly Gly Ser Ile Thr Cys
145                 150                 155
```

<210> SEQ ID NO 32
<211> LENGTH: 1671
<212> TYPE: DNA
<213> ORGANISM: Artificial sequence
<220> FEATURE:
<223> OTHER INFORMATION: Synthesized

<400> SEQUENCE: 32

```
atgccacctc ctcgcctcct cttcttcctc ctcttcctca cccccatgga agtcaggccc      60
gaggaacctc tagtggtgaa ggtggaagag ggagataacg ctgtgctgca gtgcctcaag     120
gggacctcag atggccccac tcagcagctg acctggtctc gggagtcccc gcttaaaccc     180
ttcttaaaac tcagcctggg gctgccaggc ctgggaatcc acatgaggcc cctggccatc     240
tggcttttca tcttcaacgt ctctcaacag atgggggggct ctacctgtg ccagccgggg    300
ccccctctg agaaggcctg gcagcctggc tggacagtca atgtgaggg cagcggggag      360
ctgttccggt ggaatgtttc ggacctaggt ggcctgggct gtggcctgaa gaacaggtcc    420
tcagagggcc ccagctcccc ttccgggaag ctcatgagcc caagctgta tgtgtgggcc     480
aaagaccgcc tgagatctg ggaggggag cctccgtgtc tcccaccgag ggacagcctg      540
aaccagagcc tcagccagga cctcaccatg gcccctggct ccacactctg gctgtcctgt    600
ggggtacccc ctgactctgt gtccagggcc ccctctcct ggacccatgt gcaccccaag     660
gggcctaagt cattgctgag cctagagctg aaggacgatc gccggccag agatatgtgg     720
gtaatggaga cgggtctgtt gttgccccgg gccacagctc aagacgctgg aaagtattat    780
tgtcaccgtg caaacctgac catgtcattc caccctggaga tcactgctcg gccagtacta    840
tggcactggc tgctgaggac tggtggctgg aaggtctcag ctgtgacttt ggcttatctg     900
```

```
atcttctgcc tgtgttccct tgtgggcatt cttcatcttc aaagagccct ggtcctgagg    960
aggaaaagaa agcgaatgac tgaccccacc aggagattct tcaaagtgac gcctccccca   1020
ggaagcgggc cccagaacca gtacgggaac gtgctgtctc tccccacacc cacctcaggc   1080
ctcggacgcg cccagcgttg gccgcaggc ctgggggca ctgccccgtc ttatggaaac    1140
ccgagcagcg acgtccaggc ggatggagcc ttggggtccc ggagcccgcc gggagtgggc   1200
ccagaagaag aggaagggga gggctatgag gaacctgaca gtgaggagga ctccgagttc   1260
tatgagaacg actccaacct tgggcaggac cagctctccc aggatggcag cggctacgag   1320
aaccctgagg atgagcccct gggtcctgag gatgaagact ccttctccaa cgctgagtct   1380
tatgagaacg aggatgaaga gctgacccag ccggtcgcca ggacaatgga cttcctgagc   1440
cctcatgggt cagcctggga ccccagccgg gaagcaacct ccctgggtc ccagtcctat    1500
gaggatatga gaggaatcct gtatgcagcc ccccagctcc gctccattcg gggccagcct   1560
ggacccaatc atgaggaaga tgcagactct tatgagaaca tggataatcc cgatgggcca   1620
gacccagcct ggggaggagg gggccgcatg ggcacctgga gcaccaggtg a            1671
```

<210> SEQ ID NO 33
<211> LENGTH: 1773
<212> TYPE: DNA
<213> ORGANISM: Artificial sequence
<220> FEATURE:
<223> OTHER INFORMATION: Synthesized

<400> SEQUENCE: 33

```
atggaagatg ccaaaaacat taagaagggc ccagcgccat tctacccact cgaagacggg     60
accgccggcg agcagctgca caaagccatg aagcgctacg ccctggtgcc cggcaccatc    120
gcctttaccg acgcacatat cgaggtggac attacctacg ccgagtactt cgagatgagc    180
gttcggctgg cagaagctat gaagcgctat gggctgaata caaaccatcg gatcgtggtg    240
tgcagcgaga atagcttgca gttcttcatg cccgtgttgg gtgccctgtt catcggtgtg    300
gctgtggccc cagctaacga catctacaac gagcgcgagc tgctgaacag catgggcatc    360
agccagccca ccgtcgtatt cgtgagcaag aaagggctgc aaaagatcct caacgtgcaa    420
aagaagctac cgatcataca aaagatcatc atcatggata gcaagaccga ctaccagggc    480
ttccaaagca tgtacacctt cgtgacttcc catttgccac ccggcttcaa cgagtacgac    540
ttcgtgcccg agagcttcga ccgggacaaa accatcgccc tgatcatgaa cagtagtggc    600
agtaccggat tgcccaaggg cgtagcccta ccgcaccgca ccgcttgtgt ccgattcagt    660
catgcccgcg accccatctt cggcaaccag atcatccccg acaccgctat cctcagcgtg    720
gtgccatttc accacggctt cggcatgttc accacgctgg gctacttgat ctgcggcttt    780
cgggtcgtgc tcatgtaccg cttcgaggag gagctattct tgcgcagctt gcaagactat    840
aagattcaat ctgccctgct ggtgcccaca ctatttagct tcttcgctaa gagcactctc    900
atcgacaagt acgacctaag caacttgcac gagatcgcca gcggcggggc gccgctcagc    960
aaggaggtag gtgaggccgt ggccaaacgc ttccacctac caggcatccg ccagggctac   1020
ggcctgacag aaacaaccag cgccattctg atcacccccg aaggggacga caagcctggc   1080
gcagtaggca aggtggtgcc cttcttcgag gctaaggtgg tggacttgga caccggtaag   1140
acactgggtg tgaaccagcg cggcgagctg tgcgtccgtg gccccatgat catgagcggc   1200
tacgttaaca acccc gaggc tacaaacgct ctcatcgaca aggacggctg gctgcacagc   1260
ggcgacatcg cctactggga cgaggacgag cacttcttca tcgtggaccg gctgaagagc   1320
```

```
ctgatcaaat acaagggcta ccaggtagcc ccagccgaac tggagagcat cctgctgcaa    1380
caccccaaca tcttcgacgc cggggtcgcc ggcctgcccg acgacgatgc cggcgagctg    1440
cccgccgcag tcgtcgtgct ggaacacggt aaaaccatga ccgagaagga gatcgtggac    1500
tatgtggcca gccaggttac aaccgccaag aagctgcgcg tggtgttgt gttcgtggac     1560 gaggtgccta aaggactgac cggcaagttg gacgcccgca agatccgcga gattctcatt    1620
aaggccaaga agggcggcaa gatcgccgtg aattctcacg gcttccctcc cgaggtggag    1680
gagcaggccg ccggcaccct gcccatgagc tgcgcccagg agagcggcat ggatagacac    1740
cctgctgctt gcgccagcgc caggatcaac gtc                                 1773
```

<210> SEQ ID NO 34
<211> LENGTH: 2544
<212> TYPE: DNA
<213> ORGANISM: Artificial sequence
<220> FEATURE:
<223> OTHER INFORMATION: Synthesized

<400> SEQUENCE: 34

```
atgcatctcc tcggccctg gctcctgctc ctggttctag aatacttggc tttctctgac     60
tcaagtaaat gggttttga gcaccctgaa accctctacg cctgggaggg ggcctgcgtc    120
tggatcccct gcacctacag agccctagat ggtgacctgg aaagcttcat cctgttccac    180
aatcctgagt ataacaagaa cacctcgaag tttgatggga caagactcta tgaaagcaca   240
aaggatggga aggttccttc tgagcagaaa agggtgcaat tcctgggaga caagaataag    300
aactgcacac tgagtatcca cccggtgcac ctcaatgaca gtggtcagct ggggctgagg    360
atggagtcca agactgagaa atggatgaa cgaatacacc tcaatgtctc tgaaaggcct    420
tttccacctc atatccagct ccctccagaa attcaagagt cccaggaagt cactctgacc   480
tgcttgctga atttctcctg ctatgggtat ccgatccaat gcagtggct cctagagggg    540 gttccaatga ggcaggctgc tgtcacctcg acctccttga ccatcaagtc tgtcttcacc    600
cggagcgagc tcaagttctc cccacagtgg agtcaccatg ggaagattgt gacctgccag    660
cttcaggatg cagatgggaa gttcctctcc aatgacacgg tgcagctgaa cgtgaagcac    720
accccgaagt tggagatcaa ggtcactccc agtgatgcca gtgaggga gggggactct    780 gtgaccatga cctgcgaggt cagcagcagc aacccggagt acacgacggt atcctggctc    840
aaggatggga cctcgctgaa gaagcagaat acattcacgc taaacctgcg cgaagtgacc    900
aaggaccaga gtgggaagta ctgctgtcag gtctccaatg acgtgggccc gggaaggtcg    960
gaagaagtgt cctgcaagt gcagtatgcc ccggaacctt ccacggttca gatcctccac   1020
tcaccggctg tggagggaag tcaagtcgag tttcttttgca tgtcactggc caatcctctt   1080
ccaacaaatt acacgtggta ccacaatggg aaagaaatgc agggaaggac agaggagaaa    1140
gtccacatcc caaagatcct ccctggcac gctgggactt attcctgtgt ggcagaaaac    1200
attcttggta ctggacagag gggccgggga gctgagctgg atgtccagta tcctcccaag    1260
aaggtgacca cagtgattca aaaccccatg ccgattcgag aaggagacac agtgacccctt   1320 tcctgtaact acaattccag taaccccgagt gttacccggt atgaatggaa accccatggc    1380
gcctgggagg agccatcgct tgggtgctg aagatccaaa acgttggctg ggacaacaca    1440
accatcgcct gcgcagcttg taatagttgg tgctcgtggg cctcccctgt cgccctgaat    1500
gtccagtatg ccccccgaga cgtgagggtc cggaaaatca gccccttc cgagattcac    1560
```

```
tctggaaact cggtcagcct ccaatgtgac ttctcaagca gccaccccaa agaagtccag      1620
ttcttctggg agaaaaatgg caggcttctg gggaaagaaa gccagctgaa ttttgactcc      1680
atctccccag aagatgctgg gagttacagc tgctgggtga acaactccat aggacagaca      1740
gcgtccaagg cctggacact tgaagtgctg tatgcaccca ggaggctgcg tgtgtccatg      1800
agcccggggg accaagtgat ggaggggaag agtgcaaccc tgacctgtga gagcgacgcc      1860
aaccctcccg tctcccacta cacctggttt gactggaata accaaagcct cccctaccac      1920
agccagaagc tgagattgga gccggtgaag gtccagcact cgggtgccta ctggtgccag      1980
gggaccaaca gtgtgggcaa gggccgttcg cctctcagca ccctcaccgt ctactatagc      2040
ccggagacca tcggcaggcg agtggctgtg ggactcgggt cctgcctcgc catcctcatc      2100
ctggcaatct gtgggctcaa gctccagcga cgttggaaga ggacacagag ccagcagggg      2160
cttcaggaga attccagcgg ccagagcttc tttgtgagga ataaaaaggt tagaagggcc      2220
cccctctctg aaggccccca ctccctggga tgctacaatc caatgatgga agatggcatt      2280
agctacacca ccctgcgctt tcccgagatg aacataccac gaactggaga tgcagagtcc      2340
tcagagatgc agagacctcc cccggactgc gatgacacgg tcacttattc agcattgcac      2400
aagcgccaag tgggcgacta tgagaacgtc attccagatt ttccagaaga tgaggggatt      2460
cattactcag agctgatcca gtttggggtc ggggagcggc ctcaggcaca agaaaatgtg      2520
gactatgtga tcctcaaaca ttga                                            2544

<210> SEQ ID NO 35
<211> LENGTH: 1446
<212> TYPE: DNA
<213> ORGANISM: Artificial sequence
<220> FEATURE:
<223> OTHER INFORMATION: Synthesized

<400> SEQUENCE: 35
atgaagtggg taacctttat ttcccttctt tttctcttta gctcggctta ttccgacgtc        60
caactgcaag ctagcggggg aggcttggtg cagcctgggg gtctctgag actctcctgt       120 gcagcctctg gacgcacctt caatgtcgat gctatggctt ggttccgcca gactcgcggg       180
aaggagcgtg agttttgtagc agctattagc cggagtggtg gtagcacgta ctatgcagac       240
tccgtgaagg gccgattcag catctccaaa gacaacgcca aaaacacgat gtatctgcaa       300
atgaacagcc tcaaacctga ggacacggcc atttattact gtgcagctgc aatctactgg       360
cgtggtagtt actacactga aggcaactat gactactggg gccagaggac ccaggtcacc       420
gtctcgagcg gcggcggcgg atctatcacg tgccctcccc ccatgtccgt ggaacacgca       480
gacatctggg tcaagagcta cagccttgtac tccaggagc ggtacatttg taactctggt       540
ttcaagcgta aagccggcac gtccagcctg acggagtgcg tgttgaacaa ggccacgaat       600
gtcgcccact ggacaacccc cagtctcaaa tgcattagag accctgccct ggttcaccaa       660
agcggcggct ccgggggagg tggatccgga ggtggctccg gtggaggcgg aagcctgcag       720
gatatccaga tgacccagtc cccgagctcc ctgtccgcta gcgtgggcga tagggtcacc       780
atcacctgtc gtgccagtca ggacatccgt aattatctca ctggtatca acagaaacca       840 ggaaaagctc cgaaactact gatttactat acctcccgcc tggagtctgg agtcccttct       900
cgcttctctg gttctggttc tgggacggat tacactctga ccatcagcag tctgcaaccg       960
gaggacttcg caacttatta ctgtcagcaa ggtaatactc tgccgtggac gttcggacag      1020
ggcaccaagg tggagatcaa aggtggaggc ggttcaggcg gaggtggctc tggcggtggc      1080
```

| | |
|---|---|
| ggatcggagg ttcagctggt ggagtctggc ggtggcctgg tgcagccagg gggctcactc | 1140 |
| cgtttgtcct gtgcagcttc tggctactcc tttaccggct acactatgaa ctgggtgcgt | 1200 |
| caggccccag gtaagggcct ggaatgggtt gcactgatta atccttataa aggtgtttcc | 1260 |
| acctataacc agaaattcaa ggatcgtttc acgatatccg tagataaatc caaaaacaca | 1320 |
| gcctacctgc aaatgaacag cctgcgtgct gaggacactg ccgtctatta ttgtgctaga | 1380 |
| agcggatact acggcgatag cgactggtat tttgacgtct ggggtcaagg aaccctggtc | 1440 |
| accgtc | 1446 |

<210> SEQ ID NO 36
<211> LENGTH: 732
<212> TYPE: DNA
<213> ORGANISM: Artificial sequence
<220> FEATURE:
<223> OTHER INFORMATION: Synthesized

<400> SEQUENCE: 36

| | |
|---|---|
| gacgtccaac tgcaagctag cggggggaggc ttggtgcagc ctggggggtc tctgagactc | 60 |
| tcctgtgcag cctctggacg caccttcaat gtcgatgcta tggcttggtt ccgccagact | 120 |
| cgcgggaagg agcgtgagtt tgtagcagct attagccgga gtggtggtag cacgtactat | 180 |
| gcagactccg tgaagggccg attcagcatc tccaaagaca acgccaaaaa cacgatgtat | 240 |
| ctgcaaatga acagcctcaa acctgaggac acggccattt attactgtgc agctgcaatc | 300 |
| tactggcgtg gtagttacta cactgaaggc aactatgact actggggcca ggagacccag | 360 |
| gtcaccgtct cctcaggcgg aggaggctcc aactgggtga acgtcatctc cgacctcaag | 420 |
| aagatcgagg acctgatcca gagcatgcac atcgacgcca ccctgtatac cgagagcgac | 480 |
| gtgcacccct cctgtaaagt gaccgccatg aagtgcttcc tgctggagct gcaggtgatc | 540 |
| agcctggaga gcggcgacgc cagcatccat gacaccgtgg agaacctgat catcctggcc | 600 |
| aataacagcc tgagctccaa cggcaacgtg accgagagcg gctgcaagga atgcgaggag | 660 |
| ctggagaaga gaacattaa ggagttcctg cagagcttcg tccacatcgt gcagatgttc | 720 |
| attaacacct cc | 732 |

<210> SEQ ID NO 37
<211> LENGTH: 1422
<212> TYPE: DNA
<213> ORGANISM: Artificial sequence
<220> FEATURE:
<223> OTHER INFORMATION: Synthesized

<400> SEQUENCE: 37

| | |
|---|---|
| atgaagtggg taacctttat ttccttctct tttctcttta gctcggctta ttccgatgtg | 60 |
| cagctgcaag ctagcggagg cggcctggtg caagctggag actccctgag gctgagctgc | 120 |
| gccgctagcg gaaggacctt cagcacctac aacatgggct ggttcaggca ggcccccgga | 180 |
| aaggacaggg agttcgtggc cgccattatg tggtccggcg gcagcaccta ctatgccgac | 240 |
| agcgtgaagg gcaggttcac aatctccaag gacaacgcca gaacaccgt gtacctgcag | 300 |
| atgaactccc tgaagcccga ggatacagcc gtgtacttct gctggagcac cgatgattac | 360 |
| ggagtcgaca gctggggcca gggaacccag gtgaccgtga gctccggcgg cggcggatct | 420 |
| atcacgtgcc ctccccccat gtccgtggaa cacgcagaca tctgggtcaa gagctacagc | 480 |
| ttgtactcca gggagcggta catttgtaac tctggtttca gcgtaaagc cggcacgtcc | 540 |

```
agcctgacgg agtgcgtgtt gaacaaggcc acgaatgtcg cccactggac aaccccccagt    600 ctcaaatgca ttagagaccc tgccctggtt caccaaagcg gcggctccgg gggaggtgga    660
tccggaggtg gctccggtgg aggcggaagc ctgcaggata tccagatgac ccagtccccg    720
agctccctgt ccgctagcgt gggcgatagg gtcaccatca cctgtcgtgc cagtcaggac    780
atccgtaatt atctcaactg gtatcaacag aaaccaggaa aagctccgaa actactgatt    840
tactatacct cccgcctgga gtctggagtc ccttctcgct tctctggttc tggttctggg    900
acggattaca ctctgaccat cagcagtctg caaccggagg acttcgcaac ttattactgt    960
cagcaaggta atactctgcc gtggacgttc ggacagggca ccaaggtgga gatcaaaggt   1020
ggaggcggtt caggcggagg tggctctggc ggtggcggat cggaggttca gctggtggag   1080
tctggcggtg cctggtgca gccaggggc tcactccgtt tgtcctgtgc agcttctggc   1140 tactcctttta ccggctacac tatgaactgg gtgcgtcagg ccccaggtaa gggcctggaa   1200
tgggttgcac tgattaatcc ttataaaggt gtttccacct ataaccagaa attcaaggat   1260
cgtttcacga tatccgtaga taaatccaaa aacacagcct acctgcaaat gaacagcctg   1320
cgtgctgagg acactgccgt ctattattgt gctagaagcg gatactacgg cgatagcgac   1380
tggtattttg acgtctgggg tcaaggaacc ctggtcaccg tc                       1422

<210> SEQ ID NO 38
<211> LENGTH: 1104
<212> TYPE: DNA
<213> ORGANISM: Artificial sequence
<220> FEATURE:
<223> OTHER INFORMATION: Synthesized

<400> SEQUENCE: 38
caggtgcagc tgcaacagag cggccctgga ctggtgaagc ccagccagac actgagcctc     60
acctgcgcca ttagcggcga cagcgtgagc tccaattccg ccgcctggaa ttggatcaga    120
cagagcacaa gcaggggcct ggagtggctg gcaggaccta ctacaggag caagtggtac    180 aacgactacg ccgtgtccgt gaagagcagg atcacaatca accccgacac cagcaagaac    240
cagttcagcc tgcagctcaa cagcgtcacc cccgaagaca ccgccgtgta ctactgcgcc    300
agagaggtga ccggcgacct ggaggacgcc ttcgacatct ggggccaagg caccatggtg    360
accgtgagct ccggctccac aagcggaagc ggcaaacctg gctccggcga gggttctacc    420
aaaggcgaca tccagatgac ccagagccct cctcccctga gcgccagcgt gggcgataga    480
gtgacaatta cctgcagggc cagccagacc atctggagct acctgaactg gtaccagcag    540
aggcccggaa aggcccccaa cctgctgatc tacgccgctt ccagcctgca gagcggcgtg    600
cctagcaggt tctccggcag aggcagcggc accgatttca ccctgacaat cagcagcctg    660
caggccgaag attttgccac ctactactgc cagcagagct acagcatccc ccagaccttc    720
ggccagggca ccaaactgga gatcaagggc ggaggaggct ccaactgggt gaacgtcatc    780
tccgacctca agaagatcga ggacctgatc cagagcatgc acatcgacgc caccctgtat    840
accgagagcg acgtgcaccc ctcctgtaaa gtgaccgcca tgaagtgctt cctgctggag    900
ctgcaggtga tcagcctgga gagcggcgac gccagcatcc atgacaccgt ggagaacctg    960
atcatcctgg ccaataacag cctgagctcc aacggcaacg tgaccgagag cggctgcaag   1020
gaatgcgagg agctggagaa gaagaacatt aaggagttcc tgcagagctt cgtccacatc   1080
gtgcagatgt tcattaacac ctcc                                          1104
```

<210> SEQ ID NO 39
<211> LENGTH: 1431
<212> TYPE: DNA
<213> ORGANISM: Artificial sequence
<220> FEATURE:
<223> OTHER INFORMATION: Synthesized

<400> SEQUENCE: 39

| | |
|---|---|
| atgtacagga tgcaactcct gtcttgcatt gcactaagtc ttgcacttgt cacgaattct | 60 |
| cagctgttgg agtctggggg aggcttggta cagcctgggg ggtccctgcg tctctcctgt | 120 |
| gcagcctccg gatataggat tagctctgac gatatgagct gggtccgcca ggctccaggg | 180 |
| aagggtctag agtgggtatc aaccatttat gagacagacg gtagcacata ctacgcagac | 240 |
| tccgtgaagg gccggttcac catctcccgt gacaattcca agaacacgct gtatctgcaa | 300 |
| atgaacagcc tgcgtgccga ggacaccgcg gtatattatt gcgcgagagc taattttat | 360 |
| agtgagcagc ccttccagtt ttggggtcag ggaaccctgg tcaccgtctc gagcggcggc | 420 |
| ggcggatcta tcacgtgccc tccccccatg tccgtggaac acgcagacat ctgggtcaag | 480 |
| agctacagct tgtactccag ggagcggtac atttgtaact ctggtttcaa gcgtaaagcc | 540 |
| ggcacgtcca gcctgacgga gtgcgtgttg aacaaggcca cgaatgtcgc ccactggaca | 600 |
| acccccagtc tcaaatgcat tagagaccct gccctggttc accaaagcgg cggctccggg | 660 |
| ggaggtggat ccggaggtgg ctccggtgga ggcggaagcc tgcaggatat ccagatgacc | 720 |
| cagtccccga gctccctgtc cgctagcgtg ggcgataggg tcaccatcac ctgtcgtgcc | 780 |
| agtcaggaca tccgtaatta tctcaactgg tatcaacaga aaccaggaaa agctccgaaa | 840 |
| ctactgattt actataccct ccgcctggag tctggagtcc cttctcgctt ctctggttct | 900 |
| ggttctggga cggattacac tctgaccatc agcagtctgc aaccggagga cttcgcaact | 960 |
| tattactgtc agcaaggtaa tactctgccg tggacgttcg gacagggcac caaggtggag | 1020 |
| atcaaaggtg gaggcggttc aggcggaggt ggctctggcg gtggcggatc ggaggttcag | 1080 |
| ctggtggagt ctggcggtgg cctggtgcag ccagggggct cactccgttt gtcctgtgca | 1140 |
| gcttctggct actcctttac cggctacact atgaactggg tgcgtcaggc cccaggtaag | 1200 |
| ggcctggaat gggttgcact gattaatcct tataaaggtg tttccaccta taaccagaaa | 1260 |
| ttcaaggatc gtttcacgat atccgtagat aaatccaaaa acacagccta cctgcaaatg | 1320 |
| aacagcctgc gtgctgagga cactgccgtc tattattgtg ctagaagcgg atactacggc | 1380 |
| gatagcgact ggtatttga cgtctggggt caaggaaccc tggtcaccgt c | 1431 |

<210> SEQ ID NO 40
<211> LENGTH: 1425
<212> TYPE: DNA
<213> ORGANISM: Artificial sequence
<220> FEATURE:
<223> OTHER INFORMATION: Synthesized

<400> SEQUENCE: 40

| | |
|---|---|
| atgtacagga tgcaactcct gtcttgcatt gcactaagtc ttgcacttgt cacgaattct | 60 |
| cagctgttgg agtctggggg aggcttggta cagcctgggg ggtccctgcg tctctcctgt | 120 |
| gcagcctccg gatataggat tagctctgac gatatgagct gggtccgcca ggctccaggg | 180 |
| aagggtctag agtgggtatc aaccatttat gagacagacg gtagcacata ctacgcagac | 240 |
| tccgtgaagg gccggttcac catctcccgt gacaattcca agaacacgct gtatctgcaa | 300 |
| atgaacagcc tgcgtgccga ggacaccgcg gtatattatt gcgcgagagc taattttat | 360 |

```
agtgagcagc ccttccagtt ttggggtcag ggaaccctgg tcaccgtctc gagcggcggc      420
ggcggatcta tcacgtgccc tcccccatg tccgtggaac acgcagacat ctgggtcaag       480
agctacagct tgtactccag ggagcggtac atttgtaact ctggtttcaa gcgtaaagcc      540
ggcacgtcca gcctgacgga gtgcgtgttg aacaaggcca cgaatgtcgc ccactggaca      600
accccagtc tcaaatgcat tagagaccct gccctggttc accaaagcgg cggctccggg       660
ggaggtggat ccggaggtgg ctccggtgga ggcggaagcc tgcaggaagt gcagctggtg      720
gaaagcggcg gcggcgtggt gcgtccgggc ggcagcctgc gtctgagctg cgcggcgagc      780
ggctttacct ttgatgatta tggcatgagc tgggtgcgtc aggcgccggg caaaggcctg      840
gaatgggtga gcggcattaa ctggaacggc ggcagcaccg gctatgcgga tagcgtgaaa      900
ggccgtttta ccattagccg tgataacgcg aaaaacagcc tgtatctgca gatgaacagc      960
ctgcgtgcgg aagataccgc ggtgtattat tgcgcgcgtg gccgtagcct gctgtttgat     1020
tattggggcc agggcaccct ggtgaccgtg agccgtggcg gcggcagcgg cggcggcggc     1080
agcggcggcg gcggcagcag cagcgaactg acccaggatc cggcggtgag cgtggcgctg     1140
ggccagaccg tgcgtattac ctgccagggc gatagcctgc gtagctatta tgcgagctgg     1200
tatcagcaga accgggcca gcgccggtg ctggtgattt atggcaaaaa caaccgtccg       1260
agcggcattc cggatcgttt tagcggcagc agcagcggca caccgcgag cctgaccatt      1320
accggcgcgc aggcggaaga tgaagcggat tattattgca acagccgtga tagcagcggc     1380
aaccatgtgg tgtttggcgg cggcaccaaa ctgaccgtgg gcggc                     1425
```

<210> SEQ ID NO 41
<211> LENGTH: 1761
<212> TYPE: DNA
<213> ORGANISM: Artificial sequence
<220> FEATURE:
<223> OTHER INFORMATION: Synthesized

<400> SEQUENCE: 41

```
atgtacagga tgcaactcct gtcttgcatt gcactaagtc ttgcacttgt cacgaattct       60
cagctgttgg agtctggggg aggcttggta cagcctgggg gtccctgcg tctctcctgt       120
gcagcctccg gatataggat tagctctgac gatatgagct gggtccgcca ggctccaggg      180
aagggtctag agtgggtatc aaccatttat gagacagacg gtagcacata ctacgcagac      240
tccgtgaagg gccggttcac catctcccgt gacaattcca gaacacgct gtatctgcaa       300
atgaacagcc tgcgtgccga ggacaccgcg gtatattatt gcgcgagagc taatttttat      360
agtgagcagc ccttccagtt ttggggtcag ggaaccctgg tcaccgtctc gagcggcggc      420
ggcggatcta tgaaggtctt gcaggagccc acctgcgtct ccgactacat gagcatctct      480
acttgcgagt ggaagatgaa tggtcccacc aattgcagca ccgagctccg cctgttgtac      540
cagctggttt ttctgctctc gaagcccac acgtgtatcc tgagaacaa cggaggcgcg       600
gggtgcgtgt gccacctgct catggatgac gtggtcagtg cggataacta tacactggac      660
ctgtgggctg gcagcagct gctgtggaag ggctccttca gcccagcga gcatgtgaaa       720
cccagggccc caggaaacct gacagttcac accaatgtct ccgacactct gctgctgacc     780
tggagcaacc cgtatcccc tgacaattac ctgtataatc atctcaccta tgcagtcaac      840
atttggagtg aaaacgaccc ggcagatttc agaatctata acgtgaccta cctagaaccc     900
tccctccgca tcgcagccag cacctgaag tctgggattt cctacagggc acgggtgagg      960
gcctgggctc agtgcagcgg cggctccggg ggaggtggat ccggaggtgg ctccggtgga    1020
```

```
ggcggaagcc tgcaggatat ccagatgacc cagtccccga gctccctgtc cgctagcgtg      1080
ggcgataggg tcaccatcac ctgtcgtgcc agtcaggaca tccgtaatta tctcaactgg      1140
tatcaacaga aaccaggaaa agctccgaaa ctactgattt actataccto ccgcctggag      1200 tctggagtcc cttctcgctt ctctggttct ggttctggga cggattacac tctgaccatc      1260
agcagtctgc aaccggagga cttcgcaact tattactgtc agcaaggtaa tactctgccg      1320
tggacgttcg gacagggcac caaggtggag atcaaaggtg gaggcggttc aggcggaggt      1380
ggctctggcg gtggcggatc ggaggttcag ctggtggagt ctggcggtgg cctggtgcag      1440
ccagggggct cactccgttt gtcctgtgca gcttctggct actcctttac cggctacact      1500
atgaactggg tgcgtcaggc cccaggtaag ggcctggaat gggttgcact gattaatcct      1560
tataaaggtg tttccaccta taaccagaaa ttcaaggatc gtttcacgat atccgtagat      1620
aaatccaaaa acacagccta cctgcaaatg aacagcctgc gtgctgagga cactgccgtc      1680
tattattgtg ctagaagcgg atactacggc gatagcgact ggtattttga cgtctggggt      1740
caaggaaccc tggtcaccgt c                                                1761
```

<210> SEQ ID NO 42
<211> LENGTH: 852
<212> TYPE: DNA
<213> ORGANISM: Artificial sequence
<220> FEATURE:
<223> OTHER INFORMATION: Synthesized

<400> SEQUENCE: 42

```
ccaggatggt tcttagactc cccagacagg ccctggaacc cccccacctt ctccccagcc        60
ctgctcgtgg tgaccgaagg ggacaacgcc accttcacct gcagcttctc caacacatcg      120
gagagcttcg tgctaaactg gtaccgcatg agccccagca accagacgga caagctggcc      180
gccttccccg aggaccgcag ccagcccggc caggactgcc gcttccgtgt cacacaactg      240
cccaacgggc gtgacttcca catgagcgtg gtcagggccc ggcgcaatga cagcggcacc      300
tacctctgtg gggccatctc cctggccccc aaggcgcaga tcaaagagag cctgcgggca      360
gagctcaggg tgacagagag aagggcagaa gtgcccacag cccaccccag cccctcaccc      420
aggccagccg gccagttcca aaccctggtg ggcggaggag gctcccacaa gtgcgatatc      480
accttacagg agatcatcaa aactttgaac agcctcacag agcagaagac tctgtgcacc      540
gagttgaccg taacagacat ctttgctgcc tccaagaaca caactgagaa ggaaaccttc      600
tgcagggctg cgactgtgct ccggcagttc tacagccacc atgagaagga cactcgctgc      660
ctgggtgcga ctgcacagca gttccacagg cacaagcagc tgatccgact cctgaaacgg      720
ctcgacagga acctctgggg cctggcgggc ttgaattcct gtcctgtgaa ggaagccaac      780
cagagtacgt tggaaaactt cttggaaagg ctaaagacga tcatgagaga gaaatattca      840
aagtgttcga gc                                                           852
```

<210> SEQ ID NO 43
<211> LENGTH: 1155
<212> TYPE: DNA
<213> ORGANISM: Artificial sequence
<220> FEATURE:
<223> OTHER INFORMATION: Synthesized

<400> SEQUENCE: 43

```
atgtacagga tgcaactcct gtcttgcatt gcactaagtc ttgcacttgt cacgaattct        60
```

```
cagctgttgg agtctggggg aggcttggta cagcctgggg ggtccctgcg tctctcctgt      120
gcagcctccg gatataggat tagctctgac gatatgagct gggtccgcca ggctccaggg      180
aagggtctag agtgggtatc aaccatttat gagacagacg gtagcacata ctacgcagac      240
tccgtgaagg gccggttcac catctcccgt gacaattcca agaacacgct gtatctgcaa      300
atgaacagcc tgcgtgccga ggacaccgcg gtatattatt gcgcgagagc taatttttat      360
agtgagcagc ccttccagtt ttggggtcag ggaaccctgg tcaccgtctc gagcggcggc      420
ggcggatcta tcacgtgccc tccccccatg tccgtggaac acgcagacat ctgggtcaag      480
agctacagct tgtactccag ggagcggtac atttgtaact ctggtttcaa gcgtaaagcc      540
ggcacgtcca gcctgacgga gtgcgtgttg aacaaggcca cgaatgtcgc ccactggaca      600
acccccagtc tcaaatgcat tagagaccct gccctggttc accaaagcgg cggctccggg      660
ggaggtggat ccggaggtgg ctccggtgga ggcggaagcc tgcagccagg atggttctta      720
gactccccag acaggccctg gaaccccccc accttctccc cagccctgct cgtggtgacc      780 gaagggggaca acgccaccttc cacctgcagc ttctccaaca catcggagag cttcgtgcta      840
aactggtacc gcatgagccc cagcaaccag acggacaagc tggccgcctt ccccgaggac      900
cgcagccagc ccgccaggga ctgccgcttc cgtgtcacac aactgcccaa cgggcgtgac      960
ttccacatga gcgtggtcag ggcccggcgc aatgacagcg gcacctacct ctgtggggcc     1020
atctccctgg cccccaaggc gcagatcaaa gagagcctgc gggcagagct cagggtgaca     1080
gagagaaggg cagaagtgcc cacagcccac cccagcccct cacccaggcc agccggccag     1140
ttccaaaccc tggtg                                                       1155

<210> SEQ ID NO 44
<211> LENGTH: 1083
<212> TYPE: DNA
<213> ORGANISM: Artificial sequence
<220> FEATURE:
<223> OTHER INFORMATION: Synthesized

<400> SEQUENCE: 44
gatatccaga tgacccagtc cccgagctcc ctgtccgcta gcgtgggcga tagggtcacc       60
atcacctgtc gtgccagtca ggacatccgt aattatctca actggtatca acagaaacca      120
ggaaaagctc cgaaactact gatttactat acctcccgcc tggagtctgg agtcccttct      180
cgcttctctg gttctggttc tgggacggat tacactctga ccatcagcag tctgcaaccg      240
gaggacttcg caacttatta ctgtcagcaa ggtaatactc tgccgtggac gttcggacag      300
ggcaccaagg tggagatcaa aggtggaggc ggttcaggcg gaggtggctc tggcggtggc      360
ggatcggagg ttcagctggt ggagtctggc ggtggcctgg tgcagccagg gggctcactc      420
cgtttgtcct gtgcagcttc tggctactcc tttaccggct acactatgaa ctgggtgcgt      480
caggccccag gtaagggcct ggaatgggtt gcactgatta tccttataaa aggtgtttcc      540
acctataacc agaaattcaa ggatcgtttc acgatatccg tagataaatc caaaaacaca      600
gcctacctgc aaatgaacag cctgcgtgct gaggacactg ccgtctatta ttgtgctaga      660
agcggatact acggcgatag cgactggtat tttgacgtct ggggtcaagg aaccctggtc      720
accgtcggcg gaggaggctc caactgggtg aacgtcatct ccgacctcaa gaagatcgag      780
gacctgatcc agagcatgca catcgacgcc accctgtata ccgagagcga cgtgcacccc      840
tcctgtaaag tgaccgccat gaagtgcttc ctgctggagc tgcaggtgat cagcctggag      900
agcggcgacg ccagcatcca tgacaccgtg gagaacctga tcatcctggc caataacagc      960
```

| | |
|---|---|
| ctgagctcca acggcaacgt gaccgagagc ggctgcaagg aatgcgagga gctggagaag | 1020 |
| aagaacatta aggagttcct gcagagcttc gtccacatcg tgcagatgtt cattaacacc | 1080 |
| tcc | 1083 |

<210> SEQ ID NO 45
<211> LENGTH: 1521
<212> TYPE: DNA
<213> ORGANISM: Artificial sequence
<220> FEATURE:
<223> OTHER INFORMATION: Synthesized

<400> SEQUENCE: 45

| | |
|---|---|
| atgtacagga tgcaactcct gtcttgcatt gcactaagtc ttgcacttgt cacgccagga | 60 |
| tggttcttag actccccaga caggccctgg aaccccccca ccttctcccc agccctgctc | 120 |
| gtggtgaccg aaggggacaa cgccaccttc acctgcagct tctccaacac atcggagagc | 180 |
| ttcgtgctaa actggtaccg catgagcccc agcaaccaga cggacaagct ggccgccttc | 240 |
| cccgaggacc gcagccagcc cggccaggac tgccgcttcc gtgtcacaca actgcccaac | 300 |
| gggcgtgact tccacatgag cgtggtcagg gcccggcgca atgacagcgg cacctacctc | 360 |
| tgtggggcca tctccctggc ccccaaggcg cagatcaaag agagcctgcg ggcagagctc | 420 |
| agggtgacag agagaagggc agaagtgccc acagcccacc ccagcccctc acccaggcca | 480 |
| gccggccagt ccaaacccct ggtgggcggc ggcggatcta tcacgtgccc tcccccatg | 540 |
| tccgtggaac acgcagacat ctgggtcaag agctacagct tgtactccag ggagcggtac | 600 |
| atttgtaact ctggtttcaa gcgtaaagcc ggcacgtcca gcctgacgga gtgcgtgttg | 660 |
| aacaaggcca cgaatgtcgc ccactggaca accccccagtc tcaaatgcat tagagaccct | 720 |
| gccctggttc accaaagcgg cggctccggg ggaggtggat ccggaggtgg ctccggtgga | 780 |
| ggcggaagcc tgcaggatat ccagatgacc cagtccccga ctccctgtc cgctagcgtg | 840 |
| ggcgataggg tcaccatcac ctgtcgtgcc agtcaggaca tccgtaatta tctcaactgg | 900 |
| tatcaacaga aaccaggaaa agctccgaaa ctactgattt actataccct ccgcctggag | 960 |
| tctggagtcc cttctcgctt ctctggttct ggttctggga cggattacac tctgaccatc | 1020 |
| agcagtctgc aaccggagga cttcgcaact tattactgtc agcaaggtaa tactctgccg | 1080 |
| tggacgttcg gacagggcac caaggtggag atcaaaggtg gaggcggttc aggcggaggt | 1140 |
| ggctctggcg gtggcggatc ggaggttcag ctggtggagt ctggcggtgg cctggtgcag | 1200 |
| ccagggggct cactccgttt gtcctgtgca gcttctggct actcctttac cggctacact | 1260 |
| atgaactggg tgcgtcaggc cccaggtaag ggcctggaat gggttgcact gattaatcct | 1320 |
| tataaaggtg tttccaccta taccagaaa ttcaaggatc gtttcacgat atccgtagat | 1380 |
| aaatccaaaa acacagccta cctgcaaatg aacagcctgc gtgctgagga cactgccgtc | 1440 |
| tattattgtg ctagaagcgg atactacggc gatagcgact ggtattttga cgtctggggt | 1500 |
| caaggaaccc tggtcaccgt c | 1521 |

<210> SEQ ID NO 46
<211> LENGTH: 717
<212> TYPE: DNA
<213> ORGANISM: Artificial sequence
<220> FEATURE:
<223> OTHER INFORMATION: Synthesized

<400> SEQUENCE: 46

| | | |
|---|---|---|
| aattctcagc tgttggagtc tgggggaggc ttggtacagc ctgggggtc cctgcgtctc | 60 | |
| tcctgtgcag cctccggata taggattagc tctgacgata tgagctgggt ccgccaggct | 120 | |
| ccagggaagg gtctagagtg ggtatcaacc atttatgaga cagacggtag cacatactac | 180 | |
| gcagactccg tgaagggccg gttcaccatc tcccgtgaca attccaagaa cacgctgtat | 240 | |
| ctgcaaatga acagcctgcg tgccgaggac accgcggtat attattgcgc gagagctaat | 300 | |
| ttttatagtg agcagccctt ccagttttgg ggtcagggaa ccctggtcac cgtctcgagc | 360 | |
| ggcggaggag gctccaactg ggtgaacgtc atctccgacc tcaagaagat cgaggacctg | 420 | |
| atccagagca tgcacatcga cgccaccctg tataccgaga gcgacgtgca cccctcctgt | 480 | |
| aaagtgaccg ccatgaagtg cttcctgctg gagctgcagg tgatcagcct ggagagcggc | 540 | |
| gacgccagca tccatgacac cgtggagaac ctgatcatcc tggccaataa cagcctgagc | 600 | |
| tccaacggca acgtgaccga gagcggctgc aaggaatgcg aggagctgga gaagaagaac | 660 | |
| attaaggagt cctgcagag cttcgtccac atcgtgcaga tgttcattaa cacctcc | 717 | |

<210> SEQ ID NO 47
<211> LENGTH: 1431
<212> TYPE: DNA
<213> ORGANISM: Artificial sequence
<220> FEATURE:
<223> OTHER INFORMATION: Synthesized

<400> SEQUENCE: 47

| | | |
|---|---|---|
| atgtacagga tgcaactcct gtcttgcatt gcactaagtc ttgcacttgt cacgaattct | 60 | |
| gatatccaga tgacccagtc cccgagctcc ctgtccgcta gcgtgggcga tagggtcacc | 120 | |
| atcacctgtc gtgccagtca ggacatccgt aattatctca actggtatca acagaaacca | 180 | |
| ggaaaagctc cgaaactact gatttactat acctcccgcc tggagtctgg agtcccttct | 240 | |
| cgcttctctg gttctggttc tgggacggat tacactctga ccatcagcag tctgcaaccg | 300 | |
| gaggacttcg caacttatta ctgtcagcaa ggtaatactc tgccgtggac gttcggacag | 360 | |
| ggcaccaagg tggagatcaa aggtggaggc ggttcaggcg gaggtggctc tggcggtggc | 420 | |
| ggatcggagg ttcagctggt ggagtctggc ggtggcctgg tgcagccagg gggctcactc | 480 | |
| cgtttgtcct gtgcagcttc tggctactcc tttaccggct acactatgaa ctgggtgcgt | 540 | |
| caggccccag gtaagggcct ggaatgggtt gcactgatta tccttataa aggtgtttcc | 600 | |
| acctataacc agaaattcaa ggatcgtttc acgatatccg tagataaatc caaaaacaca | 660 | |
| gcctacctgc aaatgaacag cctgcgtgct gaggacactg ccgtctatta ttgtgctaga | 720 | |
| agcggatact acggcgatag cgactggtat tttgacgtct ggggtcaagg aaccctggtc | 780 | |
| accgtcggcg gcggcggatc tatcacgtgc cctccccca tgtccgtgga acacgcagac | 840 | |
| atctgggtca agagctacag cttgtactcc agggagcggt acatttgtaa ctctggtttc | 900 | |
| aagcgtaaag ccggcacgtc cagcctgacg gagtgcgtgt tgaacaaggc cacgaatgtc | 960 | |
| gcccactgga caaccccag tctcaaatgc attagagacc ctgccctggt tcaccaaagc | 1020 | |
| ggcggctccg ggggaggtgg atccggaggt ggctccggtg gaggcggaag cctgcagcag | 1080 | |
| ctgttggagt ctgggggagg cttggtacag cctggggggt ccctgcgtct cctgtgca | 1140 | |
| gcctccggat ataggattag ctctgacgat atgagctggg tccgccaggc tccagggaag | 1200 | |
| ggtctagagt gggtatcaac catttatgag acagacggta gcacatacta cgcagactcc | 1260 | |
| gtgaagggcc ggttcaccat ctcccgtgac aattccaaga acacgctgta tctgcaaatg | 1320 | |
| aacagcctgc gtgccgagga caccgcggta tattattgcg cgagagctaa ttttttatagt | 1380 | | gagcagccct tccagttttg gggtcaggga accctggtca ccgtctcgag c          1431

<210> SEQ ID NO 48
<211> LENGTH: 1557
<212> TYPE: DNA
<213> ORGANISM: Artificial sequence
<220> FEATURE:
<223> OTHER INFORMATION: Synthesized

<400> SEQUENCE: 48
atgtacagga tgcaactcct gtcttgcatt gcactaagtc ttgcacttgt cacgaattct    60
cagctgttgg agtctggggg aggcttggta cagcctgggg gtccctgcg tctctcctgt    120 gcagcctccg gatataggat tagctctgac gatatgagct gggtccgcca ggctccaggg   180
aagggtctag agtgggtatc aaccatttat gagacagacg gtagcacata ctacgcagac   240
tccgtgaagg gccggttcac catctcccgt gacaattcca agaacacgct gtatctgcaa   300
atgaacagcc tgcgtgccga ggacaccgcg gtatattatt gcgcgagagc taatttttat   360
agtgagcagc ccttccagtt ttggggtcag ggaaccctgg tcaccgtctc gagcggcggc   420
ggcggatcta actgggtgaa cgtcatctcc gacctcaaga gatcgagga cctgatccag   480 agcatgcaca tcgacgccac cctgtatacc gagagcgacg tgcacccctc ctgtaaagtg   540
accgccatga agtgcttcct gctggagctg caggtgatca gcctggagag cggcgacgcc   600
agcatccatg acaccgtgga gaacctgatc atcctggcca ataacagcct gagctccaac   660
ggcaacgtga ccgagagcgg ctgcaaggaa tgcgaggagc tggagaagaa gaacattaag   720
gagttcctgc agagcttcgt ccacatcgtg cagatgttca ttaacacctc cagcggcggc   780
tccgggggag gtggatccgg aggtggctcc ggtggaggcg gaagcctgca ggatatccag   840
atgacccagt ccccgagctc cctgtccgct agcgtgggcg atagggtcac catcacctgt   900
cgtgccagtc aggacatccg taattatctc aactggtatc aacagaaacc aggaaaagct   960
ccgaaactac tgatttacta tacctcccgc ctggagtctg gagtcccttc tcgcttctct   1020
ggttctggtt ctgggacgga ttacactctg accatcagca gtctgcaacc ggaggacttc   1080
gcaacttatt actgtcagca aggtaatact ctgccgtgga cgttcggaca gggcaccaag   1140
gtggagatca aagtggaggc ggttcaggc ggaggtggct ctggcggtgg cggatcggag   1200
gttcagctgg tggagtctgg cggtggcctg gtgcagccag ggggctcact ccgtttgtcc   1260
tgtgcagctt ctggctactc ctttaccggc tacactatga actgggtgcg tcaggcccca   1320
ggtaagggcc tggaatgggt tgcactgatt aatccttata aggtgtttc cacctataac   1380 cagaaattca aggatcgttt cacgatatcc gtagataaat ccaaaaacac agcctacctg   1440
caaatgaaca gcctgcgtgc tgaggacact gccgtctatt attgtgctag aagcggatac   1500
tacggcgata gcgactggta tttgacgtc tggggtcaag aaccctggt caccgtc       1557

<210> SEQ ID NO 49
<211> LENGTH: 681
<212> TYPE: DNA
<213> ORGANISM: Artificial sequence
<220> FEATURE:
<223> OTHER INFORMATION: Synthesized

<400> SEQUENCE: 49
ccaggatggt tcttagactc cccagacagg ccctggaacc cccccacctt ctccccagcc    60
ctgctcgtgg tgaccgaagg ggacaacgcc accttcacct gcagcttctc caacacatcg    120

```
gagagcttcg tgctaaactg gtaccgcatg agccccagca accagacgga caagctggcc      180
gccttccccg aggaccgcag ccagcccggc caggactgcc gcttccgtgt cacacaactg      240
cccaacgggc gtgacttcca catgagcgtg gtcagggccc ggcgcaatga cagcggcacc      300
tacctctgtg gggccatctc cctggccccc aaggcgcaga tcaaagagag cctgcgggca      360
gagctcaggg tgacagagag aagggcagaa gtgcccacag cccacccagc ccctcaccc      420 aggccagccg gccagttcca aaccctggtg ggcggaggag gctccatcac gtgccctccc      480
cccatgtccg tggaacacgc agacatctgg gtcaagagct acagcttgta ctccagggag      540
cggtacattt gtaactctgg tttcaagcgt aaagccggca cgtccagcct gacggagtgc      600
gtgttgaaca aggccacgaa tgtcgcccac tggacaaccc ccagtctcaa atgcattaga      660
gaccctgccc tggttcacca a                                                681

<210> SEQ ID NO 50
<211> LENGTH: 342
<212> TYPE: DNA
<213> ORGANISM: Artificial sequence
<220> FEATURE:
<223> OTHER INFORMATION: Synthesized

<400> SEQUENCE: 50
aactgggtga acgtcatctc cgacctcaag aagatcgagg acctgatcca gagcatgcac       60
atcgacgcca ccctgtatac cgagagcgac gtgcacccct cctgtaaagt gaccgccatg      120
aagtgcttcc tgctggagct gcaggtgatc agcctggaga cggcgacgc cagcatccat       180 gacaccgtgg agaacctgat catcctggcc aataacagcc tgagctccaa cggcaacgtg      240
accgagagcg gctgcaagga atgcgaggag ctggagaaga gaacattaa ggagttcctg      300 cagagcttcg tccacatcgt gcagatgttc attaacaccct cc                       342

<210> SEQ ID NO 51
<211> LENGTH: 21
<212> TYPE: PRT
<213> ORGANISM: Artificial sequence
<220> FEATURE:
<223> OTHER INFORMATION: Synthesized

<400> SEQUENCE: 51

Met Ala Leu Pro Val Thr Ala Leu Leu Leu Pro Leu Ala Leu Leu Leu
1               5                   10                  15

His Ala Ala Arg Pro
            20

<210> SEQ ID NO 52
<211> LENGTH: 22
<212> TYPE: PRT
<213> ORGANISM: Artificial sequence
<220> FEATURE:
<223> OTHER INFORMATION: Synthesized

<400> SEQUENCE: 52

Gly Ser Gly Ala Thr Asn Phe Ser Leu Leu Lys Gln Ala Gly Asp Val
1               5                   10                  15

Glu Glu Asn Pro Gly Pro
            20
```

MULTIFUNCTIONAL PROTEIN

RELATED APPLICATIONS

The present application is a National Phase of International Application Number PCT/CN2017/118984, filed Dec. 27, 2017, and claims the priority of China Application No. 201611246592.0, filed Dec. 29, 2016.

FIELD OF THE INVENTION

The present invention relates to the field of biology, and in particular to a multifunctional protein.

INCORPORATION BY REFERENCE

The sequence listing provided in the file entitled 1980023 C6351-008 Sequence listing v4.txt which is an ASCII text file that was created on Jul. 12, 2022, and which comprises 115,677 bytes, is hereby incorporated by reference in its entirety.

BACKGROUND OF THE INVENTION

Bispecific antibodies, also known as bifunctional antibodies or bivalent antibodies, can specifically bind to two different antigens simultaneously, with specificity and bi-functionality, have broadly application in the future in the fields of tumor immunotherapy and autoimmune diseases etc.

Bispecific antibodies are not found in nature and can only be prepared by artificial methods. At present, methods for preparing bispecific antibodies mainly include chemical conjugation, hybridoma technology, and recombinant DNA technology etc.

Medarex had developed bispecific antibodies as early as 30 years ago and conducted a phase III clinical trial in 2001. However, the research in this field has been silent due to clinical trial failures and manufacture problems (Garber K, 2014). In 2009, the bispecific antibody Catumaxomab developed by Trion was approved by the European Union for the treatment of malignant ascites caused by EpCAM-positive tumors, but its high immunogenicity greatly limits its clinical application (Spasevska I, 2014). In recent years, the rapid progress of antibody engineering technology has brought new opportunities for the development of bispecific antibodies.

1. Synthetic Bispecific Antibodies by Chemical Coupling.

Her2/CD3 bispecific antibodies were obtained by chemical coupling of the commercialized Herceptin with OKT3 in Lum Laboratory to recruit T cells to kill Her2-positive tumor cells (Msen et al., 2001). This antibody conjugate based on clinically widely used antibodies showed very good records of clinical safety and efficacy. Five of the 22 patients with metastatic breast cancer who participated in the clinical trial remained stable disease condition within 14.5 weeks after use (Lum et al., 2015).

OKT3 antibody has also been used to chemically conjugate with other clinically used antibodies to kill tumors with corresponding targets: including EGFR-positive tumors (Reush U et al., 2006; MAD et al., 2015), CD20 positive tumor line (Lum et al., 2013), B7-H3 positive tumors (MA et al., 2016) and the like.

2. Bispecific Antibodies Produced by Hybridoma Technology

Lindnorer et al. fused a rat hybridomas secreting anti-CD3 antibody with a mouse hybridomas secreting anti-EpCAM to obtain a hybridoma that could secrete up to 11 antibodies consisting of different heavy and light chains (Lindnoer et al., 1995). The bispecific antibodies prepared from heterologous rat and mouse hybridomas inevitably produce a human anti-mouse (HAMA) cross-reactivity. Surprisingly, this anti-drug response is in direct proportion to the efficacy of patient's response to the antibody (OTT M G et al., 2012) and its mechanism needs to be further explored. It has been approved for clinical use in 2009 (Carberk, 2014). The Her/CD3 antibody (Kiewe et al., 2006) was developed on the same platform. Anti-CD20/CD3 antibody for the treatment of relapsed B cell lymphoma has been approved for clinical trials and shows a good safety record and efficacy (Buhmann et Al., 2009). A bispecific antibody of anti-CD2/CD3 has been used in experimental studies of melanoma (Ruf et al., 2004).

3. Expression of Bispecific Molecules by Recombinant Technology

Genentech scientist Shalaby et al. linked the Fab fragment of the humanized anti-CD3 antibody UCHT1 to the anti-HER2 antibody 4D5 via a linker peptide and successfully expressed it in an *E. coli* expression system. This bispecific antibody specifically recognizes HER2-highly expressed breast cancer cell line SK-BR-3 and mediates the killing of this tumor cell line by human peripheral blood T cells (Shalaby et al., 1992). With the development of synthetic biomolecules and protein recombinant technology, protein molecules prepared by genetic engineering to recruit T cells to target tumors have come to the fore and have become the mainstream of such drugs.

BiTE: In December 2014, FDA approved a new engineered CD3 targeting bispecific antibody molecule-BiTE (Bispecific T-cell engager) for the treatment of acute lymphoblastic leukaemia. This novel small protein molecule is directly linked by the scFv of OKT3 and the anti-CD19 scFv via a linker peptide (Nagorsen D et al., 2012) (Patent No.: 201180063222.2; 201580009124.9), requiring only very low concentrations to inhibit the growth of non-Hodgkin's lymphoma (Bargou R et al., 2008). Due to the ability of this molecule to efficiently recruit T cells to kill target cells, more products targeting different tumors based on BiTE platform have entered clinical trials including several BiTE molecules that recognise EpCAM, CEA, and DSMA (Thakur A et al., 2016) etc.

T and Ab connects a pair of BiTE-like bispecific molecules with a linker peptide to form a tetrameric molecule called T and Ab with a molecular weight of 160 kD doubling that of BiTE, making it to bind to CD3 and CD19 with higher affinity (Reusch U et al, 2015). At the same time, the pharmacokinetics of T and Ab is also significantly improved compared to BiTE, the half-life in the blood reaches about 20 h. It can mediate the killing of non-Hodgkin's lymphoma and acute lymphoblastic leukaemia.

DART is a combination of anti-CD19 and anti-CD3 scFv through a disulfide-containing linker peptide. It can recruit T cells to kill tumors and has the advantages of stable and easy scale preparation (Johnson S et al, 2010; Kuo S R et al., 2012).

FcabFv fuses the antigen recognition fragment of OKT3 with a mutated Fc (Wozniak G et al., 2010) which has a function of recognizing Her2 produced by CH3 mutation and expresses a novel bispecific antibody highly similar to a conventional antibody. It can effectively target Her2-positive tumors and inhibit tumor growth in vivo (Wang L et al., 2013).

TriKE inserts IL-15 between the scFv of CD33 antibody and the scFv of CD16 antibody and is linked by two linked peptides. It can effectively promote the activation and survival of NK cells in vivo while effectively targeting tumors. Adding IL-15 that is beneficial for NK cells to treat myeloid malignancies or to target solid tumors (Szun Tay et al., 2016; Vallera D A. et al., 2016).

Currently, bispecific antibodies have become a new hotpot in the field of pharmaceutical research, there are at least 30 kinds of bispecific antibodies in clinical development phase (Garber K et al, 2014; Kontermann R E et al., 2015).

A certain amount of IL-2 must be added to the culture medium of both T cells and NK cells (Bodnar et al., 2008; Grund et al., 2005). IL-15 is functionally similar to IL-2 and shares the same βγ receptor. Studies indicate that IL-2 or IL-15 is required for survival and proliferation of NK cells and CD8+ T cells (Boyman et al., 2007). Although IL-15 and IL-2 share the same fly receptor, they each have a specific a receptor. It was found that IL-15Rα-sushi (the sushi domain of IL-15 receptor a) is super agonist of IL-15. An agonist can greatly enhance the function of IL-15 (Han et al., 2011; Mortier et al., 2006) (Patent Application No.: 201280037114.2, 201510358540.1) and the complex of IL-15 and IL-15Rα-sushi can completely replace the role of IL-2 in T/NK cells (Peter S. Kiml, 2016; Rosario et al., 2016) to activate NK/CD8+ T cells and increase their cytotoxicity against tumors. The National Institutes of Health (NIH) National Cancer Institute rankedIL-15 as number one agent among 12 immunotherapeutics for cancer treatment. By supporting the viability of CD8+ T cells, IL-15 has demonstrated great potential for the maintenance of long-term immune response in T cells. Compared with IL-2, IL-15 is a more promising, more effective, less toxic product in tumor treatment, and can stimulate anti-tumor activities of both T cells and NK cells. Fusion of IL-15 and IL-15Rα-sushi complex or other functional cytokine and receptor complexes in bispecific molecules is a major trend to improve the efficacy of cellular immunotherapy.

PD-1 (programmed death 1) and its receptors PD-L1, PD-L2 are important regulators of T cell activity (Okazaki and Honjo, 2007). The binding of PD-1 on the surface of T cells to PD-L1/2 on the surface of other cells causes inhibition of T cells, which plays an important role in the process of avoiding autoimmune diseases and producing immune tolerance in humans. By contrast, tumor cells utilize the self-regulating mechanism of PD1/PD-L1 checkpoint to achieve the purpose of suppressing immune response, tumor escape by expressing PD-L1/L2 in the tumor cell itself or in the tumor microenvironment to bind to PD1 on the surface of T cells, transmitting a negative signal, leading to a decline in T cell function and exhaust of T cells (Freeman et al., 2000; Keir et al., 2008; Parry et al., 2005). Therefore, the researchers explored the use of PD-1 or PD-L1 antibodies to bind respective antigens and blocked the PD1 checkpoint pathway of T cells while targeting tumors. The results showed that this method can significantly increase T cell activity and enhance the body's resistance to pathogenic microorganisms cancer (Topalian et al., 2012; Yanan Guo et al., 2016). A number of clinical trials have demonstrated good therapeutic effects by PD-1/PD-L1 antibodies against melanoma (Cho et al., 2016; Hamid et al., 2013), multiple myeloma (Badros et al., 2015), leukaemia (Pork et al., 2014) (Patent Application No.: 200380109929.8, 201310258289.2, 201180019629.5).

DISCLOSURE OF THE INVENTION

One of objects of the invention is to provide a polypeptide chain X.

The polypeptide chain X provided by the invention includes an antigen 1 binding domain R1, a co-peptide chain linkage domain R2 and an antigen 2 binding domain R3.

The co-peptide linkage domain R2 is a cytokine, or cytokine binding domain in a cytokine receptor.

In the above polypeptide chain X, the antigen 2 binding domain R3 is an antibody or molecule that recognizes CD3 of a T cell.

In the above polypeptide chain X, the antigen 2 binding domain R3 is a receptor or antibody or other molecules that recognizes CD16 on an NK cell.

In the above polypeptide chain X, the antigen to which the antigen 1 binding domain R1 binds is selected from any of the following cancer-related antigens: brain cancer, bladder cancer, breast cancer, cervical cancer, colorectal cancer, liver cancer, kidney cancer, lymphoma, and leukaemia, lung cancer, melanoma, metastatic melanoma, mesothelioma, neuroblastoma, ovarian cancer, prostate cancer, pancreatic cancer, kidney cancer, skin cancer, thymoma, sarcoma, non-Hodgkin's lymphoma, Hodgkin lymphoma and uterine cancer.

In the above polypeptide chain X, the cancer-associated antigen is preferably from any one of the following antigens: CD123, CD19, CD20, CD22, CD37, ROR1, mesothelin, CD33/IL3Ra, c-Met, BCMA, PSMA, EGFRvIII, GD-2, NY-ESO-1, MAGEA3, β-human chorionic gonadotropin, AFP, RAGE-1, MN-CAIX, human telomerase reverse transcriptase, RU1, RU2 (AS), hsp70-2, M-CSF, PSA, PAP, LAGE-la, p53, Prostein, PSMA, Her2/neu, telomerase, PCTA-1, MAGE, ELF2M, IGF-I, IGF-II, IGF-I receptor, BCR-ABL, E2A-PRL, H4-RET, IGH-IGK, MYL-RAR, GP100, Mart1, TSP-180, MAGE-4, MAGE-5, MAGE-6, RAGE, p185erbB2, p180erbB-3, c-met, nm-23H1, TAG-72, CA 19-9, CA 72-4, CAM 17.1, NuMa, K-ras, β-catenin, CDK4, Mum-1, p15, p16, 43-9F, 5T4, 791Tgp72, β-HCG, BCA225, BTAA, CA 125, CA 15-3\CA 27.29\BCAA, CA 195, CA 242, CA-50, WT1, CD68, FGF-5, G250, EpCAM, MA-50, MG7-Ag, MOV 18, NB/70K, RCAS1, SDCCAG16, TA-90, TAAL6, TAG72, TLP, p53, Ras, TPS, Epstein Barr virus antigen EBVA, human papillomavirus (HPV) antigen E6, human papilloma Toxicity (HPV) E7 antigens or the complex of MEW with a short peptide derived from any of antigens above-described.

The antigen in the complex of MEW with the short peptide of which is any one of the above cancer-related antigens.

In the above polypeptide chain X, the cancer-associated antigen is preferably selected from any one of the following antigens: CD19, CD20, CD22, CD123, CD33/IL3Ra, Her2, PDL1, GP100, Mart1, BCMA, WT-1 and NY-ESO-1 or a complex of MEW with a short peptide of one of the above antigens.

The antigen in the complex of the MHC and the short peptide of the antigen is preferably any one of the following antigens selected from the cancer-associated antigens.

In the above polypeptide chain X, the cancer-associated antigen is preferably selected from any one of the following antigens: CD19, CD20, CD22, Her2, PDL1, WT1, GP100, Mart1, BCMA, and NY-ESO-1 or a complex of MHC with a short peptide derived from the above-described antigen.

In the above polypeptide chain X, the antigen 1 binding domain R1 is an antigen-binding antibody, an antigen-binding ligand, an antigen-binding receptor, or a polypeptide having antigen-binding function.

In the above polypeptide chain X, the antigen-binding antibody is an intact immunoglobulin, an antibody Fc, an antibody Fab, an antibody VH, an antibody VL or a full-length peptide chain or a partial peptide chain of a scFv.

In the above polypeptide chain X, the antigen-binding ligand or the antigen-binding receptor is a full-length peptide chain or a partial peptide chain.

In the above polypeptide chain X, the antigen 1 binding domain R1 is a TCR with an antigen recognition function.

In the above polypeptide chain X, the antigen 1 binding domain R1 is a TCR-like antibody or other molecule having an antigen recognition function.

Another object of the present invention is to provide a protein.

The protein provided by the present invention, which is a heterodimer comprising a peptide chain X of claim 1 as a main peptide chain and a co-peptide chain Y. The co-peptide chain Y comprises R4 as an antigen 3 binding domain and R5 as the main peptide chain X linking domain.

Or the co-peptide chain Y is the main peptide chain linking domain R5.

The main peptide chain linking domain R5 and the co-peptide chain linking domain R2 in the peptide chain X bind to each other.

The functional domains of the above main peptide chain and co-peptide chain are linked by a polypeptide linker. These polypeptide linkers are glycine- and/or serine-rich sequences or multiple copies of glycine and/or serine-rich sequences, and polypeptide linkers typically include from 1 to 20 amino acid residues.

The main peptide chain linking domain R5 and the cytokine or the cytokine binding domain R2 of a cytokine receptor are a pair of peptides having a mutual binding function.

The above-mentioned co-peptide chain linking domain (R2) and main peptide chain linking domain (R5) are cytokines and receptor subunits or vice versa. A heterodimer is formed between the main peptide chain (X) and the co-peptide chain (Y) by binding of the co-peptide chain linking domain (R2) to the main peptide chain linking domain (R5).

Among the above proteins, the antigen 3 to which the antigen 3 binding domain R4 binds is selected from any of the following cancer-related antigens: brain cancer, bladder cancer, breast cancer, cervical cancer, colorectal cancer, liver cancer, kidney cancer, lymphoma, Leukaemia, lung cancer, melanoma, metastatic melanoma, mesothelioma, neuroblastoma, ovarian cancer, prostate cancer, pancreatic cancer, kidney cancer, skin cancer, thymoma, sarcoma, non-Hodgkin's lymphoma, Hodgkin's lymphoma and uterine cancer.

Among the above proteins, the cancer-associated antigen 3 is preferably one of the following antigens: CD123, CD19, CD20, CD22, CD37, ROR1, mesothelin, CD33/IL3Ra, c-Met, BCMA, PSMA, EGFRvIII, GD-2, NY-ESO-1, MAGEA3, β-human chorionic gonadotropin, AFP, RAGE-1, MN-CAIX, human telomerase reverse transcriptase, RU1, RU2 (AS), hsp70-2, M-CSF, PSA, PAP, LAGE-la, p53, Prostein, PSMA, Her2/neu, PDL1, telomerase, PCTA-1, MAGE, ELF2M, IGF-I, IGF-II, IGF-I receptor, BCR-ABL, E2A-PRL, H4-RET, 1GH-IGK, MYL-RAR, GP100, Mart1, TSP-180, MAGE-4, MAGE-5, MAGE-6, RAGE, p185erbB2, p180erbB-3, c-met, nm-23H1, TAG-72, CA 19-9, CA 72-4, CAM 17.1, NuMa, K-ras, β-catenin, CDK4, Mum-1, p15, p16, 43-9F, 5T4, 791Tgp72, β-HCG, BCA225, BTAA, CA 125, CA 15-3\CA 27.29\BCAA, CA 195, CA 242, CA-50, WT1, CD68, FGF-5, G250, EpCAM, M344, MA-50, MG7-Ag, MOV18, NB/70K, RCAS1, SDCCAG16, TA-90, TAAL6, TAG72, TLP, p53, Ras, TPS, Epstein Barr virus antigen EBVA, human papillomavirus (HPV) antigen E6 Human papillomavirus (HPV) E7 antigen complexes or the complexes of MEW associated with a peptide derived from one of above-described antigens.

The antigen in the complex of the MHC and the short peptide derived from is the cancer-associated antigen 3, preferably from any of the above antigens.

Among the above proteins, the cancer-associated antigen is preferably selected from any one of the following antigens: CD19, CD20, CD22, CD123, CD33/IL3Ra, Her2, PDL1, GP100, Mart1, BCMA, WT-1, NY ESO-1 or the complex of MEW with a short peptide derived from the above antigens.

The antigen in the complex of MEW and a short peptide derived from is any one of CD19, CD20, CD22, CD123, CD33/IL3Ra, Her2, PDL1, GP100, Mart1, BCMA, WT-1 and NY_ESO-1.

Among the above proteins, the cancer-associated antigen is preferably selected from any one of the following antigens: CD19, CD20, CD22, Her2, PDL1, WT1, GP100, Mart1, BCMA, NY ESO-1 or a complex of MHC with a short peptide derived from the above-mentioned antigens; The antigen in the complex of MHC and the short peptide of the antigen is any one of CD19, CD20, CD22, Her2, PDL1, WT1, GP100, Mart1, BCMA, NY_ESO-1.

In the above, the positions of the antigen 1 binding domain R1 and the antigen 2 binding domain R3 are interchangeable.

In the above, the positions of the antigen 1 binding domain R1 and the antigen 3 binding domain R4 are interchangeable.

In the above, the positions of the antigen 2 binding domain R3 and the antigen 3 binding domain R4 are interchangeable.

In the above, the co-peptide chain linkage domain R2 and the main peptide chain linkage domain R5 are a pair of peptides having a function of binding to each other. Preferably, a pair of γc cytokines and their receptor subunits can be bound to each other. The optimal choices are IL15 and IL15Rα, and IL4 and IL4Rα. IL15 plays an indispensable role in maintaining the homeostasis and the growth of T cells, NK cells and NKT cells, while providing additional physiology function to B cells, dendritic cells (DCs), macrophages, and mast cells. IL-15 can support the survival of CD8+ T cells more promising and more effective than IL-2. It is less toxic in tumor treatment and can stimulate the anti-tumor activity of T cells and NK cells.

In the above, the co-peptide chain linkage domain R2 and the main peptide chain linkage domain R5 are a pair of a cytokine and a receptor subunit and bind to each other thereof.

In the above, the cytokine mentioned is a γc family cytokine,

The γc family cytokine is IL2, IL4, IL7, IL9, IL15 or IL21.

In the above, the cytokine and receptor subunits are optimally selected from the group consisting of IL15 and IL15Rα and the group of IL4 and IL4Rα.

In the above, each component of the main peptide chain of the polypeptide or protein or a component of the co-peptide chain is linked by a polypeptide linker consisting of 1-20 amino acid residues.

In the above, the polypeptide linker is rich in glycine and/or serine.

In the above, the antigen 1 binding domain R1 is an anti-CD19-ScFv or AntiMHC/GP100-VHH or AntiMHC/

Mart1-VHH or AntiMHC/WT1, or an extracellular region of PD1, or Anti-CD22-ScFv, or anti-CD3-ScFv or anti-CD16-ScFv.

Or the co-peptide linkage domain R2 is IL15Rαsushi or IL4Rα-N-FN3 or IL15 or IL4.

Or the antigen 2 binding domain R3 is an anti-CD3-ScFv or anti-CD16-ScFv or anti-CD19-ScFv, or AntiMHC/GP100-VHH or AntiMHC/Mart1-VHH or AntiWT1, or an extracellular region of PD1 or Anti-CD22-ScFv.

Or the antigen 3 binding domain R4 is the extracellular domain of PD1 or AntiMHC/GP100-VHH or Anti-CD22-ScFv or Anti-CD19-ScFv; or AntiMHC/Mart1-VHH or AntiMHC/WT1 or Anti-CD3-ScFv or Anti-CD16-ScFv.

Alternatively, the main peptide chain linkage domain R5 is IL15 or IL4 or IL15Rαsushi or IL4Rα-N-FN3.

In the above, the anti-CD19-ScFv comprises the amino acid sequence of SEQ ID NO. 1.

The IL15Rαsushi comprises the amino acid sequence of SEQ ID NO. 2.

The anti-CD3-ScFv comprises the amino acid sequence of SEQ ID NO. 3.

The extracellular region of PD1 comprises the amino acid sequence of SEQ ID NO. 4.

The IL15 comprises the amino acid sequence of SEQ ID NO. 5.

The AntiMHC/GP100-VHH comprises the amino acid sequence of SEQ ID NO. 10.

The AntiMHC/Mart1-VHH comprises the amino acid sequence of SEQ ID NO. 11.

The AntiMHC/WT1-VH comprises the amino acid sequence of SEQ ID NO. 12.

The IL4Rα comprises the amino acid sequence of the SEQ ID NO. 13.

The Anti-CD16-ScFv comprises the amino acid sequence of SEQ ID NO. 14.

The Anti-CD22-ScFv comprises the amino acid sequence of SEQ ID NO. 15.

The IL4 comprises the amino acid sequence of SEQ ID NO. 16. In the above, the polypeptide chain X comprises the amino acid sequence of SEQ ID NO. 8.

Or the polypeptide chain X comprises the amino acid sequence of SEQ ID NO. 17.

Or the polypeptide chain X comprises the amino acid sequence of SEQ ID NO. 19.

Or the polypeptide chain X comprises the amino acid sequence of SEQ ID NO. 21.

Or the polypeptide chain X comprises the amino acid sequence of SEQ ID NO. 22.

Or the polypeptide chain X comprises the amino acid sequence of SEQ ID NO. 23.

Or the polypeptide chain X comprises the amino acid sequence of SEQ ID NO. 27.

Or the polypeptide chain X comprises the amino acid sequence of SEQ ID NO. 29.

Or the polypeptide chain X comprises the amino acid sequence of SEQ ID NO. 30.

Or the main peptide chain of the protein comprises the amino acid sequence of SEQ ID NO. 8, and the co-peptide chain comprises the amino acid sequence of SEQ ID NO. 9.

Or the main peptide chain of the protein comprises the amino acid sequence of SEQ ID NO. 17, and the co-peptide chain comprises the amino acid sequence of SEQ ID NO. 9.

Or the main peptide chain of the protein comprises the amino acid sequence of SEQ ID NO. 17, and the co-peptide chain comprises the amino acid sequence of SEQ ID NO. 18.

Or the main peptide chain of the protein comprises the amino acid sequence of SEQ ID NO. 19, and the co-peptide chain comprises the amino acid sequence of SEQ ID NO. 9.

Or the main peptide chain of the protein comprises the amino acid sequence of SEQ ID NO. 8, and the co-peptide chain comprises the amino acid sequence of SEQ ID NO. 20.

Or the main peptide chain of the protein comprises the amino acid sequence of SEQ ID NO. 21, and the co-peptide chain comprises the amino acid sequence of SEQ ID NO. 9.

Or the main peptide chain of the protein comprises the amino acid sequence of SEQ ID NO. 22, and the co-peptide chain comprises the amino acid sequence of SEQ ID NO. 9.

Or the main peptide chain of the protein comprises the amino acid sequence of SEQ ID NO. 23, and the co-peptide chain comprises the amino acid sequence of SEQ ID NO. 24.

Or the main peptide chain of the protein comprises the amino acid sequence of SEQ ID NO. 25, and the co-peptide chain comprises the amino acid sequence of SEQ ID NO. 26.

Or the main peptide chain of the protein comprises the amino acid sequence of SEQ ID NO. 27, and the co-peptide chain comprises the amino acid sequence of SEQ ID NO. 28.

Or the main peptide chain of the protein comprises the amino acid sequence of SEQ ID NO. 29, and the co-peptide chain comprises the amino acid sequence of SEQ ID NO. 9.

Or the main peptide chain of the protein comprises the amino acid sequence of SEQ ID NO. 30, and the co-peptide chain comprises the amino acid sequence of SEQ ID NO. 31.

Or the main peptide chain of the protein comprises the amino acid sequence of SEQ ID NO. 21, and the co-peptide chain comprises the amino acid sequence of SEQ ID NO. 5.

Or the main peptide chain of the protein comprises the amino acid sequence of SEQ ID NO. 8, and the co-peptide chain comprises the amino acid sequence of SEQ ID NO. 5.

A third object of the present invention is to provide a nucleic acid molecule encoding the above polypeptide or protein.

The present invention provides an encoding nucleic acid molecule of the above polypeptide or protein, comprising a nucleic acid molecule encoding the main peptide chain or a nucleic acid molecule encoding the main peptide chain and a nucleic acid molecule encoding the co-peptide chain.

A nucleic acid sequence encoding a desired molecule can be obtained using recombinant methods known in the art, such as, for example, by screening a library from a cell expressing the gene, by obtaining the gene from a vector known to include the gene, or by isolating the gene directly from cells and tissues containing the gene, or to synthesize polynucleotides by artificial synthesis with standard methods.

Recombinant vectors, expression cassettes, recombinant microbe strain, recombinant viruses or cells containing the above nucleic acid molecules are also within the scope of the present invention.

In the above recombinant vector, the recombinant vector is obtained by inserting a nucleic acid molecule encoding the main peptide chain in the above nucleic acid molecule or a nucleic acid molecule encoding the main peptide chain and a nucleic acid molecule encoding the co-peptide chain into an expression vector and the vector expressing the above protein is obtained.

The above recombinant vector comprises the above polynucleotide sequence or combination. In one embodiment, a nucleic acid encoding a primary peptide chain (X) or a co-peptide chain (Y) can be ligated to a promoter, and the construct is incorporated into an expression vector to achieve the expression of a primary peptide chain (X) or a co-peptide chain (Y). A typical cloning vector comprises a transcriptional and translational terminator, an initial sequence and a promoter that can be used to modulate the expression of a desired nucleic acid sequence. For example, lentiviral vector is a suitable tool for achieving long-term stable inheritance of genes because they allow long-term, stable integration of genes and their proliferation in daughter cells. Lentiviral vectors have the extra advantage of exceeding vectors derived from oncogenic retroviruses such as murine leukaemia viruses because they can transduce non-dividing cells, such as hepatocytes. They also have the added advantage of low immunogenicity. The multifunctional protein provided by the present invention comprises two peptide chains which can be co-expressed in the same cell by a known art, including but not limited to co-transfection of two genes encoding the main peptide chain (X) and the co-peptide chain (Y), respectively. An expression vector, or a nucleic acid sequence encoding a main peptide chain (X) and a co-peptide chain (Y), or an expression vector containing two sets of expression frameworks for encoding a main peptide chain (X) and a co-peptide chain (Y) is ligated in tandem into an expression frame, co-expressed by inserting a ribosome binding site between the nucleic acid sequences of the main peptide chain (X) and the co-peptide chain (Y). Or 2A peptide is used for co-expression of two polypeptides.

In the above cells, the cell of interest is a prokaryotic cell, a yeast cell, or a mammalian cell; wherein the mammalian cell is preferably a human cell.

The present invention also provides a kit comprising the above polypeptide chain X or the above protein, the above nucleic acid molecule or the above recombinant vector, expression cassette, recombinant microbe strain, recombinant virus, or cell.

The use of the above polypeptide or protein, the above nucleic acid molecule or the above recombinant vector, expression cassette, recombinant microbe strain, cell or recombinant virus or kit in immunotherapy is also within the scope of protection of the present invention.

Or the use of the above polypeptide or protein, the above nucleic acid molecule or the above recombinant vector, expression cassette, recombinant microbe strain, cell or recombinant virus or kit for the preparation of an immunotherapeutic product is also within the scope of the present invention.

The use of the above polypeptide or protein, the above nucleic acid molecule or the above recombinant vector, expression cassette, recombinant microbe strain, cell or recombinant virus or kit in immune cell culture and/or promotion of immune cell expansion and/or immunoassay. The scope of protection of the present invention.

Or the use of the above polypeptide or protein, the above nucleic acid molecule or the above recombinant vector, expression cassette, recombinant microbe strain, cell or recombinant virus or kit in the preparation of immune cell culture and/or promotion of immune cell expansion and/or immunodetection products is also within the scope of the invention.

Or the use of the above polypeptide or protein, the above nucleic acid molecule or the above recombinant vector, expression cassette, recombinant microbe strain, cell or recombinant virus or kit for stimulating T or NK cell proliferation is also within the scope of protection of the present invention.

Or the use of the above polypeptide or protein, the above nucleic acid molecule or the above recombinant vector, expression cassette, recombinant microbe strain, cell or recombinant virus or kit for the preparation of a product for stimulating T or NK cell proliferation is also within the scope of protection of the present invention.

Or the use of the above polypeptide or protein, the above nucleic acid molecule or the above recombinant vector, expression cassette, recombinant microbe strain, cell or recombinant virus or kit for mediating immune cell inhibition or killing of target cells expressing the antigen in the protein is also the scope of protection of the present invention.

Or the use of the above polypeptide or protein, the above nucleic acid molecule or the above recombinant vector, expression cassette, recombinant microbe strain, cell or recombinant virus or kit for preparing a target cell product which mediates immune cell inhibition or killing of an antigen expressing the protein is also within the scope of the invention.

Or the use of the above polypeptide or protein, the above nucleic acid molecule or the above recombinant vector, expression cassette, recombinant microbe strain, cell or recombinant virus or kit for inhibiting or killing tumor cells is also within the scope of the present invention.

Or the use of the above polypeptide or protein, the above nucleic acid molecule or the above recombinant vector, expression cassette, recombinant microbe strain, cell or recombinant virus or kit for the preparation of a product for inhibiting or killing tumor cells is also within the scope of protection of the present invention.

Or the use of the above polypeptide or protein, the above nucleic acid molecule or the above recombinant vector, expression cassette, recombinant microbe strain, cell or recombinant virus or kit for treating or detecting a tumor is also within the scope of protection of the present invention.

Or the use of the above polypeptide or protein, the above nucleic acid molecule or the above recombinant vector, expression cassette, recombinant microbe strain, cell or recombinant virus or kit for the preparation of a therapeutic or detecting tumor product is also within the scope of protection of the present invention. Or the use of the above polypeptide or protein, the above nucleic acid molecule or the above recombinant vector, expression cassette, recombinant microbe strain, cell or recombinant virus or kit for inhibiting or killing target cells expressing the antigen derived from mentioned proteins is also within the scope of protection by the present invention.

Or the use of the above polypeptide or protein, the above nucleic acid molecule or the above recombinant vector, expression cassette, recombinant microbe strain, cell or recombinant virus or kit for preparing a target cell product for inhibiting or killing target cells expressing an antigen derived from mentioned proteins is also within the scope of protection by the present invention.

In the above, the immunotherapy is to inhibit or kill tumor cells by immune cells.

Or the immune cell is a T cell or an NK cell or the like.

Or the antigen is a cancer associated antigen.

Or the antigen is brain cancer, bladder cancer, breast cancer, cervical cancer, colorectal cancer, liver cancer, kidney cancer, lymphoma, leukaemia, lung cancer, melanoma, metastatic melanoma, mesothelioma, neuroblastoma, Ovarian cancer, prostate cancer, pancreatic cancer, renal cancer, skin cancer, thymoma, sarcoma, non-Hodgkin's lymphoma, Hodgkin's lymphoma, uterine cancer etc. associated antigen, or any combination thereof.

Alternatively, the tumor is brain cancer, bladder cancer, breast cancer, cervical cancer, colorectal cancer, liver cancer, kidney cancer, lymphoma, leukaemia, lung cancer, melanoma, metastatic melanoma, mesothelioma, and neuroblastoma. Any one or any combination of ovarian cancer, prostate cancer, pancreatic cancer, renal cancer, skin cancer, thymoma, sarcoma, non-Hodgkin's lymphoma, Hodgkin's lymphoma, uterine cancer; or any combination thereof; Or the target cell is a prokaryotic cell, a yeast cell, or a mammalian cell.

Or the mammalian cell is specifically a human cell; Or the human cell is specifically an immune cell, Alternatively, the immune cell is specifically a T cell or an NK cell.

In the above polypeptide or protein, the antigen-binding domain (R1/R3) of the main peptide chain and the co-peptide chain antigen binding domain (R4) have an ability to bind to an antigen. One of its antigen-binding domains is an antibody or molecule that recognizes CD3 of human T cells or a receptor or antibody or other molecule that recognizes NK cell CD16, and the other two are antibodies or molecules that recognize tumor-associated antigens selected from the group consisting of the following antigens. A tumor antigen to which an antigen binding domain binds is a protein produced by a tumor cell that elicits an immune response, particularly a T-cell mediated immune response. The choice of the antigen binding domain of the invention will depend on the particular type of cancer being treated. Tumor antigens are well known in the art: In one embodiment, the tumor-associated antigen referred to in the present invention may also be a tumor-associated antigen selected from the group consisting of brain cancer, bladder cancer, breast cancer, cervical cancer, colorectal cancer, liver cancer, kidney cancer, and lymphoma, leukaemia, lung cancer, melanoma, metastatic melanoma, mesothelioma, neuroblastoma, ovarian cancer, prostate cancer, pancreatic cancer, kidney cancer, skin cancer, thymoma, sarcoma, non-Hodgkin's lymphoma, Hodgkin's lymphoma, uterine cancer, and any combination thereof.

In particular: in one embodiment, the tumor antigens referred to in the present invention include, for example, glioma-associated antigen, carcinoembryonic antigen (CEA), β-human chorionic gonadotropin, α-fetoprotein (AFP), lectin-reactive AFP, thyroglobulin, RAGE-1, MN-CAIX, human telomerase reverse transcriptase, RU1, RU2 (AS), intestinal carboxylesterase, mut hsp70-2, M-CSF, prostatic enzyme, prostate-specific antigen (PSA), PAP, NY-ESO-1, LAGE-la, p53, prostein, PSMA, Her2/neu, survivin and telomerase, prostate-cancer tumor antigen-1 (PCTA-1)), MAGE, ELF2M, neutrophil elastase, ephrin B2, CD22, insulin growth factor (IGF)-I, IGF-II, IGF-I receptor and mesothelin.

In one embodiment, the tumor antigen comprises one or more antigenic cancer epitopes associated with the malignancy. Malignant tumors express many proteins that can be used as target antigens for immune attack. These molecules include, but are not limited to, tissue-specific antigens such as MART-1, tyrosinase and GP 100 in melanoma, and prostatic acid phosphatase (PAP) and prostate-specific antigen (PSA) in prostate cancer. Other target molecules belong to the group of transformation-related molecules such as the oncogene HER-2/Neu/ErbB-2. The other group of target antigens is a fetal cancer antigen such as carcinoembryonic antigen (CEA). In B-cell lymphoma, the tumor-specific individual genotype immunoglobulin constitutes the only true tumor-specific immunoglobulin antigen that is unique to an individual's tumor. B-cell differentiation antigens such as CD19, CD20 and CD37 are other candidates for target antigens in B-cell lymphoma. Some of these antigens (CEA, HER-2, CD19, CD20, individual genotypes) have been used with limited success as targets for passive immunotherapy using monoclonal antibodies. In one embodiment, the tumor antigen referred to in the present invention may also be a tumor-specific antigen (TSA) or a tumor associated antigen (TAA). TSA is unique to tumor cells and does not occur on other cells of the body. The TAA-associated antigen is not unique to tumor cells, and conversely, it is also expressed on normal cells under conditions in which the immune tolerance state to the antigen cannot be induced. Antigen expression on the tumor can occur under conditions that enable the immune system to respond to the antigen. TAA may be an antigen expressed on normal cells during embryonic development when the immune system is immature and unable to respond, or they may be antigens that normally exist at very low levels on normal cells but express on tumor cells at a higher level.

Including, but not limited to, examples of TSA or TAA antigens include the following: differentiation antigens such as MART-1/MelanA (MART-1), gp100 (Pmel 17), tyrosinase, TRP-1, TRP-2; and tumor-specificity lineage antigens such as MAGE-1, MAGE-3, BAGE, GAGE-1, GAGE-2, p15; overexpressed embryonic antigens such as CEA; overexpressed oncogenes and mutated tumor-inhibiting genes such as p53, Ras, HER-2/neu; unique tumor antigens produced by chromosomal translocations such as BCR-ABL, E2A-PRL, H4-RET, 1GH-IGK, MYL-RAR; and viral antigens such as Epstein Barr virus antigen EBVA and human papillomavirus (HPV) antigens E6 and E7. Other large group of, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, β-catenin, CDK4, Mum-1, p 15, p 16, 43-9F, 5T4, 791Tgp72, α-fetoprotein, β-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV 18, NB/70K, NY-CO-1, RCAS1, SDCCAG16, TA-90\Mac-2 binding protein\Cyclophilin C-related protein, TAAL6, TAG72, TLP and TPS.

In one embodiment, the tumor antigen referred to in the present invention may be a complex of MHC with the above-described antigenic peptide. These include, but are not limited to, HLA-GP100 complex, HLA-Mart1 complex, HLA-WT1 complex.

In one embodiment, the antigen-binding domain (R1, R3) in the main peptide chain or the antigen-binding domain (R4) in the co-peptide chain is an antibody, a ligand, a receptor, and a polypeptide that can bind to an antigen, or any combination thereof.

The antibody may be an intact peptide chain or a partial peptide of Ig, Fab, scFv or any combination thereof. The ligand or receptor can be its entire peptide chain, a partial peptide segment, or any combination thereof.

Wherein the co-peptide chain linkage domain (R2) and the main peptide chain linkage domain (R5) are a pair of polypeptides having a mutual binding function.

The polypeptides having a mutual binding function may be a pair of receptors and ligands which can bind to each other or a pair of antibodies and antigens which can bind to each other. Preferably, a pair of γc cytokines and their receptor subunits can be bound to each other, and IL15 and IL15Rα, IL4, and IL4R are preferably selected.

The individual functional domains of the main peptide chain and the co-peptide chain are linked by a polypeptide linker which is a glycine- and/or serine-rich sequence or a plurality of copy sequences rich in glycine and/or serine, and the polypeptide linker generally comprises 5-20 amino acid residues.

FIGURES

FIG. 1. A schematic diagram showing the molecular structure of a multifunctional protein. A: The multifunctional protein molecule is composed of a main peptide chain X and an auxiliary peptide chain Y, wherein the main peptide chain X includes an antigen binding domain R1, a co-peptide chain linkage domain R2, an antigen binding domain R3, and a co-peptide chain Y includes an antigen binding domain R4, the main peptide chain linkage domain R5; B: The multifunctional protein molecule is composed of a main peptide chain X and a co-peptide chain Y, wherein the main peptide chain X includes an antigen-binding domain R1, a co-peptide chain linkage domain R2, and an antigen-binding domain R3. The peptide chain Y comprises a main peptide chain linkage domain R5; C: The multifunctional protein molecule consists only of the main peptide chain X, wherein the main peptide chain X comprises an antigen binding domain R1, a co-peptide chain linkage domain R2, and an antigen binding domain R3.

Figure 2:
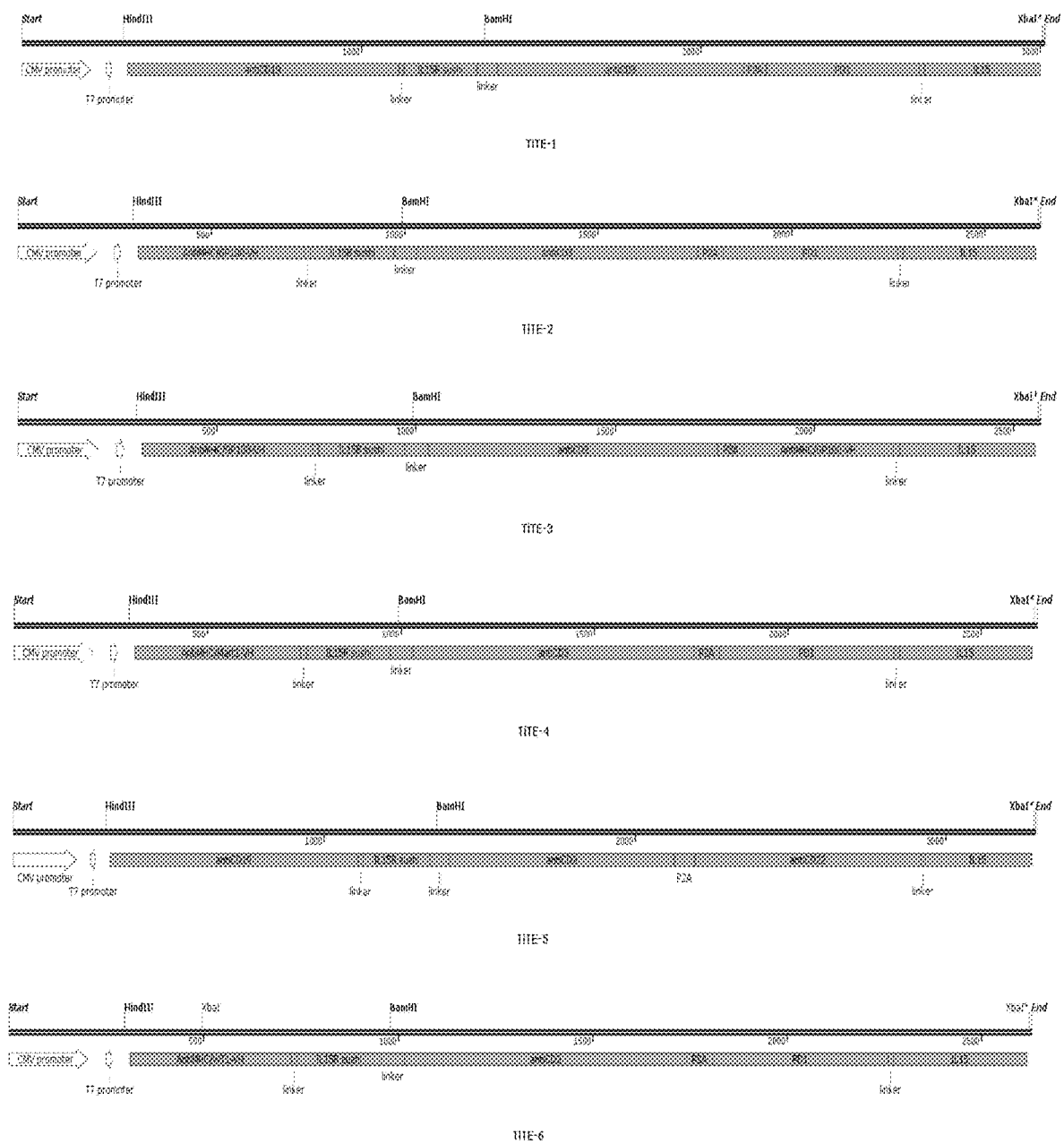
Figure 2:
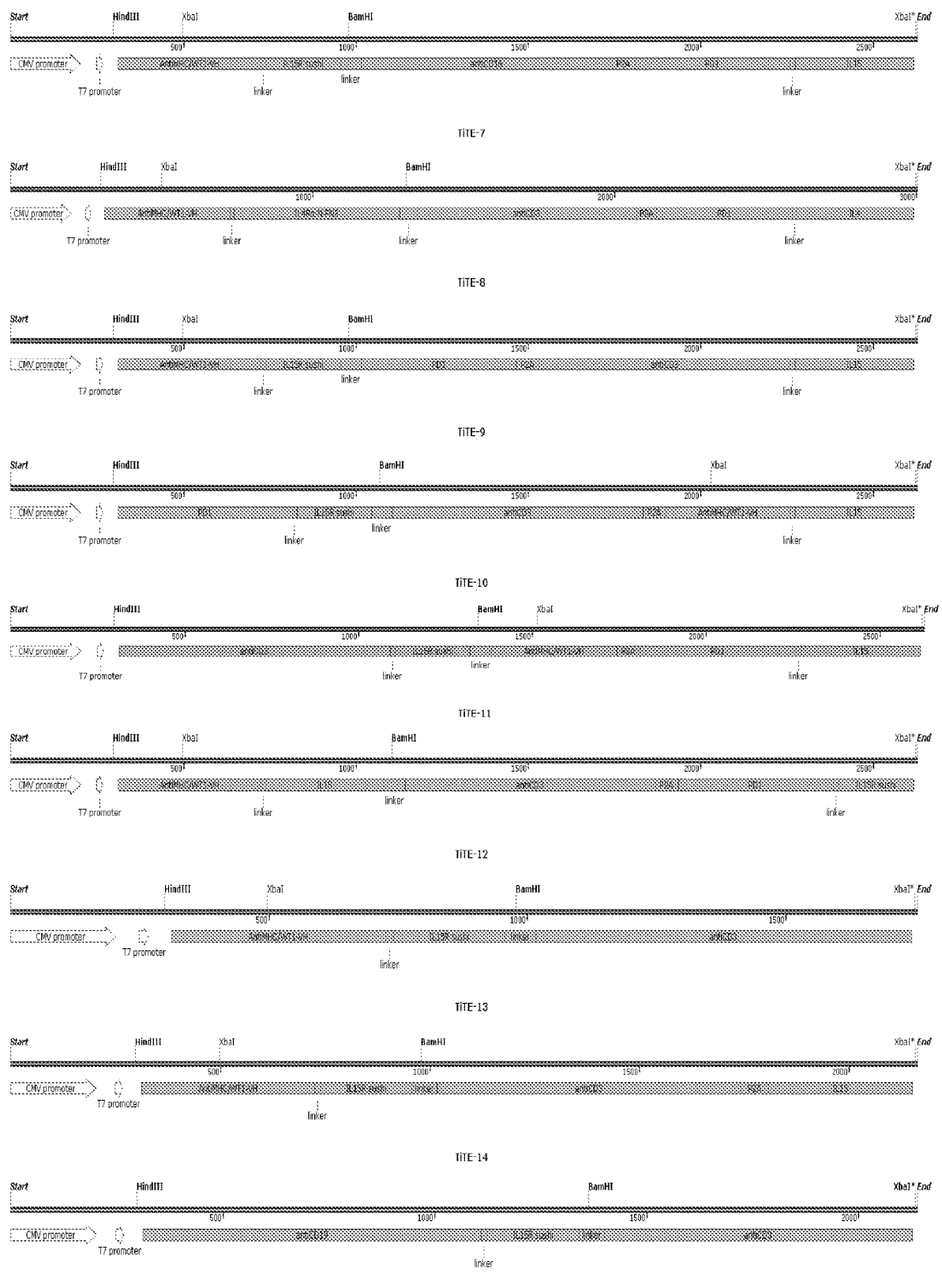
Figure 2:
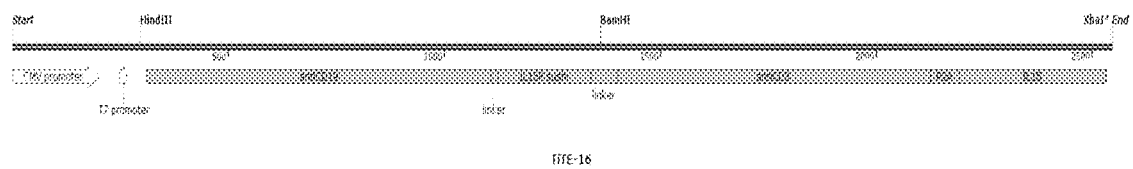

FIG. 2. The gene expression framework of the multifunctional protein molecule.

Figure 3:
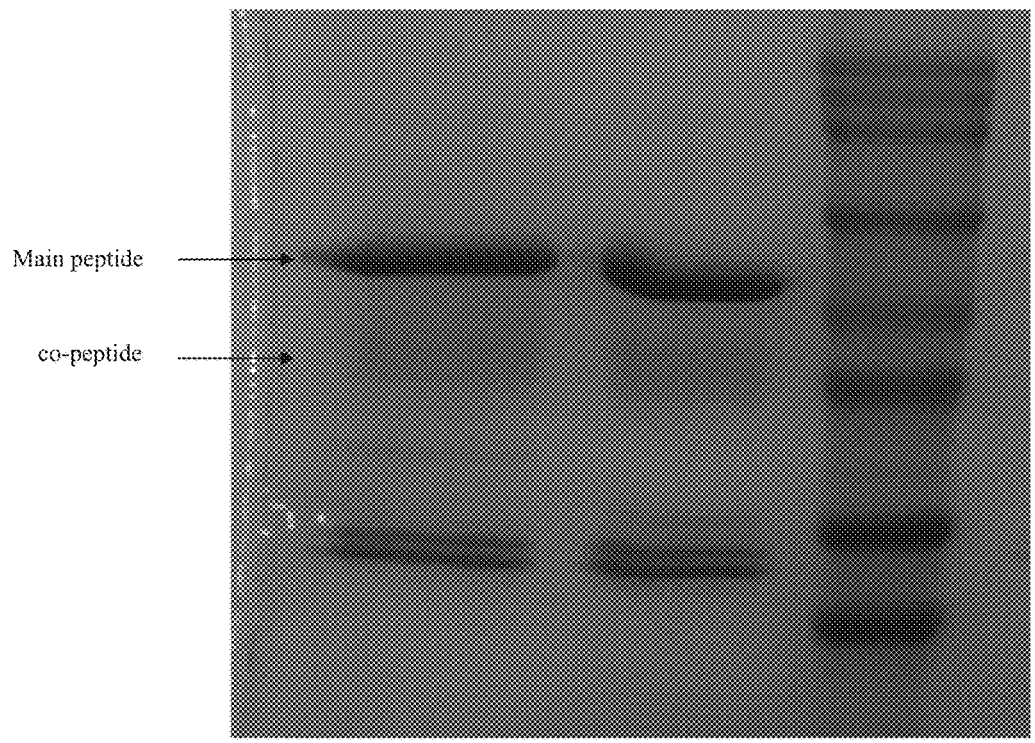

FIG. 3. The expressed and purified multifunctional protein molecules on SDS-PAGE. Lane 1: TiTE-1, main peptide chain about 65 KD, co-peptide chain about 30 KD; Lane 2: TiTE-6, main peptide chain about 65 KD, co-peptide chain about 30 KD; Lane 3: Protein marker, the molecular weight from top to bottom respectively as 160 KD, 120 KD, 100 KD, 70 KD, 50 KD, 40 KD, 30 KD, 25 KD.

Figure 4:
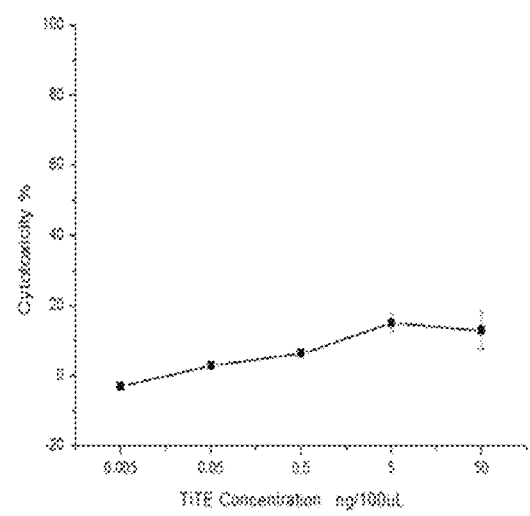
Figure 4:
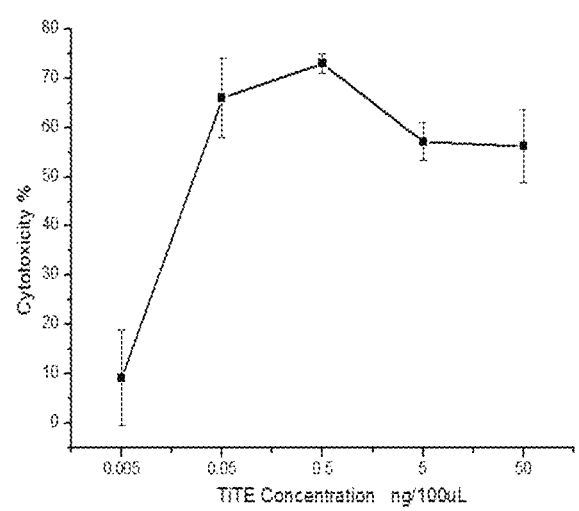
Figure 4:
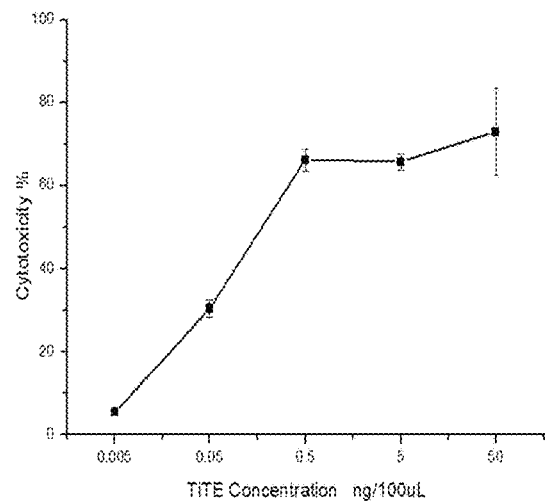
Figure 4:
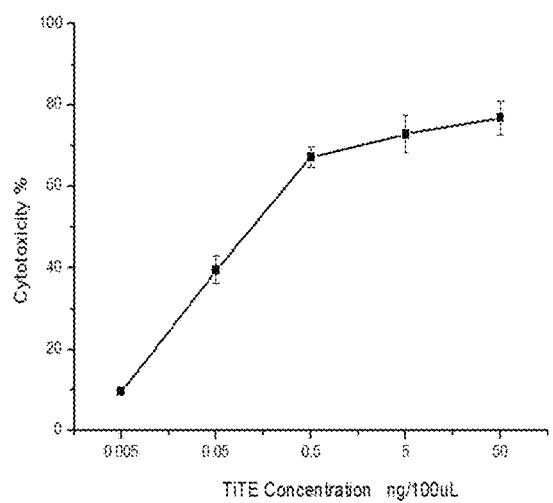
Figure 4:
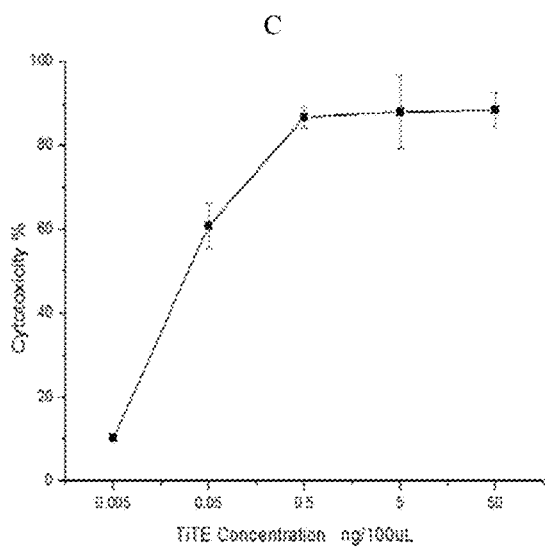
Figure 4:
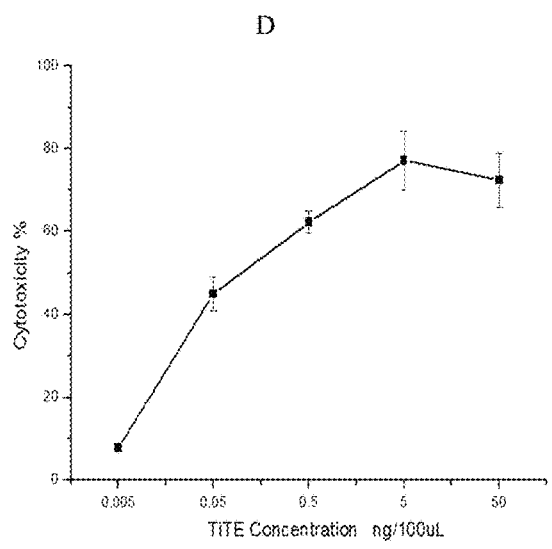

FIG. 4. The killing results of the multifunctional protein molecule TiTE-1, 15, 16, and 5: A, The negative control of TiTE-6 protein for killing malme-3M-CD19-luc; B, TiTE-1 protein for killing malme-3M-CD19-luc; C, TiTE-15 protein for killing malme-3M-CD19-luc; D, TiTE-16 protein for killing malme-3M-CD19-luc; E, TiTE-5 protein for killing malme-3M-CD19-luc; F, TiTE-5 protein for killing malme-3M-CD22-luc. It is demonstrated that the multi-functional proteins TiTE-1, 15, 16, and 5 provided by the present invention can kill tumor cells in vitro at a very low concentration, and it shows the best result when the concentration is used as 0.5-5 ng/10^6 cells.

Figure 5:
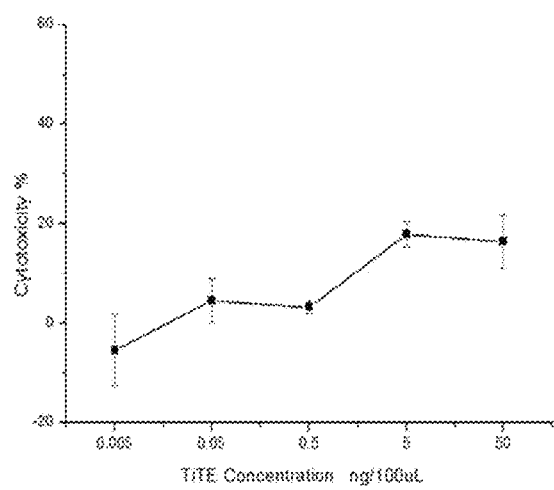
Figure 5:
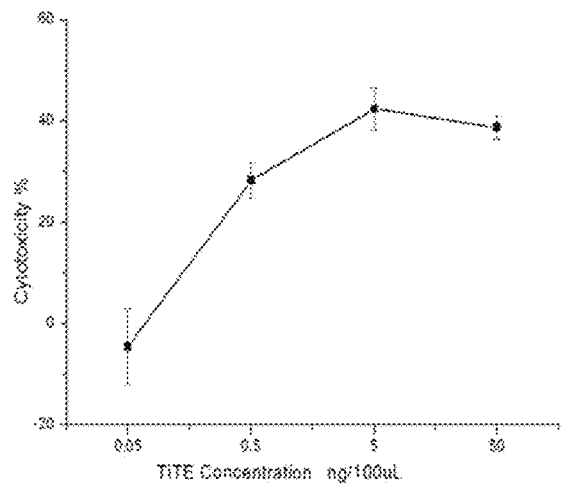
Figure 5:
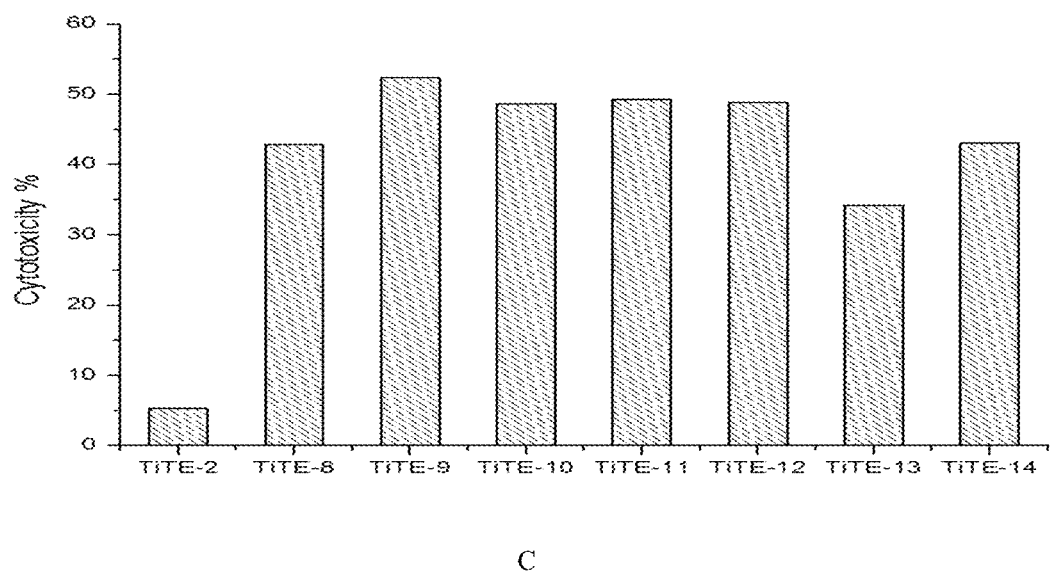

FIG. 5. The killing results of the multifunctional protein molecule TiTE-6, 8, 9, 10, 11, 12, 13, and 14 respectively: A, the negative control of TiTE-2 protein for killing BV173-luc; B, TiTE-6 protein for killing BV173-luc C, TiTE-8, 9, 10, 11, 12, 13, 14 proteins for killing BV173-luc. It was demonstrated that the multifunctional proteins TiTE-6, 8, 9, 10, 11, 12, 13, and 14 provided by the present invention shows killing ability for WT1-positive tumor cells.

Figure 6:
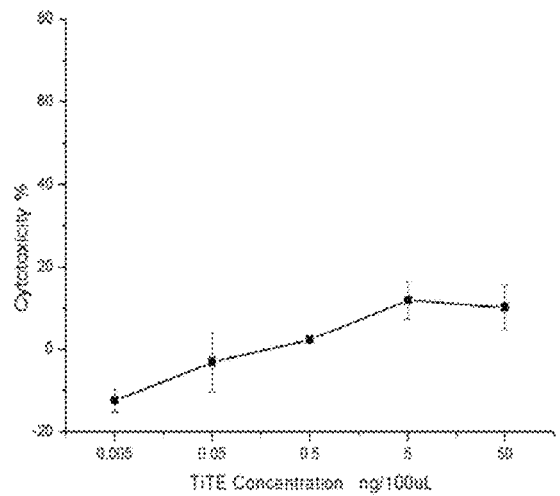
Figure 6:
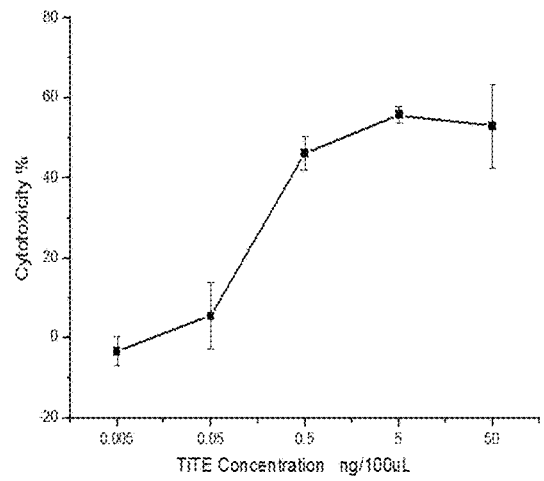
Figure 6:
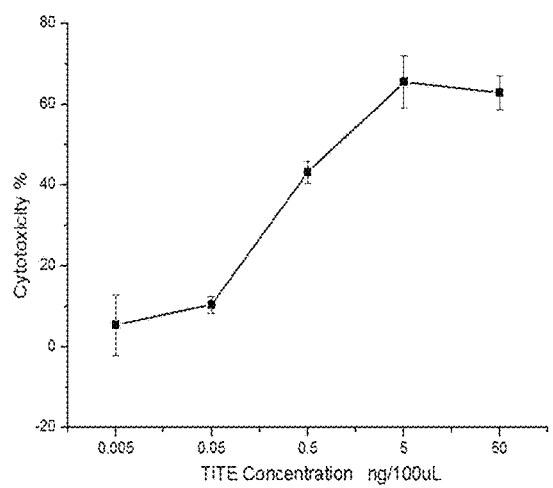
Figure 6:
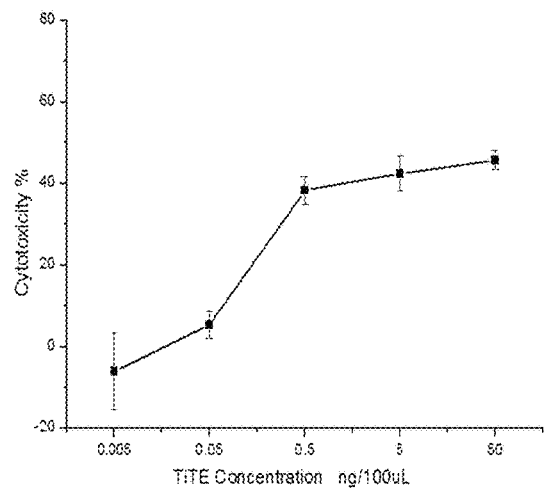

FIG. 6. The killing results of multifunctional protein molecules TiTE-2, 3, 4: A, the negative control TiTE-6 protein for killing malme-3M-luc; B, TiTE-2 protein for killing malme-3M-luc; C, TiTE-3 protein for killing malme-3M-luc; D, TiTE-4 protein for killing malme-3M-luc. It is demonstrated that the multifunctional proteins TiTE-2, 3, and 4 provided by the present invention can kill tumor cells expressing the intracellular antigen in vitro.

Figure 7:
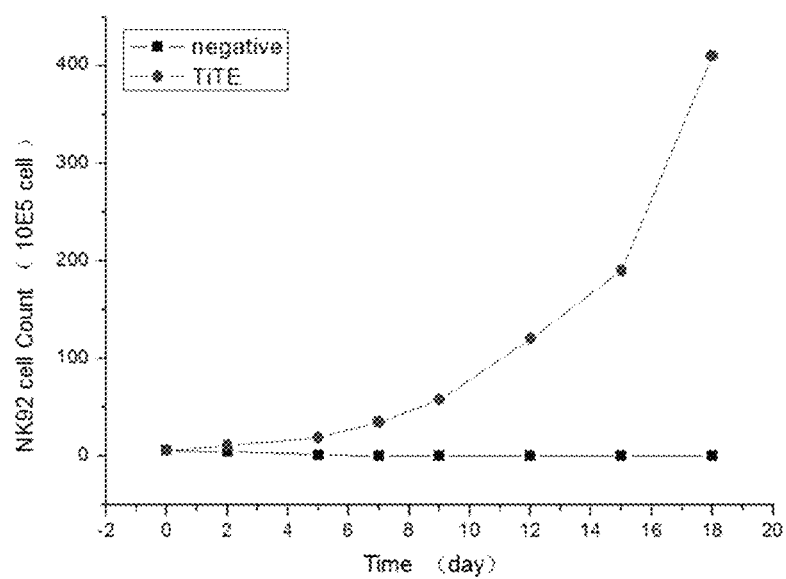

FIG. 7. The results of the stimulation of NK cells by multifunctional protein molecules. Almost all cells died after 5 days when the NK cell expansion was stimulated without any interleukin; NK cell expansion were obtained by the stimulation of the multi-functional proteins provided by the present invention, and cells were amplified about 140 times in 18 days.

Figure 8:
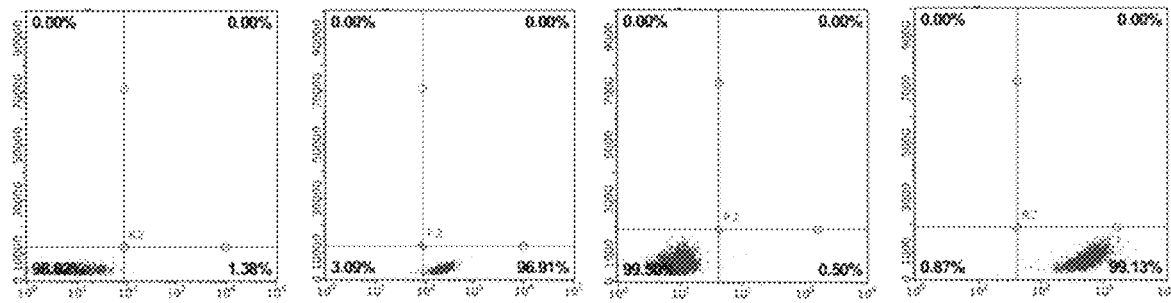
Figure 8:
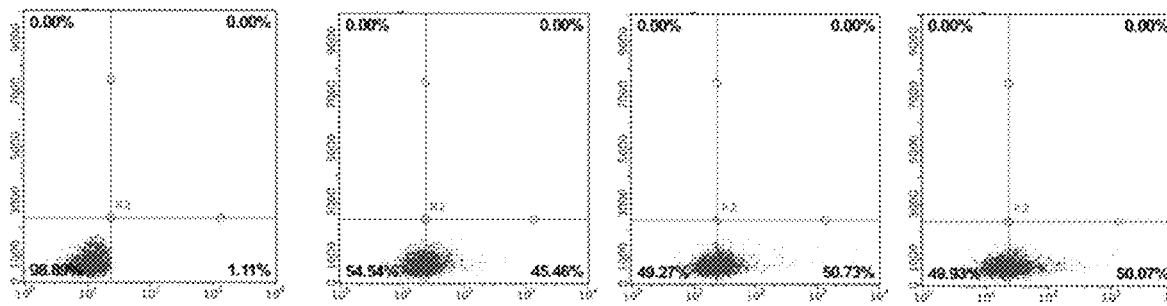
Figure 8:
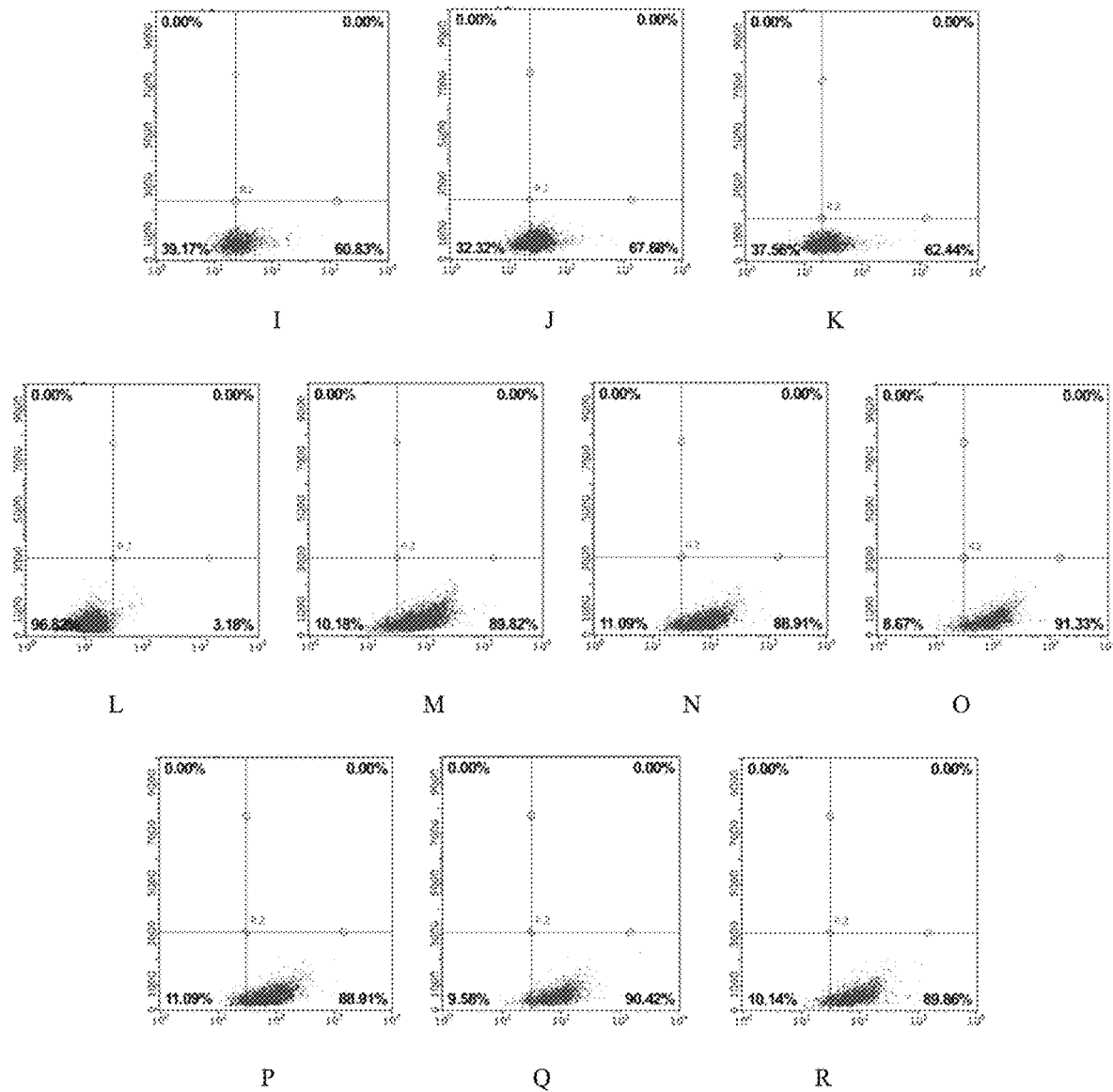

FIG. 8. FACS analysis with multifunctional protein molecules TiTE-1, 6, 8, 9, 10, 11, 12: A, The negative control with T cell alone; B, The experimental group of T cells with TiTE-1; C, The negative control with BV173 alone; The experimental group of TiTE-1 on BV173; E, The negative control with BV173; F, The experimental group of TiTE-6 on BV173; G, The experimental group of TiTE-8 on BV173; H, The experimental group of TiTE-9 on BV173; I, The experimental group of TiTE-10 on BV173; J, The experimental group of TiTE-11 on BV173; K, The experimental group of TiTE-12 on BV173; L, T cell negative control; M, The experimental group of TiTE-6 on T cell; N, The experimental group of TiTE-8 on T cell; 0, The experimental group of TiTE-9 on T cell; P, The experimental group of TiTE-10 on T Cell; Q, The experimental group of TiTE-11 on T cell; R, The experimental group of TiTE-12 on T cell. The experiments demonstrated that the multifunctional protein molecule TiTE-1 binds well to CD3 antigen and CD19 antigen respectively; the AntiMHC/WT1 and antiCD3 of TiTE-6, 8, 9, 10, 11, 12 have ability to bind to both intracellular antigen WT1 and CD3 antigen, respectively.

Figure 9:
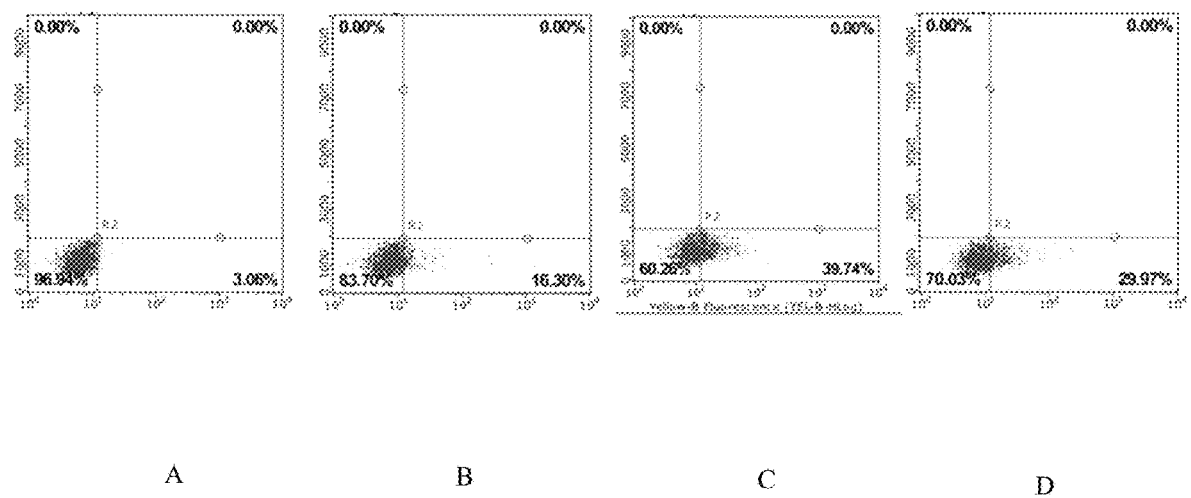
Figure 9:
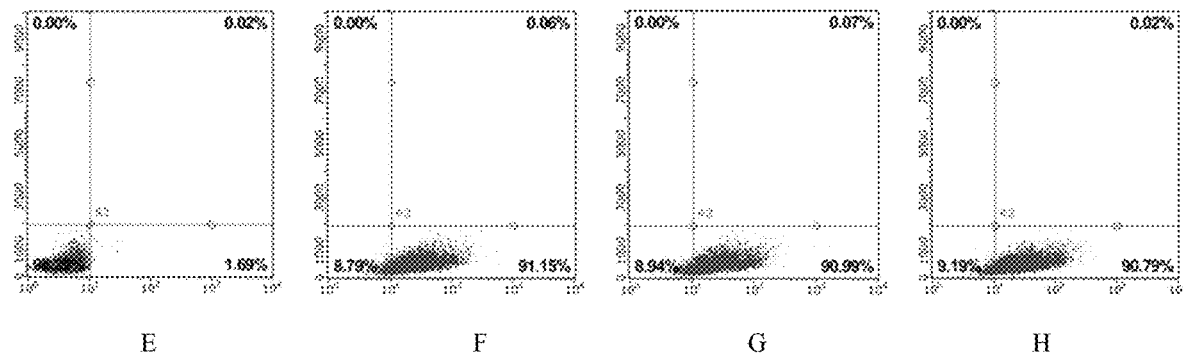

FIG. 9. FACS results of multifunctional protein molecules TiTE-2, 3, and 4: A, malme-3M negative control; B, The experimental group of TiTE-2 on malme-3M; C, The experimental group of TiTE-2 on malme-3M; D, The experimental group of TiTE-4 one malme-3M; E, T cell negative control; F, The experimental group of TiTE-2 on T cell; G, The experimental group of TiTE-3 on T cell; H, The experimental group of TiTE-4 on T cell. It can be seen from the figure that the multifunctional protein molecules TiTE-2, 3 bind well to the MHC/GP100 antigen and CD3 antigen, respectively, and TiTE-4 binds well to the MHC/Mart1 antigen and CD3 antigen.

Figure 10:
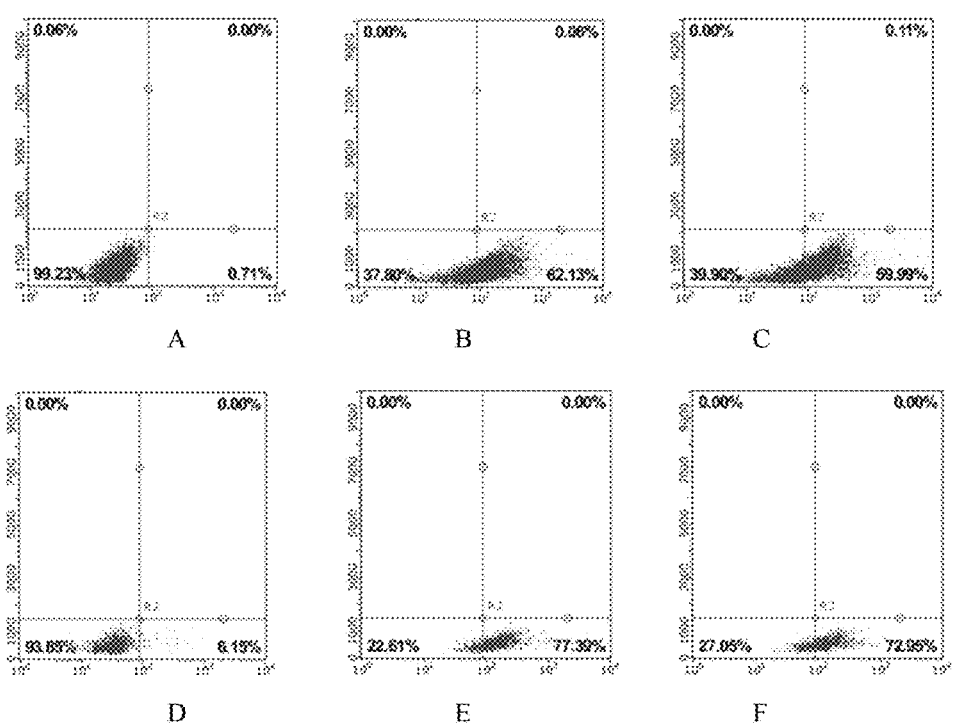

FIG. 10. FACS results of multifunctional protein molecules TiTE-15, 16: A, BV173 negative control; B, The experimental group of TiTE-15 on BV173; C, the experimental group of TiTE-16 on BV173; D, T cell negative control; E, The experimental group of TiTE-15 on T cell; F, The experimental group of TiTE-16 on T cell. It can be seen from the figure that the multifunctional protein molecules TiTE-15, 16 bind well to the CD19 antigen and the CD3 antigen, respectively.

Figure 11:
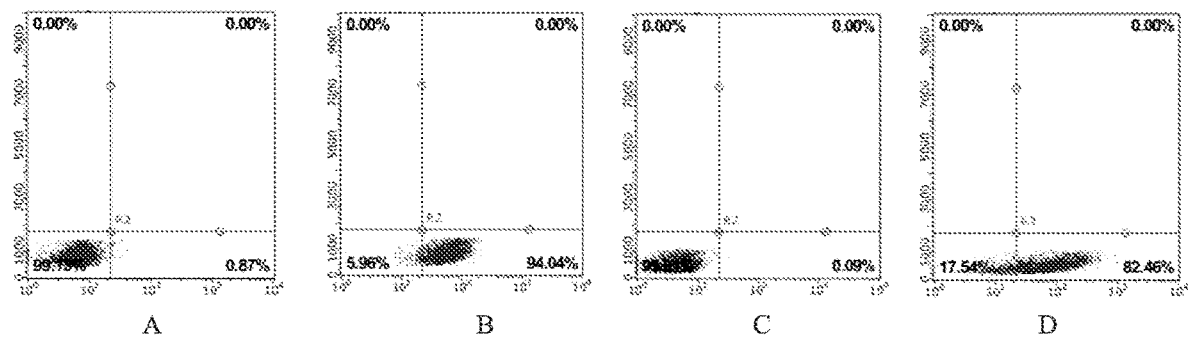
Figure 11:
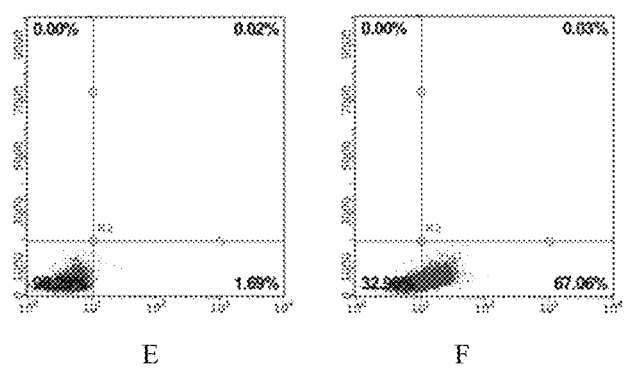

FIG. 11. FACS results of multifunctional protein molecule TiTE-5: A; malme-3M-CD19-Luc negative control; B, The experimental group of TiTE-5 on malme-3M-CD19-Luc; C, Negative control with malme-3M-CD22-Luc; D, The experimental group of TiTE-5 on malme-3M-CD22-Luc; E, T cell negative control; F, The experimental group of TiTE-5 on T cell; It can be seen from the figure that the multifunctional protein molecule TiTE-5 binds well to the CD19 antigen, CD20 antigen and CD3 antigen, respectively.

EXAMPLES

The experimental methods used in the following examples are conventional methods unless otherwise specified.

The materials, reagents and the like used in the following examples are commercially available unless otherwise specified.

Example 1. Construction of the Vector Expressing a Multifunctional Protein Molecule 1. Construction of the Novel Multifunctional Protein TiTE-1 Targeting to CD19-Positive Tumor Cells A novel multifunctional protein TiTE-1 targeting to CD19-positive tumor cells, which was fused by the main peptide chain X1 with the co-peptide chain Y1 to obtain a protein (FIG. 1).

The main peptide chain X1 included an antigen 1 binding domain R1, a cytokine or the cytokine binding domain of a cytokine receptor R2 and an antigen 2 binding domain R3; The co-peptide chain Y1 included an antigen 3 binding domain R4 and a main peptide chain X linkage domain R5.

The antigen-binding domain (R1) of the main peptide chain (X1) was selected from antiCD19-ScFv (SEQ ID NO. 1), the co-peptide chain linkage domain (R2) was selected from IL15Rαsushi (SEQ ID NO. 2), and the antigen-binding domain (R3) is selected from antiCD3-ScFv (SEQ ID NO. 3); The extracellular domain of the receptor PD1 of PDL1 and PDL2 (SEQ ID NO. 4) was selected as the antigen binding domain (R4) of the co-peptide chain (Y1), and IL15 (SEQ ID NO. 5) was selected as the primary peptide chain domain (R5).

2. The Signal Peptide (Amino Acid Sequence: MALPVTALLLPLALLLHAARP (SEQ ID NO: 51)), HindIII restriction site was added to the 5' end of the main peptide chain, and the linker peptide between the co-peptide chain domain of the main peptide chain (R2: L15Rαsushi) and the antigen binding domain (R3: antiCD3-ScFv) contained a BamHI restriction site; a P2A peptide was added between the 3' end of the main peptide chain and the 5' end of the co-peptide chain (amino acid sequence: GSGATNFSLLKQAGDVEENPGP (SEQ ID NO: 52)); Xba I of restriction site was added to the 3' end of the co-peptide chain.

3. The antiCD19-IL15Rαsushi fragment, antiCD3 fragment and P2A-PD1-IL15 fragment were PCR amplified and run on nucleic acid gel electrophoresis; overlapping PCR amplified antiCD3-P2A-PD1-IL15 fragment on nucleic acid gel electrophoresis. The antiCD19-IL15Rαsushi fragment was cleaved using HindIII and BamHI. AntiCD3-P2A-PD1-IL15 was cut using BamHI and Xba I; the vector PCDNA3.1 (Invitrogen) was cleaved using HindIII and Xba I.

4. The target fragments were recovered by gel electrophoresis, and three fragments recovered were ligated and transformed, and the clones were selected and sequenced, and finally the target plasmid PCDNA3.1-TiTE-1 was obtained.

The recombinant vector PCDNA3.1-TiTE-1 is an expression cassette for the expression of the multifunctional protein TiTE-1 targeting CD19-positive tumor cells (the nucleotide sequence of the expression cassette is composed of the nucleotide sequence encoding the main peptide chain X1 (SEQ ID NO. 6) and the nucleotide sequence (SEQ ID NO. 7) encoding the co-peptide chain Y1, and the last nucleotide of the SEQ ID NO. 6 is immediately adjacent to the first nucleotide of the SEQ ID NO. 7) replaces the fragment between HindIII and XbaI of PCDNA3.1 vector (Invitrogen, USA), the resulting recombinant vector was obtained to express a functional multifunctional protein TiTE-1 consisting of a main peptide chain X1 (SEQ ID NO. 8) and a co-peptide chain Y1 (SEQ ID NO. 9).

5. According to the above steps, the expression vectors were constructed for the multifunctional proteins TiTE-2, TiTE-3, TiTE-4, TiTE-5, TiTE-6, TiTE-7, TiTE-8, TiTE-9, TiTE-10, TiTE-11, TiTE-12; The expression vectors of TiTE-13, TiTE-14, TiTE-15, and TiTE-16 were constructed in a similar manner, and the structures thereof are shown in Table 1 below, and the expression framework is shown in FIG. 2.

TABLE 1 the structure of multifunctional proteins

| | Antigen binding domain R1 | Co-peptide linkage domain R2 | Antigen binding domain R3 | Antigen binding domain R4 | Main peptide chain linkage domain R5 |
|---|---|---|---|---|---|
| TiTE-1 | AntiCD19-ScFv | IL15Rαsushi | AntiCD3-ScFv | Extracellular region of PD1 | IL15 |
| TiTE-2 | AntiMHC/GP100-VHH | IL15Rαsushi | AntiCD3-ScFv | Extracellular region of PD1 | IL15 |
| TiTE-3 | AntiMHC/GP100-VHH | IL15Rαsushi | AntiCD3-ScFv | AntiMHC/GP100-VHH | IL15 |
| TiTE-4 | AntiMHC/Mart 1-VHH | IL15Rαsushi | AntiCD3-ScFv | Extracellular region of PD1 | IL15 |
| TiTE-5 | AntiCD19-ScFv | IL15Rαsushi | AntiCD3-ScFv | AntiCD22-ScFv | IL15 |
| TiTE-6 | AntiMHC/WT1-VH | IL15Rαsushi | AntiCD3-ScFv | Extracellular region of PD1 | IL15 |
| TiTE-7 | AntiMHC/WT1-VH | IL15Rαsushi | AntiCD16-ScFv | Extracellular region of PD1 | IL15 |
| TiTE-8 | AntiMHC/WT1-VH | IL4Rα-N-FN3 | AntiCD3-ScFv | Extracellular region of PD1 | IL4 |
| TiTE-9 | AntiMHC/WT1-VH | IL15Rαsushi | AntiCD3-ScFv | Extracellular region of PD1 | IL15 |
| TiTE-10 | Extracellular region of PD1 | IL15Rαsushi | AntiCD3-ScFv | AntiMHC/WT1-VH | IL15 |
| TiTE-11 | AntiCD3-ScFv | IL15Rαsushi | AntiMHC/WT1-VH | Extracellular region of PD1 | IL15 |
| TiTE-12 | AntiMHC/WT1-VH | IL15 | AntiCD3-ScFv | Extracellular region of PD1 | IL15 Rαsushi |
| TiTE-13 | AntiMHC/WT1-VH | IL15Rαsushi | AntiCD3-ScFv | — | — |
| TiTE-14 | AntiMHC/WT1-VH | IL15Rαsushi | AntiCD3-ScFv | — | IL15 |

TABLE 1-continued the structure of multifunctional proteins

|  | Antigen binding domain R1 | Co-peptide linkage domain R2 | Antigen binding domain R3 | Antigen binding domain R4 | Main peptide chain linkage domain R5 |
|---|---|---|---|---|---|
| TiTE-15 | AntiCD19-ScFv | IL15Rαsushi | AntiCD3-ScFv | — | — |
| TiTE-16 | AntiCD19-ScFv | IL15Rαsushi | AntiCD3-ScFv | — | IL15 |

Wherein, the AntiMHC/GP100-VHH comprises the amino acid sequence of SEQ ID NO. 10.

The AntiMHC/Mart1-VHH comprises the amino acid sequence of SEQ ID NO. 11.

The AntiMHC/WT1-VH comprises the amino acid sequence of SEQ ID NO. 12.

The IL4Rα-N-FN3 comprises the amino acid sequence of SEQ ID NO. 13.

The AntiCD16-ScFv comprises the amino acid sequence of SEQ ID NO. 14.

The AntiCD22-ScFv comprises the amino acid sequence of SEQ ID NO. 15.

The IL4 comprises the amino acid sequence of SEQ ID NO. 16.

The main peptide chain of TiTE-2 comprises the amino acid sequence of SEQ ID NO. 17, and the co-peptide chain comprises the amino acid sequence of SEQ ID NO. 9.

The main peptide chain of TiTE-3 comprises the amino acid sequence of SEQ ID NO. 17, and the co-peptide chain comprises the amino acid sequence of SEQ ID NO. 18.

The main peptide chain of TiTE-4 comprises the amino acid sequence of SEQ ID NO. 19, and the co-peptide chain comprises the amino acid sequence of SEQ ID NO. 9.

The main peptide chain of TiTE-5 comprises the amino acid sequence of SEQ ID NO. 8, and the co-peptide chain comprises the amino acid sequence of SEQ ID NO. 20.

The main peptide chain of TiTE-6 comprises the amino acid sequence of SEQ ID NO. 21, and the co-peptide chain comprises the amino acid sequence of SEQ ID NO. 9.

The main peptide chain of TiTE-7 comprises the amino acid sequence of SEQ ID NO. 22, and the co-peptide chain comprises the amino acid sequence of SEQ ID NO. 9.

The main peptide chain of TiTE-8 comprises the amino acid sequence of SEQ ID NO. 23, and the co-peptide chain comprises the amino acid sequence of SEQ ID NO. 24.

The main peptide chain of TiTE-9 comprises the amino acid sequence of SEQ ID NO. 25, and the co-peptide chain comprises the amino acid sequence of SEQ ID NO. 26.

The main peptide chain of TiTE-10 comprises the amino acid sequence of SEQ ID NO. 27, and the co-peptide chain comprises the amino acid sequence of SEQ ID NO. 28.

The main peptide chain of TiTE-11 comprises the amino acid sequence of SEQ ID NO. 29, and the co-peptide chain comprises the amino acid sequence of SEQ ID NO. 9.

The main peptide chain of TiTE-12 comprises the amino acid sequence of SEQ ID NO. 30, and the co-peptide chain comprises the amino acid sequence of SEQ ID NO. 31.

TiTE-13 is the main peptide chain, and the main peptide chain comprises the amino acid sequence of SEQ ID NO. 21.

The main peptide chain of TiTE-14 comprises the amino acid sequence of SEQ ID NO. 21, and the co-peptide chain comprises the amino acid sequence of SEQ ID NO. 5.

TiTE-15 is a main peptide chain, and it comprises the amino acid sequence of SEQ ID NO. 8.

The main peptide chain of TiTE-16 comprises the amino acid sequence of SEQ ID NO. 8, and the co-peptide chain comprises the amino acid sequence of SEQ ID NO. 5.

The encoding nucleic acid sequence expressing TiTE-2 is composed of a main peptide chain encoding nucleic acid sequence and a co-peptide chain encoding nucleic acid sequence, and the last base of the 3' end of the main peptide chain encoding nucleic acid sequence is next to the 1st base of the 5' end of the co-peptide chain encoding nucleic acid sequence. wherein the main peptide chain encoding nucleic acid sequence is SEQ ID NO. 35, and the co-peptide chain encoding nucleic acid sequence is SEQ ID NO. 7.

The encoding nucleic acid sequence expressing TiTE-3 is composed of a main peptide chain encoding nucleic acid sequence and a co-peptide chain encoding nucleic acid sequence, and the last base of the 3' end of the main peptide chain encoding nucleic acid sequence is next to the 1st base of the 5' end of the co-peptide chain encoding nucleic acid sequence. wherein the main peptide chain encoding nucleic acid sequence is SEQ ID NO. 35, and the co-peptide chain encoding nucleic acid sequence is SEQ ID NO. 36.

The encoding nucleic acid sequence expressing TiTE-4 is composed of a main peptide chain encoding nucleic acid sequence and a co-peptide chain encoding nucleic acid sequence, and the last peptide of the 3' end of the main peptide chain encoding nucleic acid sequence is next to the 1st base of the 5' end of the co-peptide chain encoding nucleic acid sequence. wherein the main peptide chain encoding nucleic acid sequence is SEQ ID NO. 37, and the co-peptide chain encoding nucleic acid sequence is SEQ ID NO. 7.

The encoding nucleic acid sequence expressing TiTE-5 is composed of a main peptide chain encoding nucleic acid sequence and a co-peptide chain encoding nucleic acid sequence, and the last base of the 3' end of the main peptide chain encoding nucleic acid sequence is next to the 1st base of the 5' end of the co-peptide chain encoding nucleic acid sequence; wherein the main peptide chain encoding nucleic acid sequence is SEQ ID NO. 6, and the co-peptide chain encoding nucleic acid sequence is SEQ ID NO. 38;

The encoding nucleic acid sequence expressing TiTE-6 is composed of a main peptide chain encoding nucleic acid sequence and a co-peptide chain encoding nucleic acid sequence, and the last base of the 3' end of the main peptide chain encoding nucleic acid sequence is next to the 1st base of the 5' end of the co-peptide chain encoding nucleic acid sequence; wherein the main peptide chain encoding nucleic acid sequence is SEQ ID NO. 39, and the co-peptide chain encoding nucleic acid sequence is SEQ ID NO. 7.

The encoding nucleic acid sequence expressing TiTE-7 is composed of a main peptide chain encoding nucleic acid sequence and a co-peptide chain encoding nucleic acid sequence, and the last peptide of the 3' end of the main peptide chain encoding nucleic acid sequence is next to the 1st base of the 5' end of the co-peptide chain encoding nucleic acid sequence; wherein the main peptide chain encoding nucleic acid sequence is SEQ ID NO. 40, and the co-peptide chain encoding nucleic acid sequence is SEQ ID NO. 7.

The encoding nucleic acid sequence expressing TiTE-8 is composed of a main peptide chain encoding nucleic acid sequence and a co-peptide chain encoding nucleic acid, and the last base of the 3' end of the main peptide chain encoding nucleic acid sequence is next to the 1st base of the 5' end of the co-peptide chain encoding nucleic acid sequence; wherein the main peptide chain encoding nucleic acid sequence is SEQ ID NO. 41, and the co-peptide chain encoding nucleic acid sequence is SEQ ID NO. 42.

The encoding nucleic acid sequence expressing TiTE-9 is composed of a main peptide chain encoding nucleic acid sequence and a co-peptide chain encoding nucleic acid sequence, and the last base of the 3' end of the main peptide chain encoding nucleic acid sequence is next to the 1st base of the 5' end of the co-peptide chain encoding nucleic acid sequence; wherein the main peptide chain encoding nucleic acid sequence is SEQ ID NO. 43, and the co-peptide chain encoding nucleic acid sequence is SEQ ID NO. 44.

The encoding nucleic acid sequence expressing TiTE-10 is composed of a main peptide chain encoding nucleic acid sequence and a co-peptide chain encoding nucleic acid sequence, and the last base of the 3' end of the main peptide chain encoding nucleic acid sequence is next to the 1st base of the 5' end of the co-peptide chain encoding nucleic acid sequence; wherein the main peptide chain encoding nucleic acid sequence is SEQ ID NO. 45, and the co-peptide chain encoding nucleic acid sequence is SEQ ID NO. 46.

The encoding nucleic acid sequence expressing TiTE-11 is composed of a main peptide chain encoding nucleic acid sequence and a co-peptide chain encoding nucleic acid sequence, and the last peptide of the 3' end of the main peptide chain encoding nucleic acid sequence is next to the 1st base of the 5' end of the co-peptide chain encoding nucleic acid sequence; wherein the main peptide chain encoding nucleic acid sequence is SEQ ID NO. 47, and the co-peptide chain encoding nucleic acid sequence is SEQ ID NO. 7.

The encoding nucleic acid sequence expressing TiTE-12 is composed of a main peptide chain encoding nucleic acid sequence and a co-peptide chain encoding nucleic acid sequence, and the last base of the 3' end of the main peptide chain encoding nucleic acid sequence is next to the 1st base of the 5' end of the co-peptide chain encoding nucleic acid sequence; wherein the main peptide chain encoding nucleic acid sequence is SEQ ID NO. 48, and the co-peptide chain encoding nucleic acid sequence is SEQ ID NO. 49.

The coding nucleic acid sequence expressing TiTE-13 is SEQ ID NO. 39.

The encoding nucleic acid sequence expressing TiTE-14 is composed of a main peptide chain encoding nucleic acid sequence and a co-peptide chain encoding nucleic acid sequence, and the last base of the 3' end of the main peptide chain encoding nucleic acid sequence is next to the 1st base of the 5' end of the co-peptide chain encoding nucleic acid sequence; wherein the main peptide chain encoding nucleic acid sequence is SEQ ID NO. 39, and the co-peptide chain encoding nucleic acid sequence is SEQ ID NO. 50.

The nucleic acid sequence encoding TiTE-15 is SEQ ID NO. 6.

The encoding nucleic acid sequence expressing TiTE-16 is composed of a main peptide chain encoding nucleic acid sequence and a co-peptide chain encoding nucleic acid sequence, and the last peptide of the 3' end of the main peptide chain encoding nucleic acid sequence is next to the 1st base of the 5' end of the co-peptide chain encoding nucleic acid sequence; wherein the main peptide chain encoding nucleic acid sequence is SEQ ID NO. 6, the co-peptide chain encoding nucleic acid sequence is SEQ ID NO. 50.

To make recombinant vectors from PCDNA3.1-TiTE-2 to PCDNA3.1-TiTE-16 PCDNA3.1 vector is cut by HindIII and XbaI and the corresponding nucleic acid sequence from the nucleic acid sequence expressing TiTE-2 to TiTE-16 is inserted into PCDNA3.1 respectively.

Example 2: The Expression and Purification of Multi-Targeting Functional Proteins 1. 293F (in vitrogen) was cultured at 37° C., 8% CO2, 120 rpm until the cell density reached to 1×10^6 cell/ml. 2. The vector PCDNA3.1-TiTE-1 constructed in Example 1 was transfected into the cells of the above 1 using PEI and the concentration of plasmid used was 1 mg/L, and PEI concentration was 3 mg/L. The cells were incubated for 5-6 days at 37° C., 8% CO2, 120 rpm.

3. The culture media of the above 2 was centrifuged at 4000 rpm, and the supernatant was collected, and the protein was bound to Protein/cap to L beads and eluted with 500 μL of 0.1Mof Gly-HCl, pH 2.6-3.0, and finally the eluate was collected.

4. The proteins were detected on SDS-PAGE (FIG. 3). It can be seen that the target proteins of about 65 KD and 30 KD were obtained, representing the main peptide chain X and the co-peptide chain Y of the multifunctional protein molecule TiTE-1.

5. The same method was used to express and purify TiTE-2, TiTE-3, TiTE-4, TiTE-5, TiTE-7, TiTE-8, TiTE-9, TiTE-10, TiTE-11, TiTE-12, etc. multi-functional proteins.

Example 3: Multi-Functional Proteins TiTE-1, 15, 16 Mediated T Cell Killing CD19+Target Cells In Vitro 1. 1×10^4 of target cells, malme-3M-CD19-luc obtained by transfecting CD19 antigen gene (the nucleic acid sequence is SEQ ID NO. 32) and Luc gene (the nucleic acid sequence is SEQ ID NO. 33) into the Malme-3M purchased from ATCC to express CD19 antigen and the Luc protein, in 50 μL were plated in a 96-well plate, and cultured at 37° C., 5% CO2 for 18-20 h.

2. After the cells attached to the wall, the medium was aspirated and discarded, and 50 μL of fresh medium was added and the cells were cultured at 37° C., 5% CO2 for 1-3 h.

3, The target protein TiTE-1 obtained in Example 2 was stepwise diluted to different concentrations of 50, 5, 0.5, 0.05, 0.005 ng/μL respectively.

On experimental group: 50 μL of 1×10^5 of T cells, which were derived from mononuclear cell-rich white membrane layer of normal human peripheral blood by density gradient centrifugation, and stimulated by OKT3 (50 ng/mL) and IL2 (300 IU/mL) for 14 days, were added to 50, 5 0.5, 0.05, and 0.005 ng of TiTe-1, the target protein obtained in Example 2 and were incubated further for 1-2 h at 37° C. to obtain T cells incubated with the antibody.

On negative control group: 50, 5, 0.5, 0.05, 0.005 ng of a bispecific control antibody (TiTE-6) with no killing effect on the target cells were added to 50 μL of 1×10^5 T cells, respectively, and incubate at 37° C. for 1-2 h.

4. 50 μL of T cells incubated with the antibody were added to a 96-well plate with added target cells, and incubate at 37° C., 5% CO2 for 22-24 h.

5, 100 μL of 1% Triton lysate was added onto each well, repeatedly blew cells, and stood for 3-5 min, the cells were completely lysed; 50 μL of lysate was added into a black 96-well plate, 50 μL substrate (300 m/mL Luc and 2 mg/mL ATP was mixed in a volume ratio of 3:1) was added and the fluorescence value on each well was quickly measured.

6. The killing efficiency was calculated as follows: the killing efficiency={(negative control fluorescence value−experimental group fluorescence value)/negative control fluorescence value}×100%.

The result is shown in FIG. 4B. It can be seen that the multifunction protein TiTE-1 by the present invention can kill CD19-positive tumor cells in vitro at a very low concentration compared with the control group in FIG. 4A. The optimal killing effect in vitro can be obtained at a concentration of 0.5-5 ng/10^6 cells.

7. In the same way, TiTE-15 and TiTE-16 killing experiments were carried out to verify that the tumor cells were killed by using a very low concentration of a multifunctional protein.

The results are shown in FIGS. 4C and 4D. It can be seen that multifunctional proteins TiTE-15 and 16 by the present invention could kill tumor cells in vitro at a very low concentration, and the optimal concentration was 0.5-5 ng/10^6 cells.

8. In the same manner, TiTE-5 killing experiment was carried out malme-3M-CD19-luc and malme-3M-CD22-luc by transfecting a CD22 antigen gene (SEQ ID NO. 34) and a Luc gene (SEQ ID NO. 33) into the genome of ATCC-purchased Malme-3M were used as the target cells. The results are shown in FIGS. 4E and 4F. It can be seen that the multifunctional protein TiTE-5 provided by the present invention has killing ability on CD19 and CD22 positive cells. The tumor cells can be killed in vitro at a very low concentration, and the optimal killing effect was obtained when the concentration is 0.5-5 ng/10^6 cells.

Example 4: Multi-Functional Protein Molecule TiTE-6, 8, 9, 10, 11, 12, 13, 14 Mediate T Cell Killing of WT1 Positive Target Cells In Vitro 1. 1×10^4 of target cell BV173 (ATCC purchased BV173 transfected by Luc gene (SEQ ID NO. 33)) in 50 μL was plated in a 96-well plate, and cultured at 37° C., 5% CO2 for 1-2 h.

2, The target protein TiTE-6 obtained in Example 2 was stepwise diluted to different concentrations of 50, 5, 0.5, 0.05 ng/μL.

On experimental group: 50 uL of 1×10^5 of T cells, which were derived from mononuclear cell-rich white membrane layer of normal human peripheral blood by density gradient centrifugation, and stimulated by OKT3 (50 ng/mL) and IL2 (300 IU/mL) for 14 days, were added to 50, 5 0.5, 0.05, and 0.005 ng of TiTe-6, the target protein obtained in Example 2 and were incubated further for 1-2 h at 37° C. to obtain T cells incubated with the antibody.

On negative control group: 50, 5, 0.5, 0.05, 0.005 ng of a bispecific control antibody (TiTE-2) with no killing effect on the target cells were added to 50 μL of 1×10^5 T cells, respectively, and incubate at 37° C. for 1-2 h.

3. 50 μL of T cells incubated with the antibody was added to a 96-well plate with target cells, and incubated at 37° C., 5% CO2 for 22-24 h.

4. 100 μL of 1% Triton lysate was added onto each well, repeatedly blew cells, and stood for 3-5 min, the cells were completely lysed; 50 μL of lysate was added into a black 96-well plate, 50 μuL substrate (300 m/mL Luc and 2 mg/mL ATP was mixed in a volume ratio of 3:1) was added and the fluorescence value on each well was quickly measured.

5. The killing efficiency was calculated as follows: the killing efficiency={(negative control fluorescence value−experimental group fluorescence value)/negative control fluorescence value}×100%.

The result is shown in FIG. 5B. It can be seen that the multifunctional protein TiTE-6 provided by the present invention can kill tumor cells at a very low concentration.

6. The killing experiments of TiTE-8, 9, 10, 11, 12, 13, and 14 were carried out in the same manner, and the effective target ratio was 10:1, and the antibody concentration was 5 ng of the corresponding antibody in each case. The experimental results are shown in FIG. 5C. It can be seen that WT1 positive tumor cells could be killed by multi-functional proteins provided by the present invention are killed.

Example 5: Multi-Functional Protein TiTE-2, 3, 4 Mediate T Cell Killing for the Target Cells In Vitro 1. 50 μL of 1×10^4 target cell malme-3M-luc (obtained by transfection of Luc gene into malme-3M purchased by ATCC) was plated in a 96-well plate and cultured at 37° C., 5% CO2 for 18-20 h.2. After the cells attached to the wall, the medium was aspirated and discarded, and 50 μL of fresh medium was added and incubated at 37° C., 5% CO2 for 1-3 h.

3, TiTE-2, 3, 4 obtained in Example 2 were stepwise diluted to different concentrations of 50, 5, 0.5, 0.05, 0.005 ng/μL.

On experimental group: 50 μL of 1×10^5 of T cells, which were derived from mononuclear cell-rich white membrane layer of normal human peripheral blood by density gradient centrifugation, and stimulated by OKT3 (50 ng/mL) and IL2 (300 IU/mL) for 14 days, were added to 50, 5 0.5, 0.05, and 0.005 ng of TiTe-2, 3, 4, the target proteins obtained in Example 2. The cells with the proteins were incubated further for 1-2 h at 37° C. to obtain T cells incubated with the antibody.

On negative control group: 50, 5, 0.5, 0.05, 0.005 ng of a bispecific control antibody (TiTE-6) with no killing effect on the target cells were added to 50 μL of 1×10^5 T cells, respectively, and incubate at 37° C. for 1-2 h.

4. 50 μL of T cells incubated with the antibody was added to a 96-well plate plated with target cells, and incubate at 37° C., 5% CO2 for 22-24 h.

5, 100 μL of 1% Triton lysate was added onto each well, repeatedly blew cells, and stood for 3-5 min, the cells were completely lysed; 50 μL of lysate was added into a black 96-well plate, 50 μL substrate (300 m/mL Luc and 2 mg/mL ATP was mixed in a volume ratio of 3:1) was added and the fluorescence value on each well was quickly measured.

6. The killing efficiency was calculated as follows: the killing efficiency={(negative control fluorescence value−experimental group fluorescence value)/negative control fluorescence value}×100%.

The result is shown in FIG. 6. It can be seen that multi-functional proteins TiTE-2, 3, and 4 provided by the present invention could kill tumor cells in vitro at a very low concentration, and the optimal concentration for the best killing effect is 0.5-5 ng/10^6 cells.

Example 6. Multifunctional Protein TiTE-1 Stimulates the Expansion of NK Cell 1. 6×10^5 of NK92 cells (China Type Culture Collection) were culture in 2 mL medium (Alpha basal medium, 12.5% horse serum, 12.5% FBS, 0.2 mM inositol, 0.1 mM mercaptoethanol, 0.02 mM folic acid) with 40 ng/mL of multifunctional protein TiTE-1 obtained in Example 2 at 37° C., 5% CO2.

2. After 2-3 days of culture, the total number of cells was counted and cultured continuously for 18 days, the cell density was adjusted to 3×10^5 cells/mL for each passage, and 40 ng/mL of multifunctional protein TiTE-1 was maintained.

The cell growth curve is shown in FIG. 7. It can be seen that the multifunctional protein TiTE-1 provided by the present invention can stimulate NK cell expansion and has the function of IL15/IL15Rαsushi.

The IL15/IL15Rαsushi domains of TiTE2, 3, 4, 5, 6, 7, 9, 10, 11, 12, 13, and 15 are identical to TiTE-1, and their functions are not significantly different.

Example 7

FACS verification of CD19 and CD3 antigen binding for multifunctional protein TiTE-1 and antiMHC/WT1 and antiCD3 of TiTE-6, 8, 9, 10, 11, 12 for binding to intracellular antigen WT1 and CD3, respectively.

1. T cell experimental group and BV173 experimental group: 5 μg each of multifunctional protein TiTE-1, 6, 8, 9, 10, 11, 12 were added to the mixture of BV173 cells and 3×10^5 T cells which were derived from mononuclear cell-rich white membrane layer of normal human peripheral blood by density gradient centrifugation, and stimulated by OKT3 (50 ng/mL) and IL2 (300 IU/mL) for 14 days, and incubated on ice for 30 min. The supernatant was removed by centrifugation and the cells were re-suspended in 200 μL of PBS. 2 μL APC labelled Mouse anti-Human CD279 (BD, Cat. No. 558694) was added and incubated on ice for 30 min. The supernatant was removed by centrifugation and the cells were re-suspended in 200 μL of PBS.

T cell negative control group and BV173 cell negative control group: BV173 cells (ATCC) were mixed with 3×10^5 of T cells derived from mononuclear cell-rich white membrane layer of normal human peripheral blood by density gradient centrifugation and stimulated by OKT3 (50 ng/mL) and IL2 (300 IU/mL) for 14 days and 2 μL of APC labelled Mouse anti-Human CD279 (BD, Cat. No. 558694) was added and incubated on ice for 30 min. The supernatant was removed by centrifugation, and the cells were re-suspended in 200 μL of PBS as a negative control.

2. The results of flow cytometry shown in FIG. 8. It can be seen from the figure that the multifunctional protein TiTE-1 bound well to CD19 antigen and CD3 antigen, respectively; antiMHC/WT1 and anti-CD3 of TiTE-6, 8, 9, 10, 11, and 12 bound well to intracellular antigen antiCD3 function well with WT1 and CD3 antigen, respectively.

Example 8

FACS verification of the binding function of TiTE-2, 3 for MHC/GP100 and CD3 antigens and TiTE-4 for MHC/Mart1 and CD3 antigens respectively.

1. T cell and malme-3M-Luc (by transfecting luc gene into Malme-3M purchased by ATCC) experimental group: 5 μg of multifunctional protein TiTE-2, 3, 4 each was added to 3×10^5 T cells and malme-3M-Luc cells, respectively. and the cells were incubated on ice for 30 min. The supernatant was removed by centrifugation and the cells were resuspended in 200 μL of PBS. 2 μL of PE conjugated anti-hIL-15 (R&D, IC2471P) was added and kepton ice for 30 min. The supernatant was removed by centrifugation and the cells were resuspended in 200 μL of PBS.

T cell group and malme-3M-Luc cell negative control group: 2 μL APC Mouse anti-Human CD279 (BD, No. 558694) was added to 3×10^5 T cells and malme-3M-Luc, respectively, and the cells with the antibody were incubated on ice for 30 min. The supernatant was removed by centrifugation, and the cells were re-suspended in 200 μL of PBS as a negative control.

2. The results of flow cytometry analysis shown in FIG. 9. It can be seen from the figure that the multifunctional proteins TiTE-2 and 3 bind well to MHC/GP100 antigen and CD3 antigen, respectively, TiTE-4 binds to MHC/Mart1 antigen and CD3 antigen well.

Example 9

FACS verification of the binding function of antiCD19 and antiCD3 of the multifunctional protein TiTE-15, 16 to CD19 antigen and CD3 antigen, respectively 1. T cell and BV173 cell experimental group: 5 μg of multi-function proteins TiTE-15, 16 were added to BV173 cells and 3×10^5 T cells derived from mononuclear cell-rich white membrane layer of normal human peripheral blood by density gradient centrifugation, and stimulated by OKT3 (50 ng/mL) and IL2 (300 IU/mL) for 14 days, and incubated on ice for 30 min. The supernatant was removed by centrifugation and the cells were re-suspended in 200 μL of PBS. 2 μL of FITC-Labeled recombinant Protein L (ACRO Biosystem, RPL-PF141) was added and incubated on ice for 30 min. The supernatant was removed by centrifugation, washed twice in 500 μL PBS, and re-suspended in 200 μL of PBS.

T cell and BV173 cell negative control group: 3*10E5 T cells respectively (PBMC stimulated with 50 ng/mL OKT3, 300 IU/mL IL2) were mixed with BV173 cells (ATCC) first, and 2 μL APC Mouse anti-Human CD279 (BD, Cat. No. 558694) was added to the cells and incubated on ice for 30 min. The supernatant was removed by centrifugation, and the cells were re-suspended in 200 μL of PBS as a negative control.

2. The results of flow cytometry analysis shown in FIG. 10. It can be seen from the figure that the multifunctional proteins TiTE-15 and 16 bind well to the CD19 antigen and the CD3 antigen, respectively.

Example 10

FACS verification of the binding function of antiCD19, antiCD20 and antiCD3 of multifunctional protein TiTE-5 to respective antigens.1. T cell and malme-3M-CD19-Luc/malme-3M-CD22-Luc experimental groups. Cell experimental group: 5 μg of multi-function protein TiTE-5 was added to 3×10^5 T cells and malme-3M-CD19-Luc cells (by transfecting CD19 antigen gene and Luc gene into Malme-3M purchased by ATCC) and malme-3M-CD22-Luc (by transfecting CD22 antigen gene and Luc gene into Malme-3M purchased by ATCC) respectively, and incubated on ice for 30 min. The supernatant was re-suspended in 200 μL of PBS. 2 μL of PE conjugated anti-hIL-15 (R&D, IC2471P)

was added and incubated on ice for 30 min. The supernatant was centrifuged and the cells were re-suspended in 200 μL of PBS.

T cell and malme-3M-CD19-Luc, malme-3M-CD22-Luc cell negative control groups: 3×10^5 T cells were mixed with malme-3M-CD19-Luc, malme-3M-CD22-Luc, respectively. 2 μL PE conjugated anti-hIL-15 (R&D, article number IC2471P) was added to each groups and incubated on ice for 30 min. The supernatant was removed by centrifugation, and the cells were re-suspended in 200 μL of PBS as a negative control.

2. The results of flow cytometry analysis shown in FIG. 11. It can be seen from the figure that the multifunctional protein TiTE-5 binds well to the CD19 antigen, CD20 antigen and CD3 antigen, respectively.

INDUSTRIAL APPLICATION

The experiments of the present invention demonstrate that the multifunctional protein of the present invention can bind to different tumor antigens through two antigen binding domains that could bind to tumor-associated antigens, mediate specific cell killing, and improve the accuracy of targeting. It can block the immunosuppressive signal and improve the ability to kill tumor if one of the antigen binding domains is an immune check-point related antigen; the multifunctional protein of the present invention can play a role of a cytokine since it contains a cytokine and cytokine receptor complex.

---

What is claimed is:

1. A protein, comprising a main peptide chain and a co-peptide chain to constitute a heterodimer;
   the main peptide chain comprises an antigen 1 binding domain R1, a co-peptide chain linkage domain R2 and an antigen 2 binding domain R3;
   the co-peptide chain comprises an antigen 3 binding domain R4 and a main peptide chain linkage domain R5;
   the main peptide chain linkage domain R5 binds each other to the co-peptide chain linkage domain R2;
   the antigen 1 binding domain R1 is anti-CD19 ScFv, the co-peptide chain linkage domain R2 is IL15Rαsushi, the antigen 2 binding domain R3 is anti-CD3 ScFv, the antigen 3 binding domain R4 is the extracellular domain of PD1, the main peptide chain linkage domain R5 is IL15; and
   the main peptide chain comprises the amino acid sequence of SEQ ID NO: 8, and the co-peptide chain comprises the amino acid sequence of SEQ ID NO: 9.

2. An isolated nucleic acid molecule comprising a nucleotide sequence encoding the protein of claim 1.

3. An immune cell, wherein: the surface of the immune cell is bound with the protein according to claim 1.

* * * * *